United States Patent
Tran et al.

(10) Patent No.: US 11,793,403 B2
(45) Date of Patent: Oct. 24, 2023

(54) APPARATUS, SYSTEMS, AND METHODS FOR VISION ASSESSMENT AND TREATMENT

(71) Applicant: Vivid Vision, Inc., San Francisco, CA (US)

(72) Inventors: Tuan Tran, San Francisco, CA (US); Brian Dornbos, San Francisco, CA (US); Benjamin Backus, Oakland, CA (US); James J. Blaha, San Francisco, CA (US); Manish Gupta, San Francisco, CA (US)

(73) Assignee: Vivid Vision, Inc., San Francisco, CA (US)

( * ) Notice: Subject to any disclaimer, the term of this patent is extended or adjusted under 35 U.S.C. 154(b) by 404 days.

(21) Appl. No.: 17/202,143

(22) Filed: Mar. 15, 2021

(65) Prior Publication Data
US 2021/0290053 A1    Sep. 23, 2021

Related U.S. Application Data

(60) Provisional application No. 62/990,335, filed on Mar. 16, 2020.

(51) Int. Cl.
*A61B 3/11* (2006.01)
*G02B 27/00* (2006.01)
*G02B 27/01* (2006.01)

(52) U.S. Cl.
CPC .......... *A61B 3/111* (2013.01); *G02B 27/0093* (2013.01); *G02B 27/0172* (2013.01)

(58) Field of Classification Search
CPC ..... A61B 3/111; A61B 3/0025; A61B 3/0091; A61B 3/113; A61B 3/085; A61B 3/10;
(Continued)

(56) References Cited

U.S. PATENT DOCUMENTS

| 4,660,945 | A | * | 4/1987 | Trachtman | A61B 3/09 351/203 |
| 4,756,305 | A | * | 7/1988 | Mateik | A61H 5/00 601/37 |

(Continued)

OTHER PUBLICATIONS

"C38274: Essential course in depensing—part 16," (Jul. 11, 2014). Optician Online. Web. Retrieved Jun. 23, 2021. 13 pages, https://www.opticianonline.net/cet-archive/41.
(Continued)

*Primary Examiner* — Collin X Beatty
(74) *Attorney, Agent, or Firm* — Mintz, Levin, Cohn, Ferris, Glovsky and Popeo, P.C.

(57) ABSTRACT

Methods and systems for assessing and/or treating visual disorders, such as discorder in accommodative ability and/or vergence ability, of a person are provided. Assessment and training exercises can be performed utilizing a computerized system in communication with a head-mountable display (HMD), such as a virtual or augmented reality display, which can display visual targets at various vergence and accommodative demands. Lenses, such as inverted bifocal lenses, may be used in combination with the HMD to mimic natural accommodative demand during viewing or to enable assessment and treatment of accommodation disorders. Corrective factors can be calculated and utilized for generation of visual targets to account for lens characteristics and/or interpupillary distance mismatch. Accommodation and vergence responses can be tracked during display of the visual targets at the various demands, and assessed in comparison to normalized values for assessment of vision disorders or utilized to track progress of user in treatment of a vision disorder.

18 Claims, 15 Drawing Sheets

(58) Field of Classification Search
CPC ........... A61B 3/032; A61B 3/08; A61B 3/028;
A61B 3/09; A61B 3/14; A61B 3/005;
A61B 3/0058; A61B 3/18; A61B
2560/0475; A61B 2562/0204; A61B
2562/0219; A61B 2562/0247; A61B
3/0008; A61B 3/0041; A61B 3/022; A61B
3/024; A61B 3/0285; A61B 3/036; A61B
3/063; A61B 3/066; A61B 3/1005; A61B
3/101; A61B 3/1015; A61B 3/102; A61B
3/103; A61B 3/1035; A61B 3/12; A61B
3/1216; A61B 3/1241; A61B 3/13; A61B
3/145; A61B 3/165; A61B 5/0059; A61B
5/0066; A61B 5/0077; A61B 5/01; A61B
5/1103; A61B 5/12; A61B 5/14532; A61B
5/1455; A61B 5/14555; A61B 5/361;
A61B 5/369; A61B 5/398; A61B 5/6803;
A61B 5/7267; A61B 8/10; A61B 8/461;
G02B 27/0093; G02B 27/0172; G02B
2027/0138; G02B 2027/014; G02B
27/017; G02B 2027/0134; G02B
2027/0185; G02B 2027/0118; G02B
2027/0127; G02B 2027/0147; G02B
2027/0159; G02B 2027/0178; G02B
2027/0187; G02B 21/0032; G02B
27/0075; G02B 27/0179; G02B 3/14;
G02B 30/36; G02B 7/023; A61H 5/00;
A61H 2201/1604; A61H 2201/165; A61H
2201/5043; A61H 2205/024; A61H 5/005;
A61H 1/00; A61H 2201/1207; A61H
2201/5007; A61H 2201/5058; A61H
2201/5092

See application file for complete search history.

(56) References Cited

U.S. PATENT DOCUMENTS

| | | | |
|---|---|---|---|
| 10,890,759 B1* | 1/2021 | Held | G02B 27/0172 |
| 2002/0176051 A1 | 11/2002 | Saladin | |
| 2003/0232319 A1 | 12/2003 | Grisham et al. | |
| 2016/0270656 A1 | 9/2016 | Samec et al. | |
| 2017/0296421 A1* | 10/2017 | Travers | A61H 5/00 |
| 2018/0064333 A1* | 3/2018 | Apple | G06T 7/292 |
| 2019/0018236 A1 | 1/2019 | Perreault et al. | |
| 2020/0323728 A1* | 10/2020 | Park | G02F 1/29 |
| 2021/0275013 A1* | 9/2021 | Alvarez | G02B 27/017 |
| 2022/0151484 A1* | 5/2022 | Leube | A61B 3/028 |
| 2023/0114699 A1* | 4/2023 | Zimanyi | A61B 3/0058 703/11 |

OTHER PUBLICATIONS

"Introducing Deepfocus: The AI Rendering System Powering Half Dome," (Dec. 19, 2018). Oculus Blog. Posted by Oculus VR, Web. Retrieved Jun. 23, 2021. 16 pages. https://www.oculus.com/blog/introducing-deepfocus-the-ai-rendering-system-powering-half-dome/.

Feldman, J. M., Cooper, J., & Eichler, R. (1993). "The Effect of Stimulus Parameters (Size, Complexity, Depth, and Line Thickness) on Horizontal Fusional Amplitudes in Normal Humans." Binoc Vis Eye Muscle Surg Q, 8(1), 23-30.

Heiting. G. (2019, updated May 2021). "A Consumer Guide to Bifocal and Multifocal Contact Lenses," A Consumer Guide to Bifocal Contact Lenses, All About Vision. Web. Retrieved Jun. 23, 2021. 6 pages, https://www.allaboutvision.com/contacts/bifocals.htm.

Koulieris, G. A., Bui, B., Banks, M. S., & Drettakis, G. (2017). "Accommodation and Comfort in Head-Mounted Displays." ACM Transactions on Graphics (TOG), 36(4), 1-11.

Mulligan, J.B. et al. (2004). "Polarization analysis of the eye movement correlogram [Abstract]." Journal of Vision, 4( 8): 651, 651a, http://journalofvision.org/4/8/651/, doi:10.1167/4.8.651.

Mulligan, J.B. et al. (Mar. 5, 2013) "Reflexive and voluntary control of smooth eye movements," Proc. SPIE 8651, Human Vision and Electronic Imaging XVIII, 86510Z ; https://doi.org/10.1117/12.2010333. 23 pages.

Scheiman, M. et al. (2008). "A Randomized Clinical Trial of Treatments for Symptomatic Convergence Insufficiency in Children." Arch Ophthalmol, 126(10), 1336-1349.

Schor, C. M., & Kotulak, J. C. (1986). "Dynamic Interactions Between Accommodation and Convergence are Velocity Sensitive." Vision Research, 26(6), 927-942.

Sheliga, B. M., Fitzgibbon, E. J., & Miles, F. A. (2006). "Short-latency disparity vergence eye movements: A response to disparity energy." Vision Research, 46(21), 3723-3740.

Stevenson, S. B., Cormack, L. K., & Schor, C. M. (1994). "The Effect of Stimulus Contrast and Interocular Correlation on Disparity Vergence." Vision Research, 34(3), 383-396.

* cited by examiner

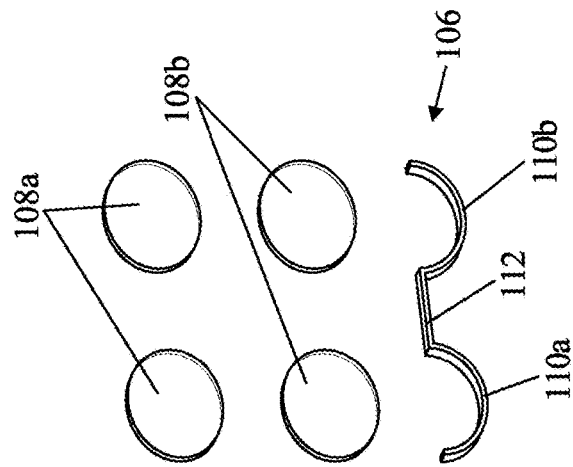
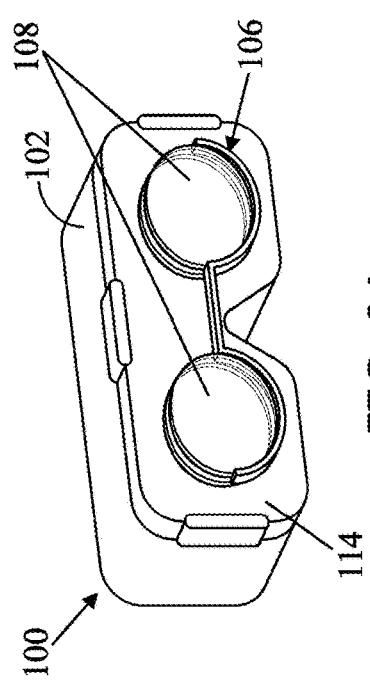
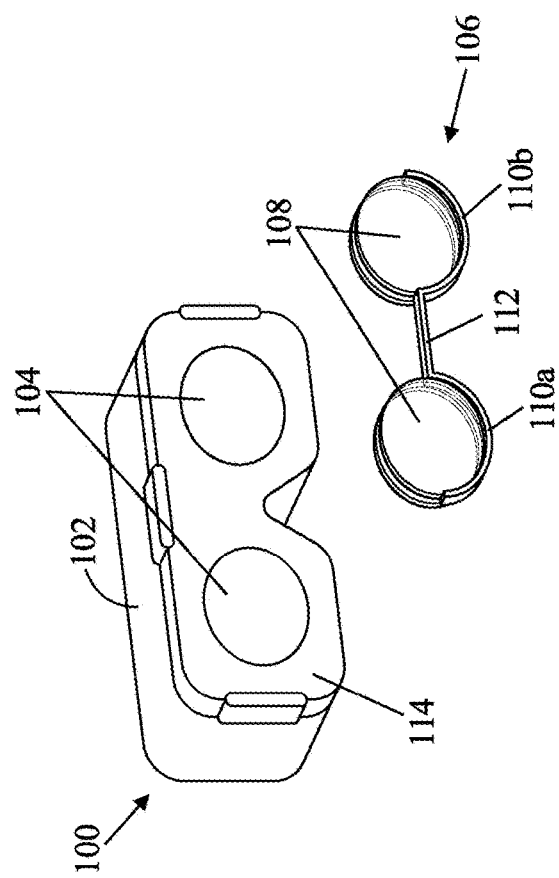

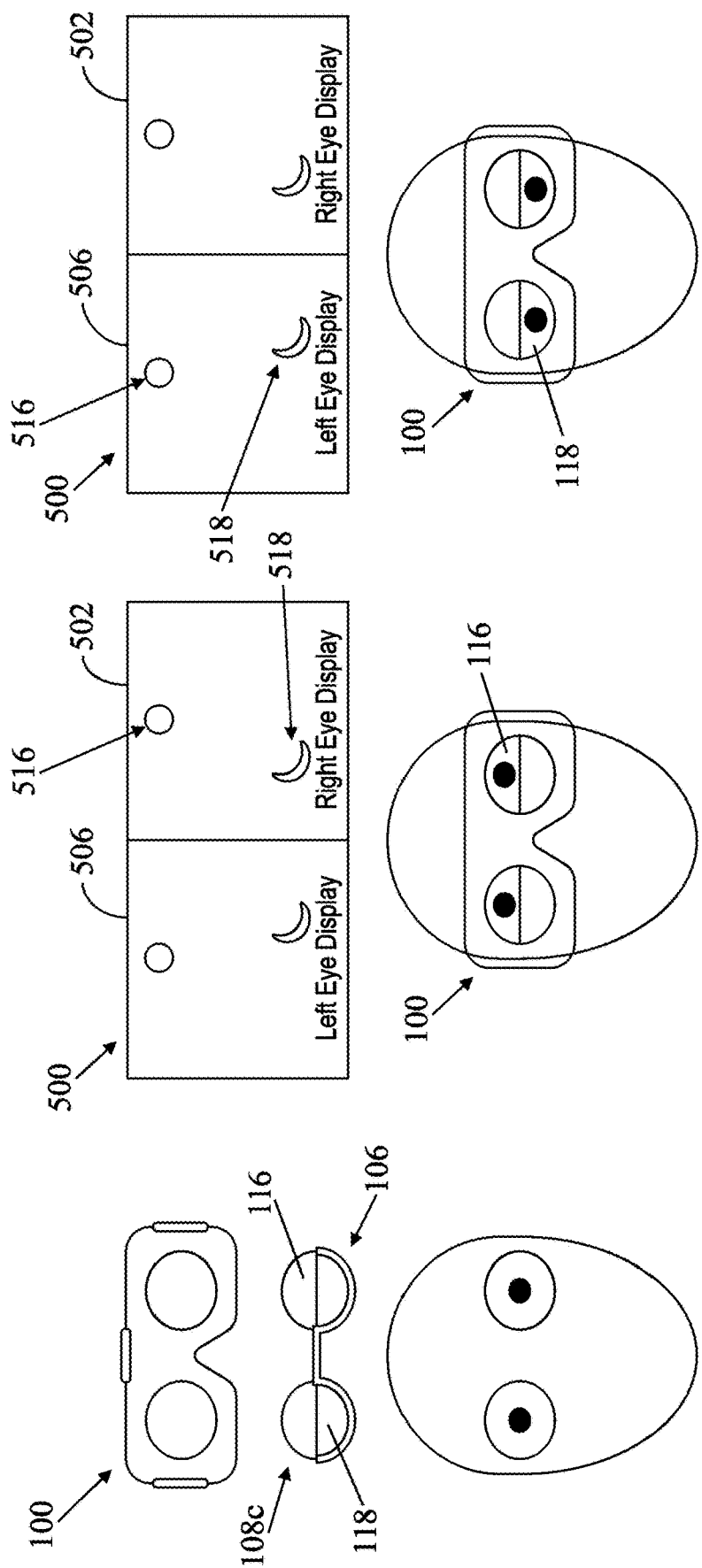

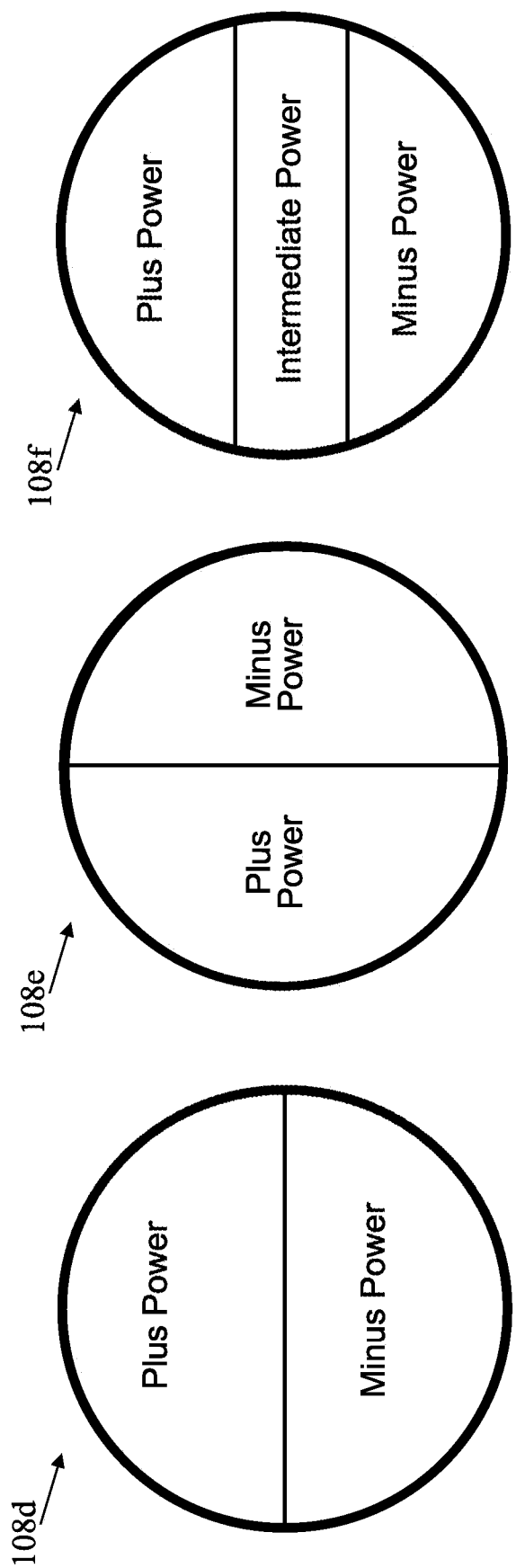

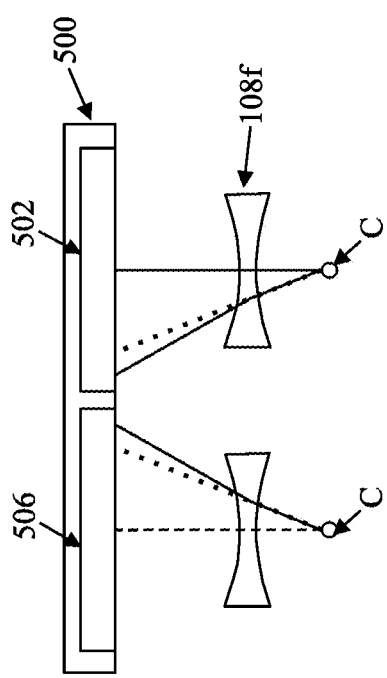
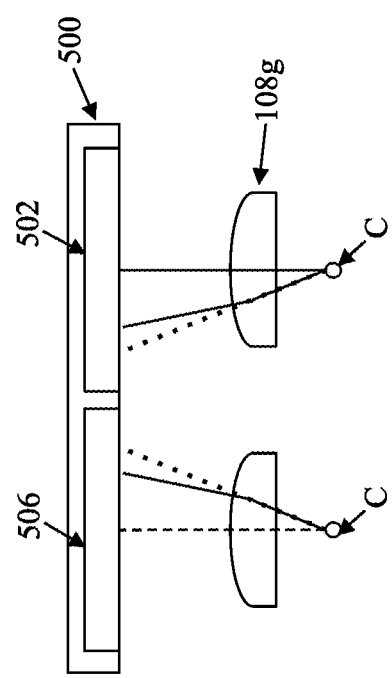
FIG. 3E
FIG. 3G
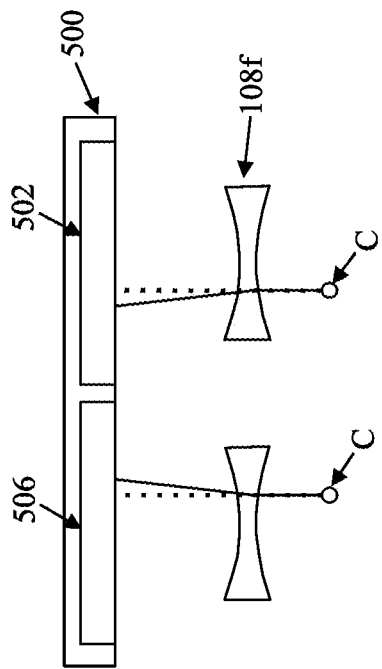
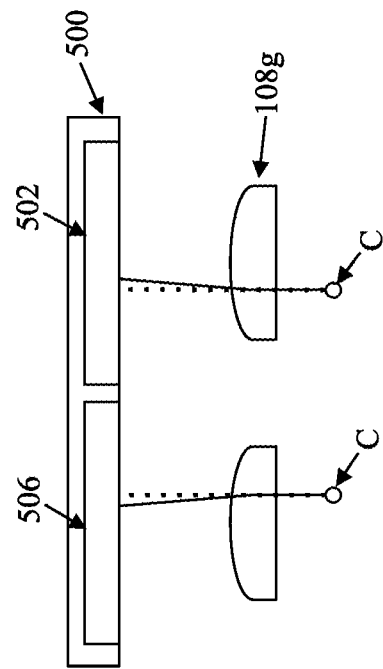
FIG. 3F
FIG. 3H

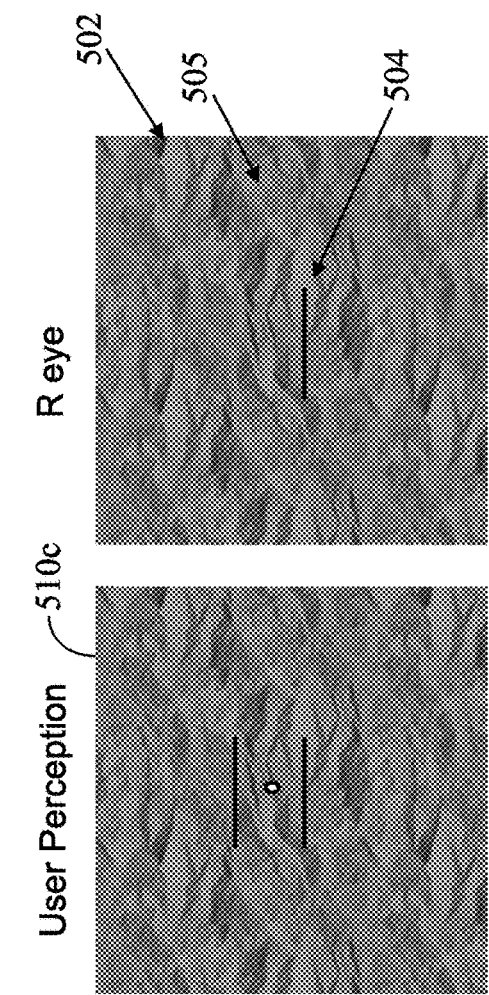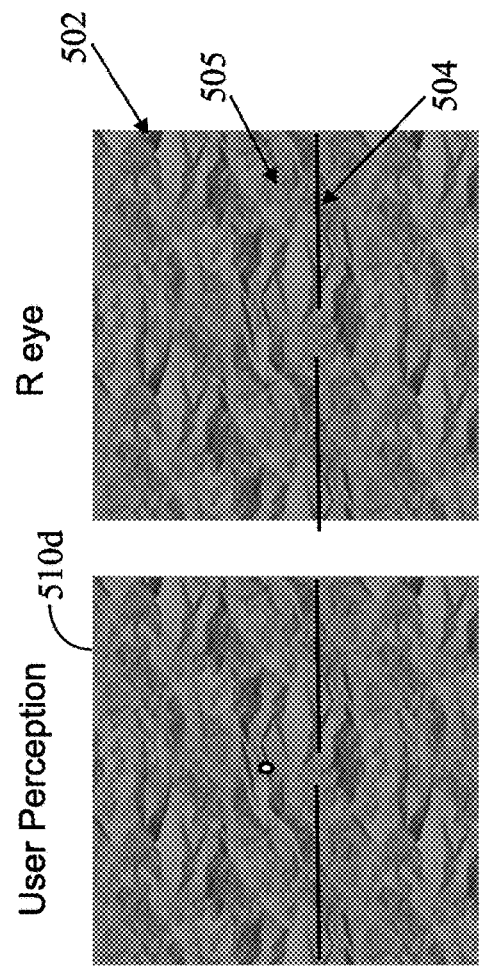
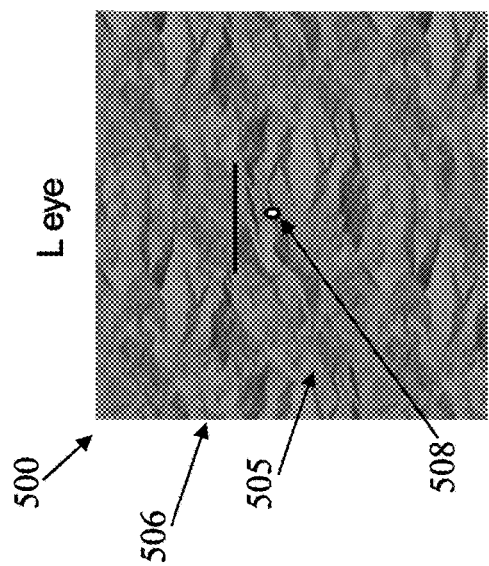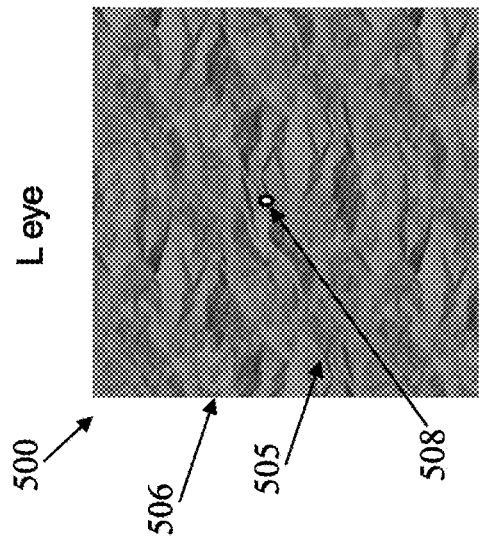
FIG. 5C
FIG. 5D

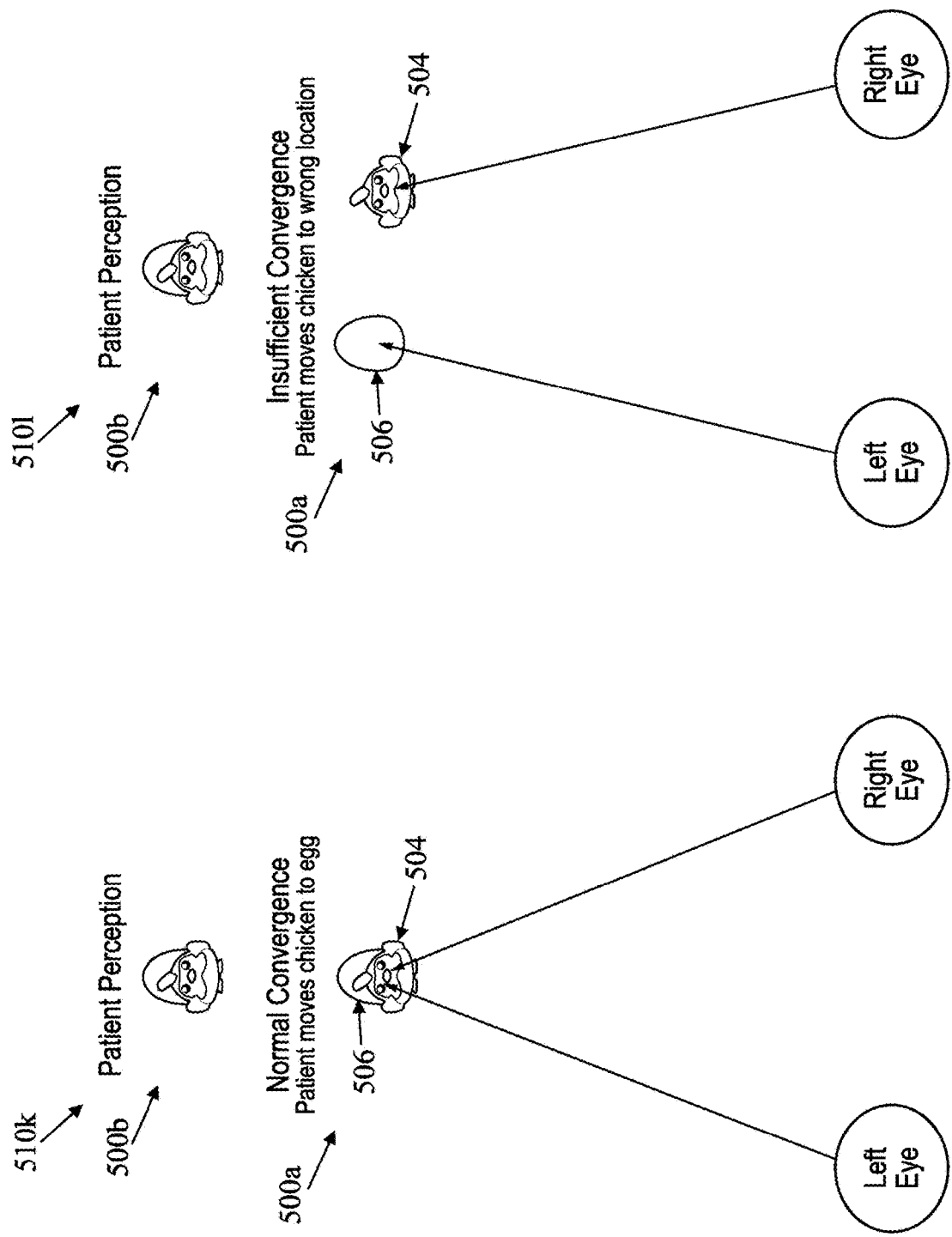

APPARATUS, SYSTEMS, AND METHODS FOR VISION ASSESSMENT AND TREATMENT

CROSS REFERENCE TO RELATED APPLICATIONS

The present application claims priority to U.S. Provisional Patent Application No. 62/990,335, filed Mar. 16, 2020, entitled "Virtual Reality-Based Assessment and Treatment of Vergence and Accommodative Demand," the disclosure of which is incorporated herein by reference in its entirety.

TECHNICAL FIELD

Apparatus, systems, and methods for analysis, diagnosing, monitoring, and/or treatment of vision disorders, such as phoria, vergence disorders, and/or accommodation disorders, are provided.

BACKGROUND

Millions of people globally suffer from visual disorders of binocular vergence control (the simultaneous movement of both eyes in opposite directions to obtain or maintain single binocular vision) and/or lenticular accommodation (the ability of the eye to increase its refractive power of the crystalline lens in order to focus near objects on the retina). For example, the ability to make vergence eye movements or to accommodate accurately may be impaired as the result of physical injury to muscles and structures of the eye and orbit, or by injury to the nervous system components that control these movements, such as may occur with trauma to the head, or stroke. In another example, vergence control and accommodation can be affected by aging. In another example, vergence control and accommodation can be affected by innate or acquired deficiencies in the visual system during development of the visual system during childhood. These reductions in ability to make vergence eye movements and reductions in ability to accommodate can be diagnosed and treated with rehabilitation exercises Eye care professionals have developed techniques for testing and training the visual system's ability to verge (change the convergence posture of the eyes) and accommodate (focus by changing the power of the lens in the eye). However, many currently used systems and methods are cumbersome, inaccurate, and imprecise.

SUMMARY

Apparatus, systems and methods for vision assessment and disorder treatment, such as apparatus, systems, and methods for assessing and treating vergence and accommodation disorders, are provided.

In one aspect, systems for one or more of assessment or training of one or more vision disorders of a user, where the systems are configured for data communication with a display apparatus, are disclosed. In embodiments, a system comprises one or more processor apparatus, and one or more computer-readable storage media having a plurality of computer-executable instructions stored thereon. Further, in such embodiments, the plurality of computer-executable instructions configured to, when executed by the one or more processor apparatus, cause the system to perform a plurality of steps comprising: identifying a specified exercise for display on the display apparatus, the specified exercise being one of a plurality of exercises configured for one or more of assessment or training of at least one of vergence ability or accommodation ability of the user; identifying data related to one or more lenses for use in combination with the display apparatus; based at least on the data related to the one or more lenses, calculating one or more correction factors for image display on the display apparatus; causing display, on the display apparatus and based at least on the specified exercise and the one or more correction factors, a series of visual stimuli to at least one eye of the user, each visual stimulus of the series of visual stimuli configured to have a specified vergence demand and a specified accommodation demand; tracking one or more of a vergence response or an accommodation response of the user; comparing the one or more of the vergence response or the accommodation response to one or more standardized values for vergence response or accommodation response: and determining, based at least on the comparing, a result indicative of whether the one or more of the vergence response or the accommodation response is associated with visual disorder.

In implementations, the system is configured to enable, based on the specified exercise targeting accommodative disorder, each visual stimulus in the series to have, relative to one or more other visual stimuli of the series, fixed vergence demand and varying accommodative demand; the system is further configured to enable, based on the specified exercise targeting vergence disorder, each visual stimulus in the series to have, relative to one or more other visual stimuli of the series, fixed accommodative demand and varying vergence demand; and the system is further configured to enable, based on targeting the specified exercise targeting combined vergence and accommodation disorder, each visual stimulus in the series to have, relative to one or more other visual stimuli of the series, a varying combination of accommodative demand and vergence demand.

In implementations, the display apparatus comprises a head-mountable display device. In variants, the head-mountable display device comprises one or more eye tracking sensors, and the plurality of steps further comprise: causing calibration of the one or more eye tracking sensors to the at least one eye of the user; and utilizing data received from the one or more eye tracking sensors for the tracking of the one or more of the vergence response or the accommodation response of the user.

In other implementations, the display apparatus comprises a multi-distance display apparatus comprising a first display device and a second display device, the first display device positioned distal of the second display device relative to the user. In variants, the second display device comprises a computerized mobile device comprising a forward facing camera and a rearward facing camera, and the forward facing camera is configured to enable a determination of a first distance between the computerized mobile device and the first display device, and the rearward facing camera is configured to enable a determination a second distance between the computerized mobile device and the user. In such variants, the plurality of steps further comprises: receiving, from the computerized mobile device, data indicative the first distance and data indicative of the second distance, wherein the causing display of the series of visual stimuli to the at least one eye of the user is further based on the data indicative of the first distance and the data indicative of the second distance: receiving, from a user input device, data indicative of user input with respect to perception of visual stimuli; and utilizing the data indicative of user input with respect to perception of visual stimuli for the tracking of the one or more of the vergence response or the accommodation response of the user.

In implementations, the tracking one or more of a vergence response or an accommodation response of the user comprises receiving input from a clinician administering the specified exercise.

In embodiments, the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a region of a lens, or a curvature of a lens. In implementations, the data indicative of one or more lens characteristics comprises data indicative of a plus power at an upper region of a lens and a minus power a lower region of a lens.

In implementations, the calculating the one or more correction factors for image display on the display apparatus comprises calculating, for an eccentric visual stimulus of the series of visual stimuli, a scaling factor, the scaling factor comprising one of a magnification factor based on a minification power of a minus lens or a minification factor based on a magnification power of a plus lens.

In implementations, the plurality of steps further comprises: determining, based at least on the tracking the one or more of the vergence response or the accommodation response of the user, an accommodation value associated with the accommodation response, the accommodation value comprising one or more of an accommodative amplitude, an accommodative facility, an accommodative accuracy, an accommodative-convergence-to-accommodation gain or ratio (ACA ratio), or a convergent-accommodation-to-convergence gain or ratio (CAC ratio).

In implementations, the plurality of steps further comprises: determining, based at least on the tracking the one or more of the vergence response or the accommodation response of the user, a vergence value associated with the vergence response, the vergence value comprising one or more of a vergence facility, a vergence accuracy, a vergence fatigue, a fixation stability, a fixation disparity, or a binocular fixation breakpoint.

In implementations, the plurality of steps further comprises: identifying data related to an interpupillary distance mismatch between the user and at least two of the one or more lenses, wherein the calculating the one or more correction factors for image display is further based on the interpupillary distance mismatch, and comprises calculating, for a visual stimulus of the series of visual stimuli, a displacement factor.

In implementations, the comparing the one or more of the vergence response or the accommodation response to the one or more standardized values for vergence response or accommodation response comprises: utilizing a look up table of standardized values based on one or more of average values from a plurality of individuals with healthy vision or simulated optimal vision values; and evaluating the one or more of the vergence response or the accommodation response of the user relative to at least one standardized value in the look up table of standardized values. In variants, the at least one standardized value comprises an acceptable range, and the evaluating comprises determining whether the one or more of the vergence response or the accommodation response is outside of the acceptable range, and wherein the one or more of the vergence response or the accommodation response being outside of the acceptable range is indicative of visual disorder. In other variants, the at least one standardized value comprises a threshold value, and the evaluating comprises determining whether the one or more of the vergence response or the accommodation response is below the threshold value, and wherein the one or more of the vergence response or the accommodation response being below the threshold value is indicative of visual disorder.

In implementations, the output related to the result comprises at least one of displayed output related to a predicted diagnosis or a user feedback indicative of accuracy of user performance in the specified exercise.

In another aspect, methods of operating systems configured for one or more of assessment or training of one or more vision disorders of a user are disclosed. In embodiments, the method comprises: identifying a specified exercise for display on a display apparatus, the specified exercise being one of a plurality of exercises configured for one or more of assessment or training of at least one of vergence ability or accommodation ability of the user; identifying data related to one or more lenses for use in combination with the display apparatus: based at least on the data related to the one or more lenses, calculating one or more correction factors for image display on the display apparatus; causing display, on the display apparatus and based at least on the specified exercise and the one or more correction factors, of one or more visual stimuli to at least one eye of the user, each of the one or more visual stimuli configured to have a specified vergence demand and a specified accommodation demand; tracking one or more of a vergence response or an accommodation response of the user; comparing the one or more of the vergence response or the accommodation response to one or more standardized values for vergence response or accommodation response; and determining, based at least on the comparing, a result indicative of whether the one or more of the vergence response or the accommodation response is associated with visual disorder.

In implementations, the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a portion of a lens, or a curvature of a lens. In variants, the identifying the data related to the one or more lenses comprises receiving data related to a marker associated with at least one of the one or more lenses, the marker indicative of the one or more lens characteristics. In other variants, the identifying data related to the one or more lenses comprises receiving a user input from at least one of the user or a clinician, the user input related to the one or more lens characteristics.

In implementations, the calculating the one or more correction factors for image display on the display apparatus comprises calculating, for an eccentric visual stimulus of the one or more visual stimuli, a scaling factor, the scaling factor comprising one of a magnification factor based on a minification power of a minus lens or a minification factor based on a magnification power of a plus lens.

In implementations, the method further comprises identifying data related to an interpupillary distance mismatch between the user and at least two of the one or more lenses, wherein the calculating the one or more correction factors for image display is further based on the interpupillary distance mismatch, and comprises calculating, for a visual stimulus of the one or more visual stimuli, a displacement factor.

In implementations, the causing display of one or more visual stimuli to the at least one eye of the user comprises displaying a series of visual stimuli for the specified exercise to the at least one eye of the user. In variants, each visual stimulus in the series of visual stimuli has a fixed vergence demand and a varying accommodative demand relative to one or more others of the visual stimuli in the series. In other variants, each visual stimulus in the series of visual stimuli has a fixed accommodative demand and a varying vergence demand relative to one or more others of the visual stimuli in the series. In yet other variants, each visual stimulus in the series of visual stimuli has a varying combination of accommodative demand and vergence demand relative to one or more others of the visual stimuli in the series.

In implementations, the display apparatus comprises a head-mountable display device comprising one or more eye tracking sensors, and the method further comprises: causing calibration of the one or more eye tracking sensors to the at least one eye of the user; and utilizing data received from the one or more eye tracking sensors for the tracking of the one or more of the vergence response or the accommodation response of the user.

In other implementations, the display apparatus comprises a multi-distance display apparatus comprising a first display device and a second display device, the first display device positioned distal of the second display device relative to the user, and the method further comprises: identifying data indicative a first distance between the first display device and the second display device; identifying data indicative of the second distance between the second display device and the user, wherein the causing display of the series of visual stimuli to the at least one eye of the user is further based on the data indicative of the first distance and the data indicative of the second distance; receiving, from a user input device, data indicative of user input with respect to perception of visual stimuli; and utilizing the data indicative of user input with respect to perception of the one or more visual stimuli for the tracking of the one or more of the vergence response or the accommodation response of the user.

In implementations, the method further comprises determining, based at least on the tracking the one or more of the vergence response or the accommodation response of the user, an accommodation value associated with the accommodation response, the accommodation value comprising one or more of an accommodative amplitude, an accommodative facility, an accommodative accuracy, an accommodative-convergence-to-accommodation gain or ratio (ACA ratio), or a convergent-accommodation-to-convergence gain or ratio (CAC ratio).

In implementations, the method further comprises determining, based at least on the tracking the one or more of the vergence response or the accommodation response of the user, a vergence value associated with the vergence response, the vergence value comprising one or more of a vergence facility, a vergence accuracy, a vergence fatigue, a fixation stability, a fixation disparity, or a binocular fixation breakpoint.

In implementations, the comparing the one or more of the vergence response or the accommodation response relative to the one or more standardized values for vergence response or accommodation response comprises: utilizing a look up table of standardized values based on one or more of average values from a plurality of individuals with healthy vision or simulated optimal vision values; and evaluating the one or more of the vergence response or the accommodation response of the user relative to at least one standardized value in the look up table of standardized values. In variants, the at least one standardized value comprises an acceptable range, and the evaluating comprises determining whether the one or more of the vergence response or the accommodation response is outside of the acceptable range, and wherein the one or more of the vergence response or the accommodation response being outside of the acceptable range is indicative of visual disorder. In other variants, the at least one standardized value comprises a threshold value, and the evaluating comprises determining whether the one or more of the vergence response or the accommodation response is below the threshold value, and wherein the one or more of the vergence response or the accommodation response being below the threshold value is indicative of visual disorder.

In implementations, the output related to the result comprises at least one of displayed output related to a predicted diagnosis or a user feedback indicative of accuracy of user performance in the specified exercise.

In another aspect, systems for one or more of assessment or training of a vision disorder associated with at least one of vergence ability or accommodation ability of a user, where the systems are configured for data communication with a head-mountable display device, are disclosed. In embodiments, a system comprises one or more processor apparatus; and one or more computer-readable storage media having a plurality of computer-executable instructions stored thereon. In such embodiments, the plurality of computer-executable instructions configured to, when executed by the processor apparatus, cause the system to perform a plurality of steps comprising: identifying a specified exercise for display on a head-mountable display device, the specified exercise being one of a plurality of exercises; identifying data related to one or more lenses for use in combination with the head-mountable display device; based at least on the data related to the one or more lenses, calculating one or more correction factors for image display on the head-mountable display device; calibrating one or more eye tracking sensors to at least one eye of the user; causing display, on the head-mountable display device and based at least on the specified exercise and the one or more correction factors, of a series of visual stimuli to at least one eye of the user, each visual stimulus in the series of visual stimuli configured to have a specified vergence demand and a specified accommodation demand; tracking, via at least the one or more eye tracking sensors, one or more of a vergence response or an accommodation response of the user; evaluating the one or more of the vergence response or the accommodation response relative to one or more standardized values for vergence response or accommodation response; and determining, based at least on the evaluation, a result indicative of whether the one or more of the vergence response or the accommodation response is associated with visual disorder.

In implementations, the system is configured to enable, based on the specified exercise targeting accommodative disorder, each visual stimulus in the series to have, relative to one or more other visual stimuli of the series, fixed vergence demand and varying accommodative demand; the system is further configured to enable, based on the specified exercise targeting vergence disorder, each visual stimulus in the series to have, relative to one or more other visual stimuli of the series, fixed accommodative demand and varying vergence demand; and the system is further configured to enable, based on targeting the specified exercise targeting combined vergence and accommodation disorder, each visual stimulus in the series to have, relative to one or more other visual stimuli of the series, a varying combination of accommodative demand and vergence demand.

In implementations, the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a region of a lens, or a curvature of a lens.

In yet another aspect, methods of assessment or training of a vision disorder associated with at least one of vergence ability or accommodation ability of a user utilizing a display system are disclosed. In embodiments, a method comprises selecting a specified exercise via a user interface in data communication with the display system; selecting one or more lenses for use with the display system, the display system comprising one of a head-mountable display or a multi-distance display system, the selecting of the one or more lenses based at least on the specified exercise; disposing the one or more lenses between at least one eye of the user and the display system, the one or more lenses comprising at least one lens having a plus power portion and a minus power portion; running the specified exercise, wherein the specified exercise is configured to display, on the display system, a series of visual stimuli to the user, each of the one or more visual stimuli configured to have a specified vergence demand and a specified accommodation demand, the series of visual stimuli configured for one or more of analysis or training of the at least one of the vergence ability or the accommodation ability of the user; and collecting user input indicative of perception of the series of visual stimuli.

In implementations, the at least one lens is disposed between the at least one eye of the user and the display system such that the plus power portion is oriented toward a top of the lens and the minus power portion is oriented toward a bottom of the lens.

In implementations, the at least one lens further comprises a prism in at least one of the plus power portion or the minus power portion.

In still another aspect, head-mountable display devices configured for communication with a system for one or more of assessment or training of a vision disorder associated with at least one of vergence ability or accommodation ability of a user are disclosed. In embodiments, a head-mountable display device comprises: a display housing; one of a virtual reality display or an augmented reality display disposed in the display housing; head-mounting apparatus, the head-mounting apparatus configured for attachment of the display housing to the head of the user, a lens receiver; and one or more lenses configured for attachment to the lens receiver. In such embodiments, the one or more lenses comprise at least one lens having a plus power portion and a minus power portion. Further, in such embodiments, the at least one lens is configured to be disposed between at least one eye of the user and the one of the virtual reality display or the augmented reality display such that the plus power portion is oriented toward a top of the lens and the minus power portion is oriented toward a bottom of the lens.

In implementations, the lens receiver comprises a pair of spectacle frames configured to be worn by the user in combination with the display housing.

In other implementation, the lens receiver is attached to or disposed within the display housing.

In still other aspects, lenses for use with a system configured for one or more of assessment or training of a vision disorder associated with at least one of vergence ability or accommodation ability of a user are disclosed.

In still other aspects, methods of utilizing lenses with a system configured for one or more of assessment or training of a vision disorder associated with at least one of vergence ability or accommodation ability of a user are disclosed.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

The present disclosure will be more fully understood from the following detailed description taken in conjunction with the accompanying drawings, in which:

FIGS. 1A-1C are perspective views of an exemplary head-mountable display (HMD) and lenses configured for use therewith in accordance with embodiments of the present disclosure;

FIGS. 1D-1F are schematic illustrations of use of the exemplary HMD and lenses illustrated in FIGS. 1A-1C;

FIGS. 1G-1I are schematic illustrations of exemplary configurations for lenses that can be used in combination with the HMD shown in FIGS. 1A-IC;

FIGS. 3E-3H are schematic illustrations of exemplary testing/training configurations utilizing lenses in combination with a display system in accordance with embodiments described herein, wherein image correction is applied;

FIGS. 5A-5D are views of exemplary testing/training scenarios generated on a display, which include visual targets configured for assessing phoria in accordance with embodiments of the present disclosure.

FIGS. 5K and 5L are views of exemplary testing/training scenarios generated on a display, which include visual targets configured for assessing and/or treatment of vergence disorders in accordance with embodiments of the present disclosure.

DETAILED DESCRIPTION

Figure 1J:
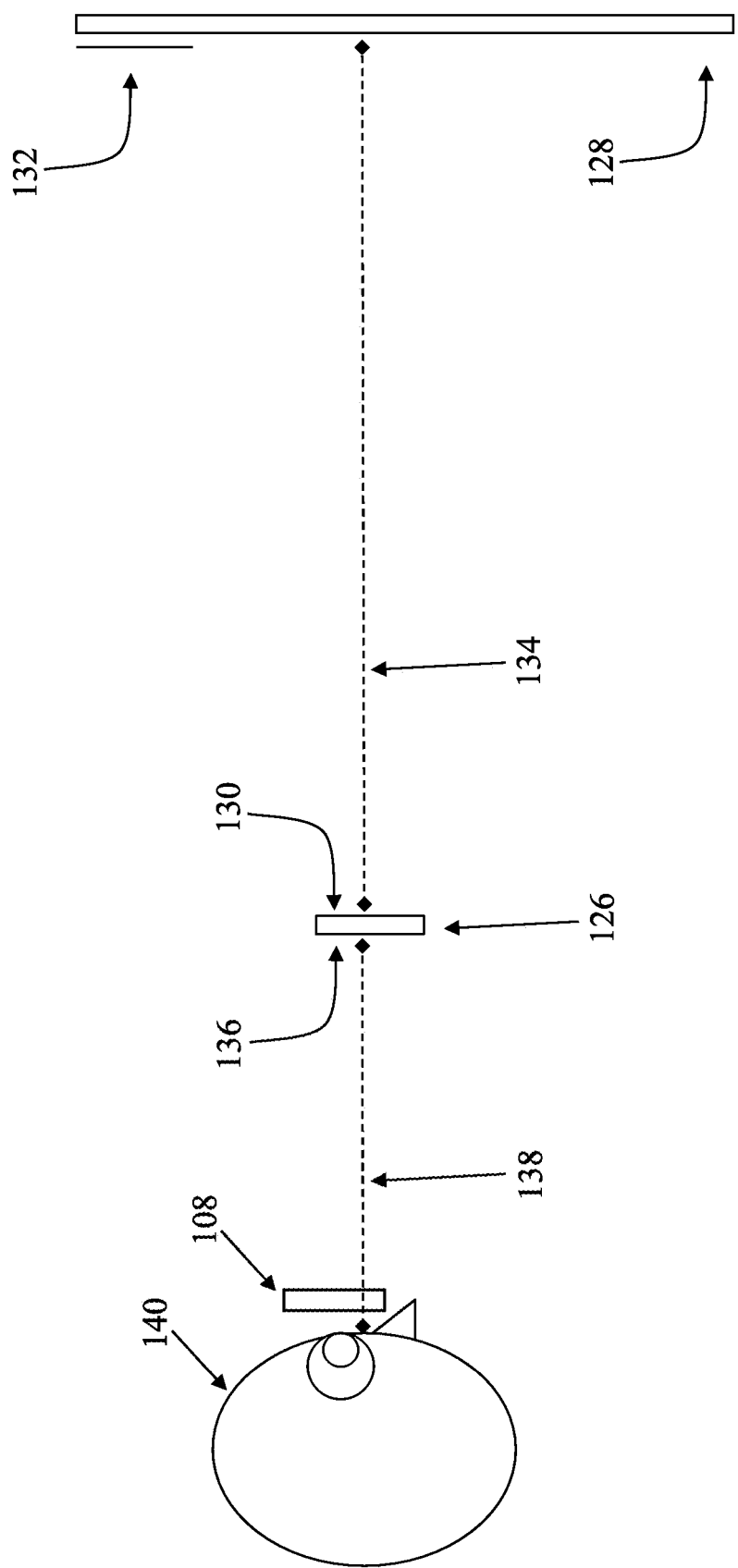
FIG. 1J is a schematic illustration of an exemplary multi-distance display system and lenses for use therewith in accordance with embodiments of the present disclosure.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions ar not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Like reference symbols in the various drawings indicate like elements.

Overview

In exemplary aspects, apparatus (devices), systems, and methods are provided for diagnosis and monitoring, and/or treating patients' visual disorders, including disorders affecting vergence control and/or accommodation of a patient. In certain embodiments, the methods and devices are used in head-mountable virtual reality devices that provide a visual reality environment on their virtual reality displays. However, in other embodiments, the methods and devices can be utilized in other devices with similar environments, such as augmented reality or mixed reality environments in a mobile computing device or other computing device(s). Therefore, it will be appreciated that the systems and methods described herein apply to virtual reality, augmented, reality, mixed reality, or similar environments.

In exemplary implementations, a head-mountable display (HMD) device has or is configured for communication with computing hardware configured to perform operations for analyzing a patient's visual ability. The analysis (which can include on or more of diagnosis, monitoring of a treatment, or administration of treatment) can be performed in an automated manner that is comfortable to the patient. Moreover, the HMD device can be used to perform the analysis in a cost and/or time-saving manner. Various disorders, such as, for example, vergence disorders and accommodation disorders, as well as routine eye care check-ups, can be addressed using a high quality visual assessment test which can be performed in a relatively short time period. For example, in some implementations, the analysis can be performed in 5 minutes or less, though it should be appreciated that other time periods can be required depending on various factors, including the desired statistical confidence, the amount of time the patient has to take the test, visual fatigue, and/or the purpose of the test (e.g. for screening or diagnosis vs. monitoring or training).

The head-mounted displays used in virtual reality and augmented reality headsets allow for dichoptic presentation of visual stimuli under computer control and are thus well suited to the implementation of these methods. In particular, monocularly visible elements can be displayed separately to each of the two eyes (i.e., a different image shown to each eye), with or without binocularly visible elements (i.e., the same image displayed to each eye). However, although vergence ability and accommodative ability are often linked, most head-mounted displays use optics with fixed accommodative demand, and in order to test and treat disorders of accommodation, the accommodative demand of the display must be varied. Therefore, currently used head-mountable displays are insufficient for assessment and treatment of accommodation disorders.

Another disadvantage associated with the traditional assessment of vergence and/or accommodative control is that the changes in viewing distance of a real or simulated object can be uncomfortable to the patient during testing. For example, the user's visual system may issue neural commands to the ciliary body (which controls accommodation) or to the eye muscles (which control vergence) that cannot be fully executed because the command conflicts with physical limitations or with other neural commands, which can be uncomfortable to the patient.

Furthermore, existing systems are either manually operated by a human operator or automated. Manually operated systems generally use simple, inexpensive tools, but the analysis results from such systems are subject to systematic bias and imprecision due to introduction of human error (e.g., a lesser trained operator may not operate the tools or read the results correctly). Existing automated systems remove human bias and error to a significant degree, however they require machines that are bulky, expensive, and immobile.

Accordingly, there is a need for improved techniques for analysis, diagnosis, and treatment of vergence and accommodation disorders.

In one aspect, the systems and techniques in accordance with the present disclosure include new devices and methods for assessment and treatment of visual disorders, which employ, in embodiments, the use of bifocal or n-focal (n>2) lenses with discrete zones having different dioptric powers in combination with head-mountable displays. For example, in implementations, an inverted Franklin bifocal with greater minus power in the bottom lens than the top lens is used in combination with a head-mountable display.

In embodiments, in order to assess the ability to accommodate, the system can measure accommodative amplitude (the total range or amount that a person can accommodate, usually expressed in diopters, such as 1/m or meters$^{-1}$), facility (how quickly the patient responds to a change of accommodative demand of the visual stimulus and/or how long it takes to achieve criterion accommodative state), and/or accuracy (how closely the accommodative state matches the demand of the visual stimulus to bring it into focus). In implementations, one or more of these functions can be measured indirectly by monitoring the pupil constriction responses in at least one eye, for example, by using one or two cameras placed within the headset that are pointed at the left and/or right eyes. These functions can be defined independently of overall refractive state or ability. For example, while it is important to measure the patient's ability to see both near and far stimuli clearly, amplitude is defined by the difference in near and far accommodative endpoints independent of whether the eye(s) being tested are myopic (nearsighted), emmetropic (having no visual defects), or hyperopic (farsighted). Thus, amplitude can be measured while a person is wearing prescribed ophthalmic lenses that allow them to see clearly at near or far distance.

Further, the ratio of accommodative convergence to the unit of accommodation (i.e., the accommodative-convergence-to-accommodation gain or ratio (ACA ratio)) is an index of the degree of accommodative convergence. Similarly, a convergence response to a stimulus will, in the absence of a stimulus to accommodation, elicit a concurrent accommodation response termed convergence accommodation. The ratio of convergence accommodation to the unit of convergence (i.e., the convergent-accommodation-to-convergence gain or ratio (CAC ratio)) is an index of the degree of convergence accommodation. In embodiments of the presently described systems, devices and methods, the CAC and ACA ratios can be measured because vergence demand and accommodative demand can each be manipulated independently in the headset.

In embodiments, in order to assess vergence ability, a patient's vision can be put under stress (vergence demand). Vergence ability may be measured by testing vergence ability independently or by testing the vergence ability while the individual is accommodating. The starting point of these activities may be zero stress but may also be adjusted to the level at which the individual can start the activity. In implementations, the amount of stress (or vergence demand) the individual's vision can tolerate is measured in degrees of visual angle or prism diopters and is performed by progressively increasing vergence stress via the vision assessment system. The amount of vergence demand the individual can withstand prior to image deterioration (i.e., an image becoming blurry and/or deteriorating so that an individual becomes diplopic) can be recorded, and then vergence demand can be reduced from this breakpoint until the individual is able to regain clear, single image vision. In implementations, the ability of an individual's vision to withstand vergence demand can be tested with both horizontal (near and/or far) and vertical stressors. A near, far, or vertical breakpoint can be measured by adding (respectively) progressive near, far, or vertical demand to the visual stimulus on a single or repeated basis until the eyes are no longer able to maintain fusion, at which point they will relax to a more habitual posture. The breakpoint is the maximum demand that the vision of the individual is able to withstand.

In embodiments, in order to assess vergence ability, an individual's ability to converge and diverge can be measured or otherwise determined. For example, the system can measure vergence facility (how quickly the individual can respond with a convergent, divergent, supravergent, or infravergent eye movement in response to change in binocular disparity of a visual target), vergence accuracy (how well an individual can direct each eye at the same point in space), and/or vergence fatigue (how long an individual can maintain convergence eye posture when viewing a near visual target). Fixation stability (fluctuation in vergence eye posture) and fixation disparity (how far in front or behind the visual target the eyes are converged, which can be different for near and far targets) can also be determined.

As a result of interactions between the vergence and accommodation abilities, the near and far breakpoints, as measured by the amount of vergence-inducing prism or horizontal displacement that an individual's vision can tolerate to maintain binocular fusion and alignment, can be altered by changing the accommodative demand using lenses. In particular, if a spherical lens with plus power is interposed between the eyes and a stimulus, the far breakpoint may be increased (made more uncrossed) and the near breakpoint may be decreased (also made more uncrossed). If a spherical lens with minus power is interposed, the far breakpoint may be decreased (made more crossed) and the near point may be increased (also made more crossed).

In addition to convergent, divergent, supravergent, and infravergent binocular eye movements, an individual's eyes are also capable of cyclovergent eye movements. That is, when viewing a binocular stimulus, the eye(s) may rotate about their visual axes to bring the retinal images into rotational alignment. The ability to cycloverge may be compromised in an individual, in which case the individual may show symptoms of strain and reduced binocular vision such as depth perception. Utilizing the presently described system, cyclovergence ranges can be measured using methods that are analogous to those used to measure convergence and divergence. For example, a Dove prism may be placed before one eye and rotated in order to rotate an image (or a prism may be placed before each of an individual's two eyes and rotated relative to one another to rotate two images) in a dichoptic display, such as a head-mounted display.

Hardware

An exemplary embodiment of a head-mountable display (HMD) 100 for use in the presently described vision assessment and treatment systems and methods is illustrated in FIGS. 1A-1C. As can be seen therein, the HMD 100 includes a headset 102 including an interior display screen (e.g., an augmented display or a virtual reality display), which can be viewed through eye ports 104. The HMD 100 further includes a lens holder 106 configured to receive and retain insertable lenses 108 (described in detail below).

In implementations, the lens holder 106 enables selective insertion of different types of lenses 108, such as standard trial lenses or custom-made lenses in one or both eyes, including prisms, plus lenses, minus lenses, and/or toric lenses (or lenses having combinations of the foregoing). For example, a first type of lens 108a (e.g., plus lenses) or a second type of lens 108b (e.g., prismatic lenses) can be selectively inserted into each of a left-side receiving portion 110a and a right-side receiving portion 110b of the lens holder 106 in order to perform a specified test or vision assessment procedure. In another example, both of lens 108a and 108b (e.g., plus prismatic lenses, spherical lenses, and/or cylindrical lenses) can be inserted into the lens holder 106 to perform a specified test or visional assessment procedure. In other examples, a single lens (e.g., one of the lenses 108a or 108b inserted into one of the left or right-side receiving portions 110a or 110b) may be inserted in the lens holder 106 for use with a single eye of an individual, or different types of lenses can be inserted for each eye (e.g., one of the lenses 108a inserted into the left-side receiving portion 110a and one of the lenses 108b inserted into the right-side receiving portion 110b).

As illustrated in the embodiment of FIGS. 1A-1C, the left or right-side receiving portions 110a or 110b are joined by a bridge 112. In alternate embodiments, the left or right-side receiving portions can be separate structures (lacking a bridge or other means of connection). In implementations, the lens holder 106 can be formed via 3D printing, injection molding, extrusion, or pressing, and can be comprised of metal, plastic, rubber, or other moldable or printable material. In implementations, the lens holder 106 can be permanently attached to a surface 114 of the headset 102 (e.g., comprising a co-molded or co-printed structure with the surface 114, or adhered to the surface 114). In alternate implementations, the lens holder 106 can be separable or detachable from the surface 114 and include a releasable attachment mechanism (such as, as snap-fit or friction fit mechanism or other mechanism configured to lock the lens holder to the surface). Further, in the illustrated embodiment, the lenses 108 are generally circular or cylindrical and the receiving portions 110 have a complementary structure comprising a half circular/cylindrical shape configured to receive one or more lenses. In alternate implementations, the lenses can have a different shape (e.g., square, cuboid, triangular, triangular prism, etc.) and the receiving portions can have corresponding a complementary structure. Further, in alternate implementations, the lens holder can be configured to encompass a perimeter of a lens.

The lens holder 106 can further include one or more mechanisms for retaining a lens after insertion into the left or right-side receiving portion. In implementations, a lens can be snap-fit or friction-fit into the left or right-side receiving portion. Alternatively or additionally, the lens holder can include a locking mechanism, such as one or more a spring biased arms or slidable tabs configured to contact a portion of the lens and retain its position within the left or right-side receiving portion. Further, alternatively or additionally, the lens holder and the lenses can be configured to be magnetically mated, such via inclusion of magnets (e.g., rare earth magnets) in the lens holder that are configured to attract a magnetic element on the periphery of the lenses, such that a position of the lens is maintained by magnetic force until pulled upon by a user or a clinician to remove the lens. It will be appreciated that other mechanisms and/or mechanical structure can be utilized to attach the lenses to the lens holder.

For example, in an alternate embodiment, the lenses can be mounted in a plate and the headset can include a slot for selective insertion of one or more plates (having lenses disposed therein). In implementations, the lenses can be permanently mounted in various plates, and multiple plates can be inserted in the slot to enable use of the lenses in combination. In other implementations, a single plate can be configured to have multiple lenses mounted therein for each eye, enabling selectable use of the lenses or combinations of lenses.

Further, the lenses can be attached into the HMD 100 in such a way that there is space between the inserted lens and the user's eye (such as, via use of the aforedescribed embodiments including lenses mounted in insertable plates). This can enable the user to additionally wear their own spectacles (glasses) that implement or include their normal refractive correction, thereby making the HMD usable by people with different refractive errors because each user would be able to use their own personal eyewear to have "corrected to normal" vision. For example, a myope who needs −4D lenses to see clearly in the distance and a hyperope who needs +4D lenses to have relaxed accommodation when seeing in the distance would have similar effective vision while wearing their glasses, and thus while using the HMD.

Additionally, the original built-in lens (located at the eye ports 104) of the HMD can be replaced by a new lens that combine the focusing power or vision correction of the new lens with additional new focusing properties of insertable lenses, such as those described herein.

Additionally or alternatively, in embodiments, one or more of the lenses can be worn in spectacles when the HMD is configured to allow sufficient space for the user to wear eye glasses. These spectacles can be standardized for use with any patient in order to effect a specified property, such as e.g., the property of having different regions of the display with different accommodative demands. In implementations, the spectacles can have the lenses permanently mounted therein, or the lenses can be releasably attachable to the spectacle frame enabling attachment of desired lenses. In implementations, the patient can wear a second set of lenses, such as contact lenses or additional prescription eye glasses, if they have refractive error that must be corrected to normal. Alternatively, the spectacles can be built for the user to include their normal corrections for spherical and astigmatic refractive error.

In the foregoing embodiments, lenses for use the HMD 100 can be selected based on their effect on an individual's vision or other specified property. For example, in embodiments, prismatic lenses can be used to extend the range of testable vergence eye postures, which can be useful in patients with strabismus (a condition in which the eyes do not properly align with each other when looking at an object) and can also be useful in creating a constant vergence demand of the stimulus effected by the left eye display and the right eye display of the HMD. In other examples, plus lenses can be used to simulate far viewing, and minus lenses can be used to simulate near viewing, (hereby alternating the accommodative demand in the HMD 100, which would otherwise have a fixed accommodative demand. These lenses may also stimulate or relax accommodation if the HMD includes an augmented display that allow the eyes of the individual to use some or all of their natural accommodative ability. In yet other examples, toric lenses with cylinder and/or positive or negative spherical power can be used to correct the patient's refractive error (e.g., myopia (nearsightedness), hyperopia (farsightedness), presbyopia (loss of near vision with age), and/or astigmatism (a type of refractive error in which the eye does not focus light evenly on the retina)) to improve the focus of the images, which makes the tests/treatments easier for the patient to perform, and can improve the quality of results from vision assessment.

In still other examples, bifocal or n-focal (n>2) can be used with the HMD 100. An exemplary embodiment of bifocal lenses 108c configured for use with the HMD 100 are illustrated in FIGS. 1D-1F. Each lens includes a top portion 116 and a bottom portion 118, where the top portion 116 has one or more properties which differ from the bottom portion 118. In implementations, the lenses 118c include a minus power at the top of the lens and plus power at the bottom of the lens (i.e., a normal configuration for a bifocal lens). In other implementations, the bifocal lenses 118c each include a minus power in the bottom of the lens and a plus power at the top of the lens (i.e., an inverse configuration relative to a normal bifocal lens).

As shown in FIGS. 1E and 1F, an individual wearing the HM D 100 having the lenses 118c attached thereto or otherwise associated therewith (such as e.g., worn in a pair of spectacles in combination with wearing the HMD 100) can have visual stimuli (virtual display elements or targets) displayed to each eye on a virtual or augmented reality display screen 500 (discussed in further detail below) including a right eye-display 502 and a left-eye display 506. In the illustrated example, visual targets or stimuli are displayed within each of the let eye and right eye-displays 502 and 506. Specifically, a first visual stimulus 516 (a circle) and a second visual stimulus 518 (a crescent moon) are shown on the display 500 (in each of the right eye-display 502 and the left eye-display 506). The user can view the first visual stimulus 516 though the top (e.g., plus) portion of the lens, and can view the second visual stimulus 518 through the bottom (e.g., minus) portion of the lens.

When the user looks at the first visual stimulus 516, the plus-power portion of the top portion of the lens can cause a decrease in the accommodative demand of the display as compared to direct viewing of the display without the interposed lens.

It will be appreciated that vergence metrics of many types (such as those discussed above) can be tested with a variety of binocular visual stimuli or visual targets. Either visual targets that are flat (visual targets that do not have a depth component) or visual targets that are stereoscopic (visual targets that induce disparity to an individual's vision and are seen to have depth) can be used for testing. Further, in implementations, the size of the visual target can be manipulated so as to make accurate binocular convergence upon the visual target either easier (faster, more accurate, or across a larger range of vergence demands) by using large targets, or more difficult (slower, less accurate, or across a smaller range of vergence demands) by using small targets. Additionally, visual stimulus parameters (such as, size, complexity, depth, line thickness, etc.) can affect horizontal fusional amplitudes in individuals.

In implementations, the contrast of the target with the background and/or coloration can be manipulated to make binocular tracking using a vergence eye movement either easier (faster, more accurate, or across a larger range of vergence demands) by using high contrast targets, or more difficult (slower, less accurate, or across a smaller range of vergence demands) by using low contrast targets. Optionally, contrast of a binocular target can be different in the left-side and right-side displays. A mismatch in contrast is known to degrade the ability of the binocular system to find matches between the eyes for purposes of computing disparity. The stimuli for creating vergence and accommodative demand can also be varied as to their shape, blur or other spatial or temporal filtering, three-dimensional shape, visual texture, ability to stimulate or attract interest, ability to stimulate or attract attention, etc. In implementations, visual targets that are familiar in appearance to targets used in a clinical setting can be simulated in the virtual visual stimuli. For example, a spot can be presented in one eye and a line in the other eye, which would simulate the appearance of stimuli when using a Bagolini or Maddox lens. Accordingly, in the embodiments and implementations disclosed herein, the visual targets displayed on the display 500 can be manipulated as discussed above (as well as below) to alter the testing parameters.

It will be appreciated that a lens with multiple focal distances placed between the user's eye and the display of the HMD can change the accommodative demand in the headset when the user views the visual targets/stimuli. For example, if a lens has different geographic zones having different powers (such as the top portions 116 and the bottom portions 118 of the lenses 108c), then the accommodative demand changes when the eye views the upper and lower regions of the display through these different zones. The accommodative demand can therefore be dependent on the geographical location of the visual stimulus within the display.

In implementations where the bifocal lenses 108c are a normally configured bifocal lens (i.e., the top portion 116 having a minus power and the bottom portion 118 having a plus power), in order for accommodative demand and vergence demand to agree with each other, the virtual objects or visual targets in the display that have a far simulated viewing distance are positioned in the lower part of the display 500 so as to be seen through the regions of the lenses (i.e., the bottom portions 118) with plus power, and objects in the display 500 that have a near simulated viewing distance are positioned in the upper part of the display 500 so as to be seen through regions of the lenses (i.e., the top portions 116) with minus power. Thus, in this instance, the visual targets 516 are simulated to be closer/nearer, while the visual targets 518 are simulated to be farther away.

Alternatively, in implementations where the bifocal lenses 108c are inversely configured bifocal lens (i.e., the top portion 116 having a plus power and the bottom portion 118 having a minus power), the virtual objects or visual targets in the display that have a far simulated viewing distance are positioned in the upper part of the display 500 so as to be seen through the regions of the lenses (i.e., the top portions 116) with plus power, and objects in the display 500 that have a near simulated viewing distance are positioned in the lower part of the display 500 so as to be seen through regions of the lenses (i.e., the top portions 116) with minus power. Thus, in this latter instance, the visual targets 516 are simulated to be farther away, while the visual targets 518 are simulated to be nearer/closer.

Exemplary embodiments of bifocal and trifocal lenses are schematically illustrated in FIGS. 1G-1I. As can be seen in FIG. 1G, a bifocal lens 108d has an inverse bifocal configuration, such as that described above, where the lens is divided into two vertically aligned halves, and includes a plus power at top portion of the lens and a minus power at the bottom portion of the lens. Alternatively, the portions of the lens can be arranged horizontally or along some other axis. For example, a bifocal lens 108e can be divided into two lateral halves and include a plus power at one side of bifocal lens and a minus portion, such as the configuration shown in FIG. 1H (which has a plus power on a left side portion thereof and a minus power on a right side portion thereof). It will be appreciated that, in implementations of testing and/or training exercises, the laterally divided lens 108e can be utilized in combination with visual targets that simulate far viewing displayed in a left side portion of a display (or in a left side portion of each of a left eye-display and a right eye display), while visual targets to simulate near viewing are displayed in a right side portion of the display (or in a right side portion of each of a left eye-display and a right eye display). In other embodiments, lenses can include more than two portions. For example, a trifocal lens 108f including a plus power at a top portion thereof, an intermediate portion at a center portion thereof, and a minus power at a bottom portion thereof is depicted in FIG. 1I.

It will be appreciated that the inverse bifocal lenses (such as the lens 108d) enable the visual stimuli presented on the display in the HMD to mimic natural vision, where objects that are closer are viewed at a lower portion of the field of view and objects that are farther away are viewed at an upper portion of the field of view. Thus, visual tests or treatments utilizing the inverse bifocal lenses can provide a more comfortable experience to the user/individual by simulating the natural relationship between vergence and accommodation (whereas normal bifocal lenses may be less natural and/or confusing), thereby having the potential to improve accuracy of the test and/or the overall user experience.

In either implementation, the lenses can be used to simulate pencil pushups or tromboning, a therapeutic activity that can be performed in the clinic or at home using the HMD 100, in which the patient views an object at a simulated far distance and it is moved closer until it appears blurred or appears double, then the object is moved to increase its distance until it becomes clear and single, and the activity is repeated. For example, using the HMD 100 in combination with the lenses 108d, the position of the display would change, so as to be seen through additional minus power when the vergence demand is increased.

Further, the lenses 108d can be used to simulate natural viewing in (raining applications. For example, an airplane pilot or ground-vehicle driver typically looks at distant objects through a windshield in alternation with looking at a dashboard or a display panel that is below the windshield within the field of view. Utilizing the inverse bifocal lenses, a pilot or a driver who is receiving training could be made to accommodate far when looking through the simulated windshield in the HMD 100, and to accommodate near when looking down at the display. Because simulated scenes such as airplane cockpits are usually rendered as being stationary in the world across changes to the position of the user's head, this method will work across changes in elevation of the eyes (e.g., the eyes move upward to look at the top portion of the display through the top portion of lenses 108d, and the eyes move downward to look at the bottom portion of the display through the bottom portion of the lenses 108d), but not across changes in the pitch of the head. In some instances, the user could pitch their head to choose which part of the lenses to see through. For example, the user could lean their head backwards to look at the top portion of the display through the bottom portion of the lenses 108d. To prevent the user from looking at both the tar (windshield) and near (dashboard) portions of the display through the same region of the lens, head position can be monitored during the training and a warning or alert give to the individual or an administrator of the test/training. Additionally, the display can be used to assess the user's ability to use split-level displays. For example, it can be determined whether the user has presbyopia, convergence insufficiency, or accommodative insufficiency that limits their ability to look up and down between the windshield and the dashboard.

Furthermore, using the lenses 108c-108f, several different relationships can be established between vergence demand and accommodative demand, depending on the position of the displayed objects within the HMD display. In implementations, vergence and accommodation can be put into positive correlation. For example, viewing of the natural world can be simulated by the use of visual stimuli that demand from the patient, depending where the patient is looking, convergence and accommodation simultaneously, or divergence and relaxed accommodation simultaneously. In other implementations, vergence and accommodation can be put into negative correlation. For example, negative correlation can be used during a treatment that is designed to weaken the coupling between accommodative and convergence responses within the user's vision. In yet other implementations, vergence and accommodation can be made uncorrelated. For example, vergence and accommodation can be uncorrelated by holding either vergence or accommodation fixed while the other is varied, or by varying vergence and accommodation independently of one another.

In additional or alternate implementations, progressive lenses having a gradient or a range of varying powers along a vertical axis of the lens can be utilized with the HMD 100. For example, a standard progressive lens has a gradient of varying powers including a greater plus power at the bottom of the lens than the top of the lens. In this example, when the visual stimuli are positioned to require viewing through the top of the lens (at the top portion of the display in the headset), the refractive power of the lens is low, so that accommodative demand of the stimulus is high, simulating a nearer object, and when the stimulus is positioned toward the bottom of the display in the headset, the refractive power of the lens is high (plus) so that accommodative demand of the stimulus is low, simulating a farther object. Similar to the inverse bifocal lens discussed above, in other exemplary variants, the common gradient for lens power in a progressive lens can be inverted with greater plus power at the top. In this latter example, the accommodative demand of the stimulus is low at the top of the display and simulates a farther object, and when the stimulus is positioned toward the bottom of the display in the headset, accommodative demand of the stimulus is high and simulates a nearer object, thereby enabling the visual stimuli to mimic natural vision, where objects that are closer are viewed at a lower portion of the field of view and objects that are farther away are viewed at an upper portion of the field of view, which may improve accuracy and/or user experience.

In additional or alternate implementations, multifocal lenses, which are designed to provide focus of both distance and near virtual objects, can be utilized with the HMD 100. In such implementations, multiple focal distances can be achieved either simultaneously for viewing through one part of the lens, in which case the virtual image or visual target may have reduced contrast, but can be in focus for more than one accommodative state of the eye. Thus, multifocal lenses can be useful in situations where either of two different accommodative states are acceptable, or when it is desirable that the user be able to see the display clearly using either of two accommodative states. For example, the user may be better able to control accommodation using input to the left eye. In this example, the left eye receiving portion of the lens holder can be fitted with a multifocal lens so that accommodative demand is driven by the right eye, in order to give the user practice at using the right eye to control accommodation.

In additional or alternate implementations, adaptive focus or turntable lenses can be utilized with the HMD 100 to enable a range of accommodative demands. For example, the lenses could be controlled by a motor within or attached to the HMD, which is controlled via a processor executing a program to control the accommodative demand. In one specific example, the Oculus Half Dome VR headset includes a mechanical varifocal display. In other examples, adaptive lenses include electro-optical lenses and opto-mechanical lenses. The power of an electro-optical lens can be changed when the index of refraction of the materials in the lens is adjusted by a change of electrical voltage or current applied to the material of the lens, and the power of an opto-mechanical lens can be changed when a motor adjusts the tension or static position of the lens components so as to change its shape.

In additional or alternate implementations, the HMD can include other mechanical adaptive features. For example, the HMD can include motorized or mechanical structure for adjusting a positon of the screen or lens holder along the z axis to either increase or decrease accommodative demand. In another example, the HMD can include a lightfield display, which is capable of displaying virtual images at many focal distances (and thus at many accommodative demands). A lightfield display can therefore be suitable for accommodative training in which accommodative demand changes gradually as a simulated distance to the virtual objects or visual targets changes. For example, an individual with accommodative insufficiency (AI) may, at the start of training, only be able to clearly see visual targets displayed at distance. A task that requires high resolution (high acuity), and therefore good accommodation by the individual at a specified distance, can be displayed in the lightfield display such that the visual target is moved gradually from far to near to cause accommodative demand for the task to increase slowly.

In additional or alternate implementations, as discussed above, an individual or user can wear contact lenses in combination with the HMD. For example, the user can wear a contact lens (in one or both eyes) of fixed power to change the accommodative demand of the display. In another example, the user can wear an adaptive contact lens (in one or both eyes) for which lens power can be controlled dynamically without removing the lens from the eye, to change the power of the lens as required. For example, a liquid tunable lens, a deformable lens that is controller electrostatically, or a lens in which a gradient of the index of refraction is achieve using liquid crystals can effect such a system in which the power of a lens can be controlled dynamically.

In additional or alternate implementations, the user can wear or use lenses of different powers in (via contact lenses) and/or in front of (via spectacles or inserted lenses) each of the eyes, in which case the accommodative demand can be controlled by changing the strength (contrast, size, intensity) of the visual stimuli on the display presented to one eye as compared to the other. For example, if a normally sighted person with emmetropia (no visual defects) is fitted with a +2D lens before the left eye and a -2D lens before the right eye, the person will relax accommodation by 2D when viewing visual stimuli presented to the left eye alone, and increase accommodation by 2D when viewing visual stimuli presented to the right eye alone. When viewing visual stimuli/targets with both eyes, the accommodative status of the individual's vision may be determined by the eye that sees the content on which the user's selective attention is focused. In another example, within the HMD the accommodative demand without additional lenses may require +0.75D on the part of the observer, and appropriate lenses to achieve a 4D differential between the left and right eyes would be +0.75D lens for the right eye so that accommodative demand becomes OD in the left eye and -3.25D lens for the right eye so that accommodative demand becomes +4D in the right eye.

In additional or alternate implementations, a user may have one or more implanted lenses, such as adaptive focus intraocular lens implants surgically implanted to treat cataracts. The adaptive focus intraocular lenses replace the lenses in each eyes with an artificial lens that can be focused. For example, the dioptric power of the artificial lens may be controlled by the patient's ciliary muscles. The treated individual may initially have accommodative insufficiency after surgery, as a result of low accommodative ability due to presbyopia (farsightedness) prior to the surgery. For such a patient, the HMD can be configured for variable accommodative demand of the visual stimuli on the display that can be used to challenge the patient's ability to accommodate with the new artificial lenses. In this example, the patient must cause the accommodative power of the implanted lens to change, so as to bring the display into focus, thereby compensating for the display's dynamically changing accommodative demand. The HMD can be calibrated to require a defined amount of accommodation to clear a specified visual target (bring the image into focus on the retina). In this manner the user can be trained how to accurately use the implanted lens to focus on the visual stimuli.

Systems

The described techniques can be implemented in any suitable system which can include a device having a display on which images are presented to a patient, a device controlling the presentation of the images on the display, an input device that is controlled by the patient performing a visual activity (e.g., a test, task, etc.) and that is configured to acquire user input from the patient. In embodiments, the same device can include both the display and the input device in a head-mountable device. The head-mountable device can be in the form of glasses having a built-in display, goggles, or other headset-type device. In implementations, a head-mountable virtual reality device can have a virtual reality (VR) display. In other implementations, a head-mountable augmented reality device can have an augmented reality (AR) display.

In other embodiments, one can create a two-distances display using a mobile display device such as mobile phone or computer tablet, and a larger computer or television screen at distance, which can be utilized with the various lenses discussed above. This configuration can for example be used to create displays at two distances for an exercise that requires the user to look back and forth between the displays. For example, in exemplary implementations, software configured for assessment and/or treatment of vergence and accommodation disorders can be provided on a user device, such as on a mobile display device 126 illustrated in FIG. 1J, and a fixed display or dynamic display controlled by software on a more distant user device 128 (such as a TV or PC Monitor). The two devices can be networked so that they can communicate in real time and the viewer can provide user input that affects the visual targets displayed on the screens of both devices 126 and 128. The nearer device 126 uses a camera 130 facing the distal device 128 to take a picture of a calibration image 132 of known size, such as QR sticker image, ChArUco pattern, ArUco pattern or other marking, that is configured to enable the mobile device 126 to calibrate to a distance 134 between the mobile device 126 and the distal display 128. In variants, the calibration image 132 may be displayed on the distal display device 128, or may be provided in a hard copy form and attached to the distal display device 128, such as, for example, printed onto a piece of paper and taped to the distal display device. Utilizing the calibration image 132, the mobile device 126 can compute the distance to the distal display device 128. Utilizing a camera 136 on the mobile device 126 that faces the user, a distance 138 between the mobile device 126 and the head 140 of the user can be determined. For example, the true interpupillary distance of the user in cm can be inputted into the mobile device, and the distance between the images of the two pupils used to determine the distance from the mobile device to the camera by means of triangulation. Further, the mobile device can instruct the user to adjust the distance between the mobile device and the user, or between the mobile device and the distal display, to desired values of distance to create desired accommodative demands for the two displays. The mobile device can be held by the user. The user can fixate the two displays in alternation to alternate between distance and near accommodative demands. Optionally, lenses 108 can be utilized with the display devices 126 and 128.

Regardless of the implementation of the display system, the described embodiments can acquire user input, such as in the form of verbal cues/responses, an input device (via e.g., a press of one or more buttons), or other mechanism of user input. Further, in implementations user input can be acquired via tracking of movements of head and/or eyes of the user wearing a head-mountable device via built-in head-tracking and/or eye-tracking sensors. In other implementations, external cameras track movement of the head of a patient, for example when the patient is using a monitor or phone instead of a head-mountable device. Electroencephalogram (EEG) signals, and any other types of signals, can be acquired as well via corresponding sensors. Thus, various sensors can be used to acquire information as the user/patient is performing a test in accordance with the described techniques.

In implementations, the user (e.g., the patient) can view a device's display (e.g., a display of a virtual reality device, an augmented reality device, a smartphone, personal computer, tablet, smart watch, etc.) and user input can be acquired either via an input mechanism that is part of that device (e.g., a touch button, touchscreen display) and/or via a separate input device, such as a computer mouse, a joystick, keyboard, another hand-held controller, etc. The user input can be received via one or more of a gesture and motion tracking device (which can recognize movements and gestures of user's hand, arm, other body parts, the entire body, etc.), a microphone that receives audible/voice input from the user, at least one camera, an omnidirectional treadmill, and/or a game pad. In implementations, user input can be received via a head tracking sensor, a face tracking sensor, a hand tracking sensor, a body tracking sensor, a voice recognition sensor, a heart rate sensor, a skin capacitance sensor, an electrocardiogram sensor, a brain activity sensor, a geolocation sensor, at least one retinal camera, a balance tracking sensor, a body temperature sensor, a blood pressure monitor, and/or a respiratory rate monitor.

Furthermore, a computing device used by the patient to perform activities (e.g., assessment tests or treatment tasks) in accordance with the described techniques can be associated with eye tracking or other sensors monitoring the eyes (or the entire face) of the patient as the patient is performing the activity. For example, a smart TV or another device can have real-time eye tracking sensor(s) such that eyes of a viewer are monitored, which can be utilized in conjunction with the technique described herein. A smartphone or a personal computer can similarly have built-in eye tracking technology which can be utilized in addition to (or instead of, depending on the implementation) user input acquired using various devices controlled by the user. In addition, in some embodiments, values of various parameters of the head-tracking device or another device used by the patient are monitored. For example, images can be obtained to determine whether camera lenses are in a proper condition, etc. In some cases wearing glasses inside the HMD can interfere with the proper functioning of eye tracking devices inside the headset. To solve this problem, the lens holder can be manufactured to hold the lenses inside the headset so that the viewer's glasses are not required during the test. Alternatively, a custom insert may be made to order and sent for a particular user's prescription, or the user/patient can wear their personal contact lenses. Further, in some examples, the sensors and/or the cameras inside the HMD can be adjusted such that wearing personal spectacles does not interfere with tracking the user responses.

Figure 2A:
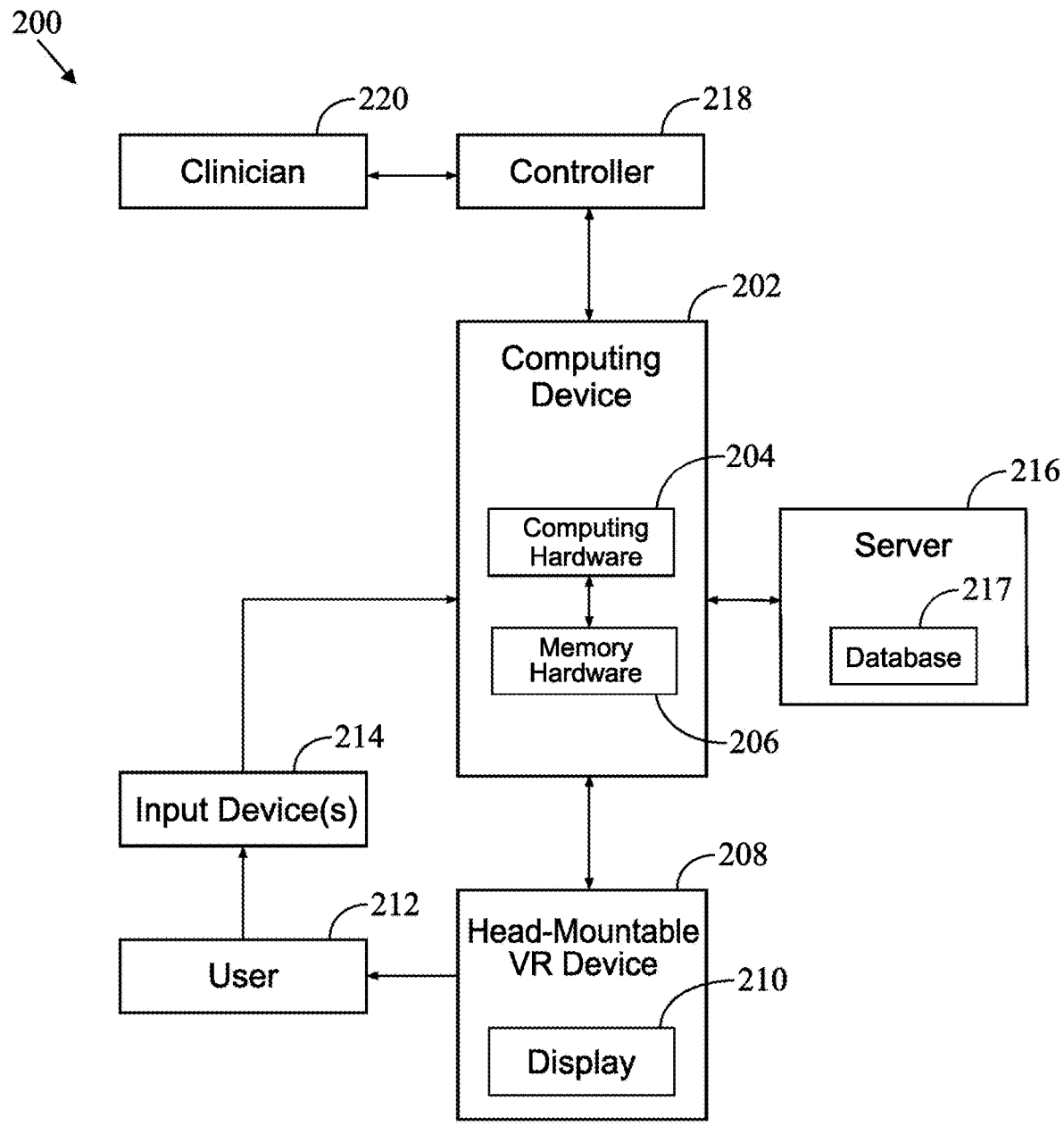
FIG. 2A is a logical block diagram illustrating an exemplary system in which embodiments described herein can be implemented.

FIG. 2A illustrates one embodiment of a system 200 which can be configured to perform a process of assessing and/or treating vergence and accommodation disorders of a user 212, such as, for example, a method 400 shown in of FIG. 4 (discussed below) and/or other methods/processes in accordance with the described techniques (such as those shown and described with respect to FIGS. 5A-5M). The user 212 can be one of a plurality of various patients e.g., seniors, adults, or children of various visual abilities. As depicted in FIG. 2A, the system 200 includes a computing device 202 having computing hardware 204 and memory hardware 206 coupled to the computing hardware 204. In this example, the system 200 also includes a head-mountable virtual reality (VR) device 208 configured to communicate with the computing device 202 and having a display 210 configured to display virtual reality (VR) environment to the user 212 wearing the VR device 208 such that the VR environment is viewed by the user. In implementations, the VR device 208 can have the configurations described above with respect to the HMD 100.

As shown in FIG. 2A, the system 200 can also include one or more input devices 214 configured to acquire user input based on active input received from user 212 and/or based on passively acquired sensor data (e.g., head tracking and/or eye tracking sensor(s)). Information acquired by the one or more input devices 214 can be transmitted to the computing device 202.

Also shown in FIG. 2A, the computer system 200 can include or it can communicate via a remote connection with a server 216 which can include one or more databases 217 stored on one or more memory hardware and configured to store information acquired by the computing device 202 and other computing devices or to provide information to the computer system 200, such as testing/training image data. The information, at least in part, can also be stored in the memory hardware 206 of the computing device. The server can automatically process data that can be accessed from devices communicating with it. In implementations, the server can coordinate communication between the clinician and the user.

As further shown in FIG. 2A, the computer system 200 can also include a controller 218, such as, for example, a touch display coupled to the computing device 202 and configured to receive input from a clinician 220 or other type of input for controlling operation of the computing device 202 and the VR device 208 in connection with diagnosing, assessing or treating a vision disorder afflicting the user 212. In some implementations, the controller 218 can be part of the computing device 202. However, in other implementations, the controller 218 can be or can be included in a remote computing device (e.g., a clinician's computing device).

The computing device 202 can be a suitable computing device, such as a desktop or laptop personal computer, a personal digital assistant (PDA), a smart mobile phone, a server, or other suitable computing device that can be operated by a user and/or can present services to a user. As mentioned above, the computing device 202 includes the computing hardware 204 and the memory hardware 206. Computer-executable instructions implementing the techniques described herein can be encoded on the memory hardware 206, which can include a hard disk drive, a Compact Disk (CD) or a Digital Versatile Disk (DVD), a persistent or non-persistent solid-state memory hardware (e.g., Flash memory, Magnetic RAM, etc.), or another suitable memory hardware. The memory hardware has at least one physical property that is altered in some way during a process of recording data thereon. For example, a magnetization state of a portion of a physical structure of a computer-readable medium may be altered during a recording process.

In implementations, the computing device 202 can be coupled to the head-mountable VR device 208 via a wired or wireless connection. Similarly, the computing device 202 can be coupled to the controller 218 via a wired or wireless connection.

The head-mountable VR device 208 can be a suitable wearable device configured to provide a virtual reality, augmented reality, mixed reality, holographic reality space, or similar environment to the user 212 of that device 208. For clarity of presentation, examples herein may refer to VR or virtual reality: however, an augmented reality, mixed reality, holographic reality space or similar environment may be used for the disclosed examples and embodiments, and when applying the disclosed techniques and methods. The VR device 208 can include computing hardware, a visual interface (such as the display 210 and/or another display), and memory hardware for storing computer-executable instructions for execution by the computing hardware. In implementations, portions of the display of the VR device 208 can be transparent, semi-transparent, or opaque, or the VR device 208 can be a holographic computing device having a see-through holographic display. For example, the VR device can be a HoloLens device developed by Microsoft Corporation. The VR device can be in the form of smart glasses or it can have other configuration (a goggles or helmet-type VR device).

The display 210 of the VR device 208 can display a different image to each eye of the user, thereby providing the user a sense of depth and 3D vision. The VR device 208 can be configured to use a head tracking technology such that the device 208 acquires and transmits to the computing device 202, and/or to another computing device, information about the position, tilt, and/or rotation of the head of the user 212. The display 210 can also be configured to implement eye tracking technology, which allows the VR device 208 to acquire information about the position, xy location, rotation, pupil size indicating pupil dilation of the user's eyes, state of a variable lens, and/or other information that can be acquired by tracking user's eyes.

The VR device 208 can be configured to provide a VR visual environment that gives a user a more realistic feeling of being part of such environment and a larger field of view where an accurate control of the image being shown to each eye can be achieved. Furthermore, when a user is wearing the head-mountable VR device 208, brightness can be a more controllable parameter since the VR device 208 itself provides a source of light to the displayed images. Other parameters of the displayed images are also controllable, thereby allowing generating of consistent results, which can be particularly advantageous for reproducibility of the assessment and/or treatment activities/tasks performed by the user and comparison of performance results for the same user or along multiple tests.

As mentioned above, the VR device 208 can acquire and transmit to the computing device 202 input in the form of information or data related to a user's eye movements and/or a user's head movements. The user input can also be acquired based on the user's using one or more input devices 214 communicatively coupled to the computing device 202. Non-limiting examples of the input device 214 include a mouse, keyboard, gesture % motion tracking device, microphone, camera(s), omnidirectional treadmill, game pad, body temperature monitor, pulse rate monitor, blood pressure monitor, respiratory rate monitor, electroencephalography device, or any other device.

The computing device 202 and the VR device 208 can be used in a home setting or other environment outside of a medical facility. Thus, the computing device 202 coupled to the VR device 208 can be controlled by the user 212 operating the devices. It should be understood that, if the user 212 is a young child or an adult who needs assistance with operating the devices, a parent or other caregiver can assist such user.

In some implementations, the computing device 202 and the VR device 208 can be employed in a clinical setting, such as in a medical facility. In such scenarios, operation of the computing device 202 can be controlled via the controller 218 which can be, e.g. a touchscreen device coupled to the computing device 202 and operated by a clinician 220. The touchscreen device can mirror images visible to the user 212 via the VR display 210 (e.g., images for the left and right eyes of the user 212) and it can be configured so as to receive input for controlling the virtual environment images displayed on the VR display 210. The controller 218 can be a monitor or a computing device similar to the computing device 202, or any other device. Regardless of the particular type of the controller 218, a display associated with the controller 218 can be used to control in real time, as the user 212 is wearing the VR device 208, the virtual environment provided to the user 212.

In some aspects, the controller 218 can communicate with the computing device 202 wirelessly over a computing network including wireless communication medium or media for exchanging data between two or more computers, such as the Internet. The controller 218 can thus be located at any location assessable via the computing network, including a location geographically remote from a location of the computing device 202. Thus, a user equipped with the computing device 202, such as a mobile phone (e.g., a smartphone or any hand-held computing device which can be a convergent device encompassing capabilities of multiple devices), and a suitable VR device 208 (which can be a low-cost headset as known in the art or developed in the future) can be located remotely from a clinician operating the controller 218 to control via the computing device 202 the virtual environment of the user. This telemedicine technique can simplify, decrease costs of, and make more accessible early diagnosis and timely treatment of many vision disorders. Because communication between trained medical professionals and patients is simplified and fewer or no hospital visits can be required, more patients can receive access to proper treatment of vision problems. The telemedicine approach can be particularly advantageous for persons living in rural, remote locations where such persons would otherwise have limited access to adequate vision care.

As shown in FIG. 2A, the computing device 202 can communicate with the server 216 over a communication network, such as the Internet. The server 216 can act as a central repository of data relating to vision treatment platforms (e.g., a platform performing the processes of FIG. 4 or other processes in accordance with the embodiments disclosed herein) executable on a plurality of computing devices (including the computing device 202). Data relating to all measurements and/or treatments conducted using the described techniques, including timing data, can be recorded and stored on the database 217 in the server 216, which can be one or more databases. The user or clinician can then view a complete history of the visual performance of the patient. The data stored on the server 216 can be accessible to the user via a computing device, such as the computing device 202 or another device, in a manner that allows the user to sort and analyze the historical data in various ways, view various statistics derived from the data, compare that user's performance to the performance of other users (e.g., based on averages generated from all of the users, or other parameters). The results of the analysis and comparison can be presented to the user or other person (e.g., a clinician) in visual formats that facilitate understanding of the results. The user can be enabled to customize the manner of the representation of the results.

Figure 2B:
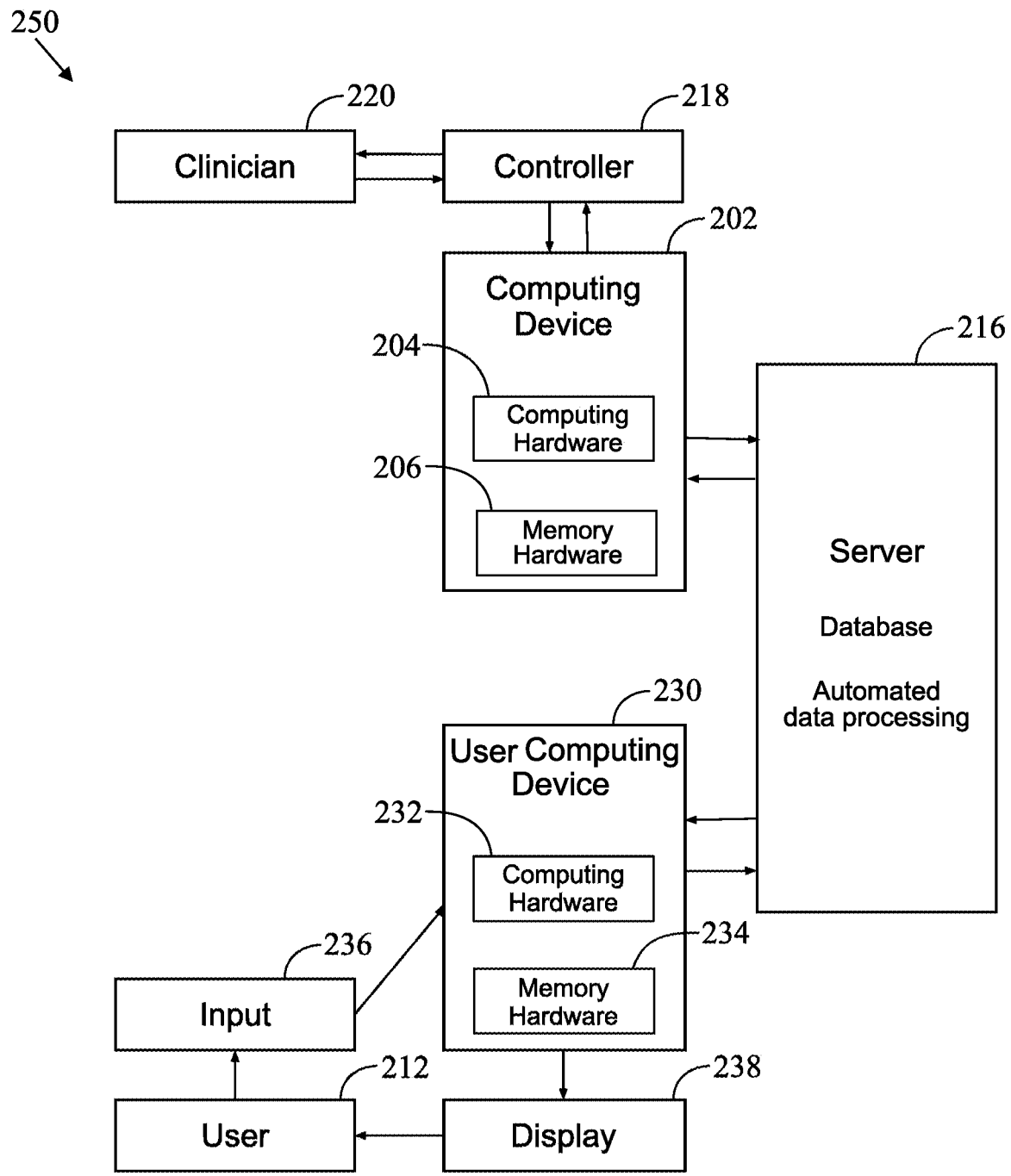
FIG. 2B is a logical block diagram illustrating another exemplary system in which embodiments described herein can be implemented.

It will be appreciated that the system 200 is shown to have the VR device 208 by way of example only. FIG. 2B illustrates another exemplary embodiment of a system 250, in which the head-mountable VR device 208 may be excluded. In such embodiments, visual information can be displayed for view by a patient on a user computing device 230 (e.g., a smartphone, a personal computer, etc.) and user input 236 can be acquired in various manners. As shown in FIG. 2B, the user computing device 230 can communicate with the server 216 over a communication network, such as the Internet, in a similar manner as computing device 202 and an include the functions described above with respect to computing device 202.

Also shown in FIG. 2B, the user computing device 230 including computing hardware 232 and memory hardware 234, and which has or is associated with a display 238, can be used to implement the described techniques. For example, visual stimuli or targets can be rendered on a user interface of a display 238 of a smart phone, a personal computer, tablet, TV, smart watch, etc. Thus, in some embodiments, a display of a computing device other than a head-mountable device is configured to be viewed by the user 212. Furthermore, in some embodiments, more than one user input device can be used—e.g., a head-mountable VR device 208 and a hand-held user computing device 230. In some cases, visual information can be displayed and user input can be acquired for testing purposes such that position and movements of the entire user's body can be monitored, which may or may not be done in combination with one or more other input devices.

Each of the exemplary systems in accordance with embodiments disclosed herein can be configured to accept user input indicating detection or visualization of a visual target. In systems including a head-mountable device, because the head-mountable device is used to display targets in a virtual reality environment rendered by a display, a test or a treatment (or other activity) does not require patient comfort to be compromised. For example, the test does not require a patient to hold still, sit up straight for a certain duration of time, and to keep her or his head still (either with or without a specific head-immobilizing support such as a chin rest). Young, weak, disabled, and/or elderly patients can have difficulty maintaining necessary physical position relative to an existing system, and many may thus be unable to complete testing and/or treatment for vision disorders. The use of the head-mountable device in embodiments described herein eliminates a need for immobile, bulky, and costly equipment, while decreasing discomfort experienced by some patients. The head-mountable device is typically of a smaller size, more portable, and less costly than existing devices and systems. The head-mountable device can be used in conjunction with a variety of input devices. For example, monitored user input can include head, hand, other body part or entire body, eye tracking, etc. In some cases, sensors can be attached to the user's body (e.g., head or another part) and user input in an objective form can be received.

Further, the described techniques can involve displaying information on other types of displays such as, for example, computer monitors, smart phones, and TV monitors. Various types of user input devices can be utilized. Furthermore, the described system can utilize statistical methods to determine assessment and/or treatment data/results, estimate the likelihood that results are indicative of a disease, and/or monitor progression of the disease over any time period (e.g., days, weeks, months, or years). The testing and other activities can be performed either with or without eye tracking, as well as other response methods. The activities can be implemented for screening for diseases, disorders, or aging, which can affect vergence and accommodation. Information acquired when each patient is being tested can be stored in a suitable location. A Bayesian or another approach can be used to analyze the collected data.

In some embodiments, the head-mountable device can be Oculus Rift™ Samsung Gear™, and HTC Vive™, or other head-mountable device. The head-mountable device can be configured such that it can be worn by a patient for a relatively long period of time, without causing patient discomfort. The head-mountable device can be configured to be used for a patient at home, such as no or minimal (e.g., via a telemedicine platform, or any other communication manner) supervision by a medical professional is required. Also, a headset is configured to be mounted to a patient, so that the patient does not have to keep his/her head stationary (e.g., in an uncomfortable chin/forehead rest, as in some conventional set-ups for visional assessment and treatment). Moreover, the headset can be worn by the patient while the patient is sitting, standing, or lying down, without compromising performance of tests using the headset.

The headset can have built-in eye (racking sensors. Furthermore, in some embodiments, various other techniques can be used to determine whether targets have been properly seen or identified by the patient. Non-limiting examples of such techniques include electroencephalogram (EEG) and measurement of pupil size/response. In some embodiments, electroretinography (ERG) can be used to determine if patient's photoreceptors and ganglion cells are responding to light hitting the retina. Furthermore, it will be appreciated that, in embodiments, user input can be detected to determine whether the patient was able to see a visual target. For example, the user input can include an input received from eye tracking sensor, an eye pointer, or another device.

Targets can be presented in a way that encourages patients to naturally look at the targets when they appear. Because, as mentioned above, user input is acquired indicating a target's visual identification, occurrences of false positives are reduced. Furthermore, administration of instructions to the patient and monitoring the patient's performance can be automated, physicians can monitor their patients' visual tests remotely, new tests can be evaluated, and visual targets can be presented to either (or both) eyes on a given trial. For example, images presented on a display viewed by a patient undergoing a visual assessment test can be presented to one or both of the patient's left and right eyes. In implementations, one of the eyes can be tested without the patient being aware that this particular eye is being tested. Additionally, data acquired during each test can be stored for subsequent analysis.

The test parameters can be selected manually, e.g., via suitable user interface configured to receive input from a user such as a health care professional, or the test parameters can be selected, at least in part, automatically. For example, the test parameters can be selected, prior to or during the test, automatically, which can be done based on various factors, such as patient-specific characteristics (e.g., age, gender, anatomical characteristics, medical conditions(s), etc.) and historical information on the patient's prior performance of the test.

During a test, a user interface of a computing device can display information related to the test and performance of the test by the patient. The information can include, for example, information on the current status of the test, as well as options to pause, start, or modify one or more parameters related to the test. Once the test is completed, results of the test can be rendered on the user interface.

Test results can be presented to a user (e.g., a healthcare professional) in any suitable format, such as an electronic format—i.e., on a display of the computing device, in a video, audio, or a combination thereof format. In some embodiments, test results include patient information, medical history information, and test session information. The patient information can include, for example, patient's name, date of birth, medical record number, gender, and/or any other suitable information. The medical history information can include, for example, clinical diagnoses (e.g., a prior diagnosis by a healthcare professional), diagnosis code number(s), and/or any other suitable information. The test session information can include, for example, date and time of test, test strategy, test diagnosis if available, test duration, visualization of targets success (if applicable), name and address of a person supervising the test, departmental logo, reference to a test website, and/or any other suitable information. Regardless of the specific format in which the test results are provided, the results and any other related information (e.g., patient-specific information) can be handled and stored in conformance with requirements for electronic protected health information. Thus, the information is handled and stored in compliance with the Health Insurance Portability and Accountability Act (HIPAA).

Image Correction

It will be appreciated that in the systems and methods disclosed herein for adjusting the accommodative demand of a visual display, the lenses (such as lenses 108) utilized in combination with a head-mountable display (such as HMD 100) or other display system may cause a change in visual directions of objects that are not seen through the center of the lens, according to Prentice's rule (i.e., Prism (diopters) =Power (diopters)×Decentration (centimeters)). Seeing through a non-central part of the lens occurs when the line of sight to the object being viewed passes through a non-central part of the lens. This situation can occur if (1) the eye is not centered behind the lens, for example if the patient's interpupillary distance is different from the interpupillary distance between two lenses being used with a display device, or (2) the object has an eccentric location relative to the eye's primary visual axis within the head, or if both (1) and (2) occur. In the case of a lens that is centered on the line of sight during primary gaze (primary gaze is when the eye is looking straight ahead relative to the head), a magnifying (plus) lens increases the eccentricity at which an object is seen, while a minifying (minus) lens decreases the eccentricity at which an object is seen. Therefore, a near object that is directly in front of the head will be seen through non-central parts of the two eyes' lenses. As a result, the vergence demand of a near object seen through minus lenses is less than that for natural viewing, and the vergence demand of a near object seen through plus lenses is greater than that for natural viewing.

An exemplary formula characterizing the error that occurs in vergence demand is vm, where v is the original vergence demand and m is the magnification caused by the lens. For thick lenses, m depends on the vertex distance between the eye surface and the lens insert, on the dioptric power of the lens, and on the shape factor of the lens which depends in turn on its form and thickness. A typical magnification values for lenses with a power of −4D is 0.94, with a power of −8D is 0.89, and with a power of +4D is 1.09. The visual direction (eccentricity) of an incoming ray, seen through the lens, as measured relative to straight ahead, is m times the angle of the visual direction (eccentricity) of the original ray. Therefore, looking through two eye-centered lenses, each with magnification m, at a near object with vergence demand v can, if the lens is not compensated for by a change of display size, have a vergence demand of vm when seen through the two lenses (assuming the lenses are each centered in front of one of the eyes). For example, an object that is 20 cm directly in front of the head has a vergence demand of 17 degrees, assuming an interpupillary distance of 6 cm. To simulate an optical distance of 20 cm, a lens of power −5+0.75=−4.25D would be used, which would have a magnification m =approximately 0.94. As a result, the uncorrected vergence demand would be approximately (0.94)(17 deg)=16 deg. To simulate an optical distance of 11 cm, a lens of power −9+0.75=−8.25D would be used, resulting in m=approximately 0.89, and vergence demand would be reduced from 33.4 deg to 29.7 deg.

The methods and systems disclosed herein can be configured to compensate for the foregoing potential issues with the lenses by scaling and displacing the visual targets. In implementations, the power of the lens may be taken into account when generating the virtual images/targets, so as to prevent distortion of the vergence demand of the visual stimulus. For example, when using minus lenses, the actual positions of the visual targets within the left and right-side displays (such as the right eye and left eye displays 502 and 506) can be adjusted by a specified or calculated amount that counteracts the effect of the lenses. An exemplary method for doing so is to magnify the images by the same amount as the minification of a minus lens, or to minify the images by the same amount as the magnification of a plus lens. In addition, the locations of the images for each eye can be adjusted to compensate for a mismatch between the interpupillary distance of the user and/or the interpupillary distance of the device. Further, scaling and displacing of the visual targets can be done separately for different parts of the image that are viewed through different parts of the lens. For example, when a bifocal or trifocal lens having plus power at the top of the lens and minus power at the bottom of the lens is utilized with the HMD (or other visual assessment and/or treatment display system), the scaling and displacing of a top portion of a visual target (or a first visual target displayed at a top portion of the display) can be varied relative to scaling and displacing of a bottom portion of the target (or a second visual target displayed at a bottom portion of the display). In other words, the top portion of the image (or the first visual target displayed at the top portion of the display) can be minified by the same amount as the magnification of the plus portion of lens, and the bottom portion of the image (or the second visual target displayed at the bottom portion of the display) can be magnified by the same amount as the minification of the minus portion of the lens.

The aforedescribed exemplary systems 200 and 250 can be programmed to perform the foregoing image compensation procedures in order to improve accuracy of the assessment and/or treatment techniques relative to systems which lack image compensation. For example, FIGS. 3A-3D illustrate exemplary testing/training scenarios where a display is viewed through spherical lenses, without image compensation, and FIGS. 3E-3H illustrate exemplary testing/training scenarios where a display is viewed with image compensation. As can be seen therein, without image correction (as in FIG. 3A-3D), an actual visual direction (illustrated in solid lines) that is at an angle relative to a center line of the lens does not align with an intended visual direction (illustrated in dotted lines), whereas, when image correction is applied (as in FIG. 3E-3I), the actual visual direction is closely aligned with or equal to the intended visual direction.

Figure 3A:
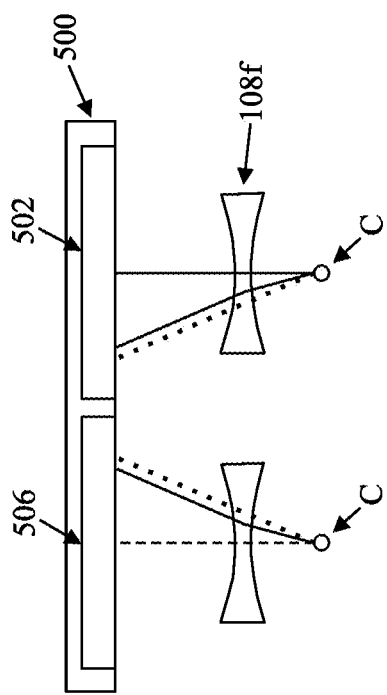
FIGS. 3A-3D are schematic illustrations of exemplary testing/training configurations utilizing lenses in combination with a display system in accordance with embodiments described herein, wherein no image correction is applied.
Figure 3B:
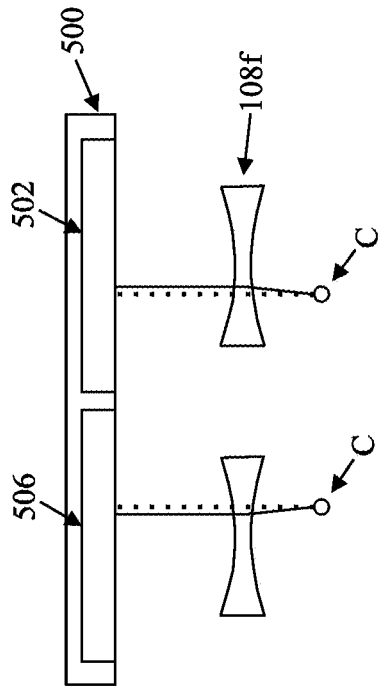
Figure 3C:
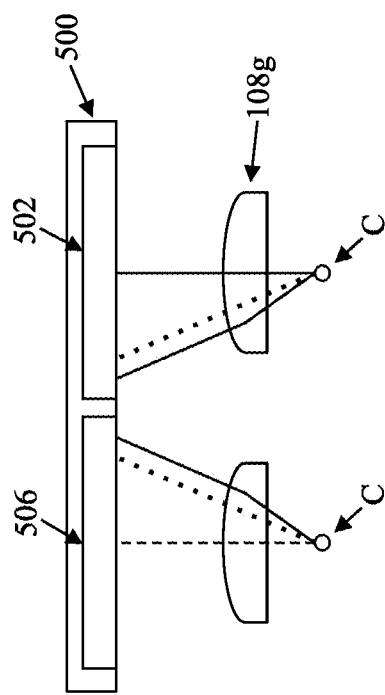
Figure 3D:
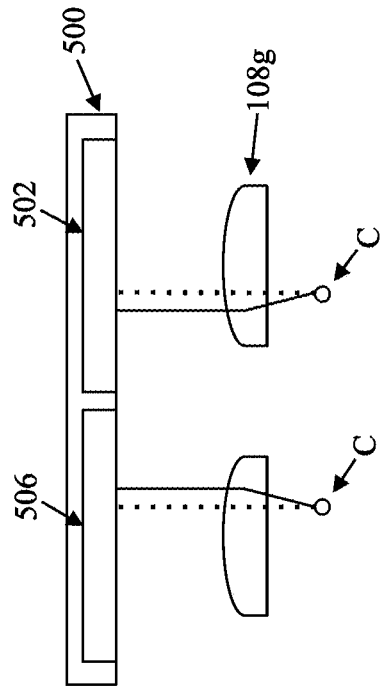

Specifically, in FIG. 3A, lenses 108*f* having a minus power (or a region with a minus power) are each aligned with an optical center C of each eye of the user, and the actual rays seen and/or actual directions of view (solid lines) are offset relative to the intended visual direction (dotted lines) as the user views an eccentric object on the display 500. In this example, rays along the center line (dashed line) are unaffected by the shape of the lens, but non-central rays (which correspond to the dotted lines representing the intended visual direction) appear to come from a location that is closer to a center line of the lens than is intended, as described by Prentice's Rule, which quantifies the prismatic displacement of an image as a function of a lens's power and an entering ray's distance from the center of the lens. This distortion can reduce the vergence demand for simulated near objects in the display, and can also cause minification of the images. In FIG. 3B, lenses 108*f* having a minus power (or a region with a minus power) are mis-aligned with an optical center C of each eye of the user because of an interpupillary mismatch, and the actual rays seen and/or actual directions of view (solid lines) are offset relative to the intended visual direction (dotted lines) as the user views an object at a central region of the display 500. In FIG. 3C, lenses 108*g* having a plus power (or a region with a plus power) are aligned with an optical center C of each eye of the user, and the actual rays seen and/or actual directions of view (solid lines) are offset relative to the intended visual direction (dotted lines) as the user views an eccentric object on the display 500. In this example, rays along the center line (dashed line) are unatTected by the shape of the lens, but the non-central rays appear to come from a location that is further from the center of the lens than intended according to Prentice's Rule (discussed above). In FIG. 3D, lenses 108*f* having a plus power (or a region with a plus power) are mis-aligned with an optical center C of each eye of the user because of an interpupillary mismatch, and the actual rays seen and/or actual directions of view (solid lines) are offset relative to the intended visual direction (dotted lines) as the user views an object at a central region of the display 500.

In the respectively corresponding scenarios illustrated FIGS. 3E-3H, the aforedescribed image correction is applied to compensate for lens characteristics and/or interpupillary mismatch. Specifically, in FIG. 3E, lenses 108*f* having a minus power (or a region with a minus power) are each aligned with an optical center C of each eye of the user, and image correction (magnification) is applied during the generation of the visual targets such that the actual rays seen and/or actual directions of view (solid lines) are generally aligned with the intended visual direction (dotted lines) as the image eccentric object viewed by the user on the display 500. In FIG. 3F, lenses 108*f* having a minus power (or a region with a minus power) are mis-aligned with an optical center C of each eye of the user because of an interpupillary mismatch, and image correction (magnification and displacement) is applied during the generation of the visual targets such that the actual rays seen and/or actual directions of view (solid lines) are generally aligned with the intended visual direction (dotted lines) as the user views an object at a central region of the display 500. In FIG. 3G, lenses 108*g* having a plus power (or a region with a plus power) are aligned with an optical center C of each eye of the user, and image correction (minification) is applied during the generation of the visual targets such that the actual rays seen and/or actual directions of view (solid lines) are generally aligned with the intended visual direction (dotted lines) as the image eccentric object viewed by the user on the display 500. In FIG. 3H, lenses 108*f* having a plus power (or a region with a plus power) are mis-aligned with an optical center C of each eye of the user because of an interpupillary mismatch, and image correction (minification and displacement) is applied during the generation of the visual targets such that the actual rays seen and/or actual directions of view (solid lines) are generally aligned with the intended visual direction (dotted lines) as the user views an object at a central region of the display 500. In some examples, an optical lens or lenses to collimate light or approximately collimate light can be used in combination with the minus or plus lenses.

Methods

In embodiments, using the systems described above, a 3D display (or other multi-distance display system) can be used to generate a visual target that moves in three dimensions. By tracking the temporal dynamics with which the accommodative and vergence responses of the observer/user track the targets, and comparing these test measurements to standardized values (such as e.g., simulated optimal vision or average measurements taken in people with normal vision), deficits in accommodation and/or vergence of the user can be assessed and/or diagnosed. For example, in implementations, accommodative demand can be varied using a physical object that is viewed by the user by changing the viewing distance from the viewing distance from the user to the physical object (such as e.g., for use with an augmented reality display), or by using a display capable of adjusting accommodative demand of virtual objects. In other exemplary implementations, vergence demand can be varied by changing the viewing distance to a physical object, or by using a simulated object in an HMD. In another exemplary implementations, the presently described systems and methods can be used to generate and vary both accommodative and vergence demand of physical or virtual objects.

The system and methods/procedures can be configured to measure or quantify accommodation and vergence and/or to provide practice (training) to a user in order to improve the amplitude (in diopters for accommodation, or in degrees for vergence), or temporal characteristics, of the response.

Figure 4:
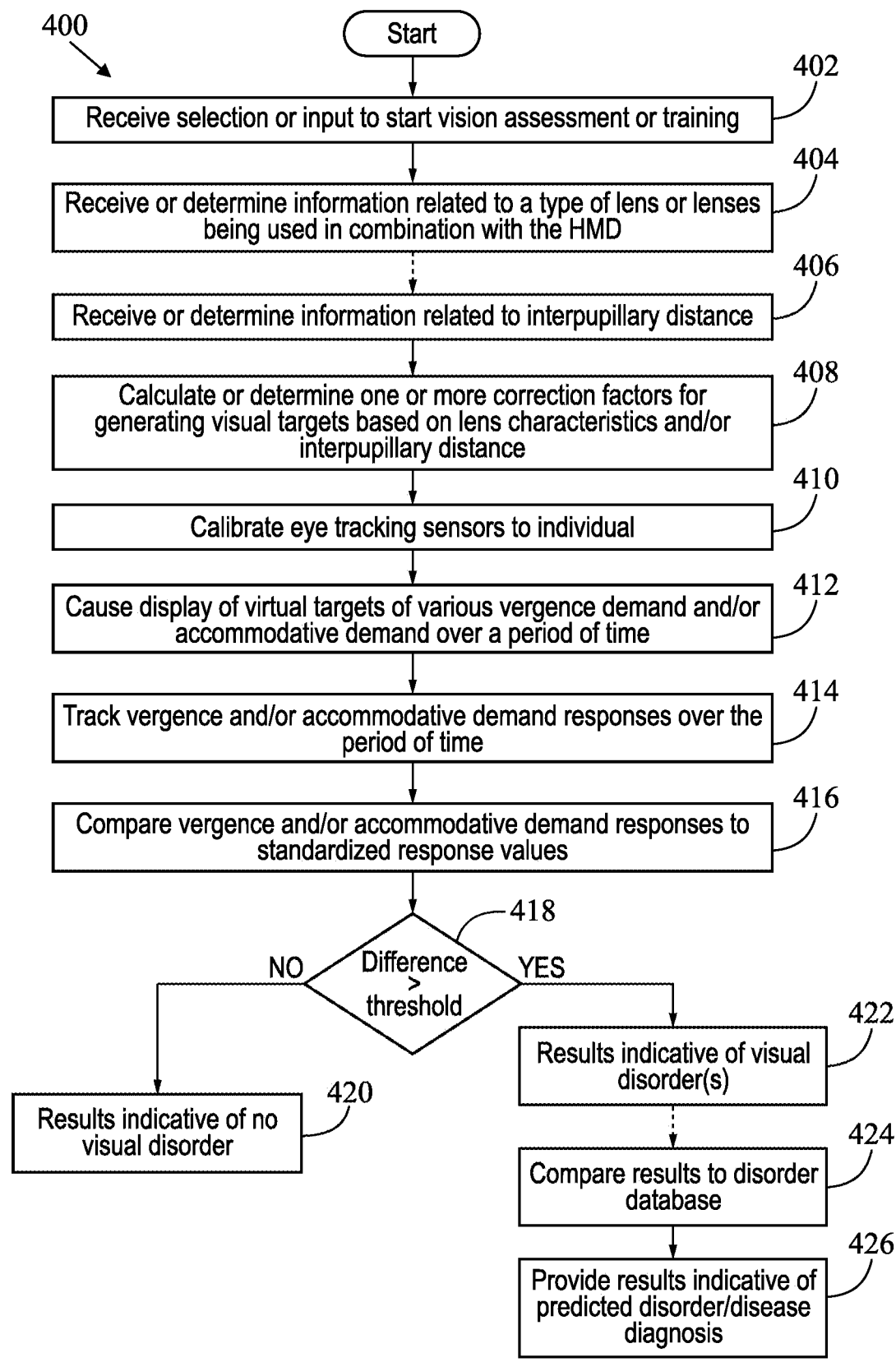
FIG. 4 is a logical flow diagram of an exemplary method in accordance with embodiments of the present disclosure.

An exemplary embodiment of a generalized method 400, which can be implemented as computerized steps configured to be executed by one or more processors for performing visual assessment (and/or training) utilizing the devices and systems disclosed herein, is shown in FIG. 4. As depicted therein, at step 402, to initialize testing and/or training, the system can receive a selection from a user or clinician to start the testing or training. In implementations, the system can be pre-programmed with a specific sequence of selected exercises. In other implementations, the system can receive a selection of a specific test or training exercise chosen by a user or a clinician. Exemplary tests and/or exercises for phoria, vergence disorders, and accommodation disorders are described below with reference to FIGS. 5A-5M. It will be appreciated the system can be configured to run a plurality of additional tests and/or exercises, or that the test and exercises can be modified as desired for a specific user or a class of users. For example, conceptually similar tests or training exercises for phoria, vergence disorders, and/or accommodation can be generated for a child user and an adult user; however, the child's test can include child-friendly images (e.g., animals), while the adult test utilizes different images (e.g., letters, symbols, etc.). In another example, a specialized test or exercise can be generated for a user that has color blindness or other vision impairments that may affect the user's ability to perform the test/exercise.

At step 404, the system is configured to receive or determine information related to characteristics of or a type of lens or lenses that are in use with the HMD 100 (or other display system). In implementations, the system can be configured to receive input related to characteristics of or a type of lens from a clinician or a user via a graphical user interface (GUI) or other user input device. In alternate or additional implementations, the system can be configured to read an identifier (such as an RFID tag, an optical marker, or other machine readable marker or code) that identifies the characteristics of or the type of lens. For example, the identifier be utilized to indicate a configuration of the lens, such as a bifocal, trifocal, or progressive lens, an orientation of the different powered potions of the lens (e.g., horizontally or vertically arranged), a power of each portion of the lens, and/or other lens characteristics. In some examples, an optical reader or an RFID reader is installed in the HMD such that lenses can be identified upon insertion therein or attachment thereto. In other examples, the system can include a separate reader that can scan the identifier on the lenses (or on the lens holder, or on the frame of eye glasses) prior to their association with the HMD. In some examples, the memory can store a look up table for various lens characteristics and an associated identifier. In alternate or additional implementations, the HMD can be configured to determine the lens characteristics, such as via a camera or other device installed in the HMD that can identify a curvature, a thickness, or other characteristics of the lens.

Optionally, at step 406 the system can be further configured to receive or determine information related to an interpupillary distance of the user. In implementations, the system can be configured to receive input related to the interpupillary distance from a clinician or a user via a GUI or other user input device. In other implementations, the system can be configured to determine the interpupillary distance of the user. For example, an interpupillary distance can be determined by using images from one or more eye tracking cameras placed at known positions within the HMD in order to calculate the positions of the eyes relative to the cameras. In some examples, collecting information related to interpupillary distance can be excluded from the method, such as when only one eye of a user is being tested and/or treated.

The data or information related to the characteristics of or the type of lens or lenses and/or the interpupillary distance can be utilized to calculate or determine any image correction factors (such as, minification, magnification, scaling, and/or displacement discussed above) that compensate for or limit effect of the lenses on the images viewed by the user (step 408). As discussed above, an exemplary method for doing so is to magnify the images by the same amount as the minification of a minus lens, or to minify the images by the same amount as the magnification of a plus lens. Further, the locations of the images for each eye can be adjusted to compensate for a mismatch between the interpupillary distance of the user and/or the interpupillary distance of the device. Furthermore, scaling and displacing factors for the visual targets can be calculated for different parts of the image (or different locations on the display where the image may appear) that are viewed through different parts of the lens.

Per step 410, eye tracking sensors within the HMD can be calibrated to the user wearing the headset. In implementations, in order to measure vergence eye posture, one or more eye trackers (such as e.g., cameras) can be spatially calibrated one eye at a time. For example, in a person who has strabismus or phoria, each eye may be able to reliably fixate a visual target when the other eye is occluded, even if simultaneous fixation of the visual target by both eyes is not reliable. In these cases, each eye can be calibrated separately, because one eye may be oriented in a direction that is controlled, or partially controlled, by the strabismus or phoria. During the calibration procedure, objects can be displayed to one eye only, and the user can be asked to look at each object in turn, or induced to fixate on each object in turn by performing a visual task. An exemplary visual task that can induce fixation includes moving one or more moveable simulated object to coincide visually with one or more stationary simulated object. The moveable and stationary objects can be spatially separated within the display, for example in a 3×3 array of nine objects, or some other square, rectangular, or other-shaped array, with more or fewer objects, where the objects can be spaced in a lattice with e.g., 30 degrees spacing or other spacing. An eye-tracking sensor or camera records position data or an image of the eye for each object so that eye position can later be estimated from sensor data or camera images. After each eye has been individually calibrated, vergence eye posture can be computed accurately during binocular viewing. In alternate implementations, the eye trackers can be calibrated to both eyes simultaneously.

After calculation of any correction factors and calibration of the eye tracking, at step 412, the system can cause display of the virtual targets for the specified test or training exercise, such as those illustrated in FIGS. 5A-5M. In each test or training exercise, the system can be configured to track or record, over a period of time (such as, e.g., one second, ten seconds, or one minute) accommodative responses and/or a vergence responses of the user (in step 414). For example, accommodation velocity and vergence velocity can be measured by moving a 3D target through various depths over time. A sinusoidal modulation in depth for the target can be utilized, to measure a response amplitude and phase lag at a particular temporal frequency of modulation for simulated distance of the visual target. The visual target can be small, for example a single point subtending less than 0.5 degrees in diameter, or of a larger size, for example subtending many degrees. Further, the visual target may have a visual pattern that changes in scale with changes in distance to the target, or that changes in scale according to some other relationship to distance. For example, the texture can have elements that subtend a fixed visual angle when the accommodative or vergence demand of the target changes.

As discussed above, the system can measure accommodative amplitude, facility, and/or accuracy, which can be defined independently of overall refractive state or ability as amplitude can be measured while a person is wearing prescribed ophthalmic lenses that allow them to see clearly at near or far distances. Further, the ratio of accommodative convergence to the unit of accommodation (ACA ratio) can be an index of the degree of accommodative convergence, and the ratio of convergence accommodation to the unit of convergence (CAC ratio) can be an index of the degree of convergence accommodation.

Also discussed above, in order to assess vergence ability, a patient's vision can be put under stress (vergence demand) via the system, and vergence ability can be measured by testing vergence ability independently or by testing the vergence ability while the individual is accommodating. In implementations, an individual's ability to converge and diverge can be measured or otherwise determined by measuring e.g., vergence facility, vergence accuracy, vergence fatigue, fixation stability, and/or fixation disparity. The starting point of these activities may be zero stress but may also be adjusted to the level at which the individual can start the activity. In implementations, the amount of stress (or vergence demand) the individual's vision can tolerate is measured in degrees of visual angle or prism diopters and is performed by progressively increasing vergence stress via the vision assessment system. As the vergence stress is increased, the user's vergence eye posture will adapt so as to minimize the absolute retinal disparity of the images. The amount of vergence demand the individual can withstand prior to deterioration of an images appearance (i.e., an image becoming apparently blurry or diplopic) can be recorded. The vergence demand can then be reduced from this breakpoint until the individual is able to regain a clear, apparently single view of the image. In implementations, the ability of an individual's vision to withstand vergence demand can be tested with both horizontal (near and/or far) and vertical stressors. A near, far, or vertical breakpoint can be measured by adding (respectively) progressive near, far, or vertical demand to the visual stimulus on a single or repeated basis until the eyes are no longer able to maintain fusion, at which point they will relax to a more habitual posture. The breakpoint is the maximum vergence demand that the vision of the individual is able to withstand.

In implementations, a proxy signal (or surrogate signal) for accommodation is the size of the pupil. Typically, when a person accommodates near, their pupils also constricts. Therefore the presence of an accommodative response can be assessed by measuring pupil size. For example, a camera pointed at the eyes can create an image of the pupil that is monitored automatically by software that measures the size of the pupil or a degree of pupil constriction. In other examples, accommodation response can also be determined by measuring changes in refraction by using, for example, an autorefractor, a phoropter, or loose lenses. In yet other examples, optical biometry, ultrasound, and/or photographic techniques can also be used. In implementations, vergence responses are measured by eye trackers to determine a position or orientation of one or more eyes while viewing near and/or far visual stimuli.

In other implementations, user input can be collected that is indicative of vergence and/or accommodation responses. For example, a user can indicate that an image changes from blurred to clear (or vice versa) or that an image changes from a single image to a duplicate image (or vice versa) via a user input, such as a verbal cue (which can be recorded and/or automatically interpreted by voice recognition integrated into the system or a separate device in communication with the system), a press of a button, movement that can be detected by a motion sensor, and/or other user input. In another example, the user can provide a rating as to the appearance of elements within the display, such as providing an estimate of the size of a blurred image, the apparent fuzziness of an image compared to a fiducial display, or the apparent separation between two monocularly displayed objects. In another example, a target of a defined shape and size can moved progressively closer to the user, and the user may input a response when the target becomes blurred or distorted (signifying the user's limit of accommodative demand). Similarly, a target may be progressively moved closer to the user, and the user may report when and if the target becomes doubled (signifying the user's limit of vergence demand). Further, temporal dynamics of the foregoing exemplary responses can be tracked and recorded (e.g., a time required for the user to make vergence and/or accommodation response based on the provided responses).

Per step 416, the tracked responses can be compared to standardized values, such as simulated optimal accommodation and vergence responses or average values for accommodation and vergence responses recorded from a plurality of individuals with known healthy vision. In examples, the standardized value can be a distance range at which a person with healthy vision should be able to accommodate or converge/diverge. In additional or alternative examples, the standardized values can be related to a temporal characteristic of the response, such as a time required to accommodate at a specified distance when the viewer switches from viewing a far visual target to viewing a near visual target, or a time required to converge when the viewer switches from viewing a far visual target to viewing a near visual target. In other examples, a number of cycles of an exercise that can be completed within a specified time period may be determined.

In one specific example for measurement and/or assessment of accommodative facility, a user's ability to accommodate can be measured by the number of cycles of alternating accommodation and relaxation responses that the user is able to complete within one minute. The user may be asked to make an image presented to one eye appear clear, as the accommodative demand in that eye is changed from −2D to +2D and back, relative to a starting demand of +2.5D (simulated distance of 40 cm). After the image appears clear, the accommodative demand can be switched, causing the image to appear blurred again, which stimulates a new accommodative response. In this example, a healthy accommodative response may be eleven cycles of alternation or more per minute.

In another specific example for measurement and/or assessment of vergence facility, a user's horizontal vergence ability can be measured by the number of cycles of alternating horizontal convergence and horizontal divergence eye movements that the user is able to complete within one minute. The user may be asked to make two images (one displayed to the left eye and one displayed to the right eye) appear a single image, as the vergence demand is changed from 12Δ BO to 3Δ BI and back, relative to a starting demand of +2.5D (corresponding to a simulated distance of 40 cm). After the two images appear as a single image, the vergence demand is switched, causing the two images to appear double again, which stimulates a new vergence response. In this example, a healthy vergence response may be twelve cycles of alternation or more per minute.

Per step 418, it is determined whether the response value (or a difference between the response value and the standard value) is greater or less than a predetermined threshold. With respect to the foregoing exemplary standardized values, it may be determined that a difference between a time required for the user to accommodate and the standard value is greater than a threshold value (which can indicate that the user is capable accommodation at a normal distance, but the response is slower than in normal healthy vision), and/or it may be determined that a difference between a distance at which the user can accommodate and the standard value is greater than a threshold (which can indicate that the user cannot accommodate at a distance at which a person with healthy vision can accommodate). With further respect to the foregoing exemplary standardized values, it may be determined that a difference between a time required for the user to make a horizontal or vertical vergence eye movement and the standard value is greater than a threshold value (which can indicate that the user is capable vergence at a typical vergence demand, but the response is slower than in normal healthy vision), and/or it may be determined that a difference between a vergence demand at which the user can converge and the standard value is greater than a threshold (which can indicate that the user cannot converge at a vergence demand at which a person with healthy vision can converge). In alternate or additional implementations, the standardized values can be a range of acceptable response values, and it can be determined whether a value for the vergence and/or accommodation response falls outside of the acceptable range, or the standardized values themselves can be a threshold value, and it can be determined whether a value for the vergence and/or accommodation response falls below (or above) the threshold. For example, the standardized values can be a threshold number of vergence or accommodation cycles that are performed within a specified time period, and a response value that this less than the threshold number of cycles may be indicative of visual disorder.

In alternate or additional implementations, a method for measuring a user's ability to accommodate, or to make horizontal vergence eye movements, vertical vergence eye movements, or cyclovergence eye movements, can be to characterize a frequency response the user's visual system. To do this, the accommodative or vergence demand of the stimulus can be varied over time, and the corresponding response can be quantified by a gain (i.e., an amplitude of the response relative to the amplitude of the stimulus modulation) and a lag (i.e., a temporal offset of the response). For example, the accommodative or vergence demand can be varied over time in a sinusoidal pattern at a fixed temporal frequency. The temporal frequency can then be changed from one test (or one visual stimulus) to the next, so that the frequency responses (gain and lag) can be plotted as a function of temporal frequency. The different temporal frequencies can be varied continuously in a frequency sweep, for example changing over time from 0.25 cycles per second to 4 cycles per second, over the course of 60 seconds. Alternatively, the frequencies can be presented by varying the accommodative or vergence demand according to a waveform that includes many different frequency components that change over time, for example a random walk sequence, a pseudo-random walk sequence, or a pseudo-random binary sequence, such as an m-sequence, that is designed to contain desired representative frequency components.

If the difference between the measured value and the standard value is less than the threshold (or the response otherwise acceptable, such as e.g., within an acceptable range or above a threshold for a number of cycles within a specified time period—depending on the implementation of the decision at step 418), then the system can provide a result or output indicating that no visual disorder is associated with the accommodation and/or vergence response at step 420. Alternatively, if the difference between the measured value and the standard value is greater than the threshold (or the response otherwise unacceptable, such as e.g., being outside an acceptable range or less than a threshold for a number of cycles within a specified time period —depending on the implementation of the decision at step 418), the system can provide a result or output indicating that a visual disorder is associated with the accommodation and/or vergence response at step 422. In implementations, the result or output can be provide to a user or clinician in a graphical user interface (GUI) or other computerized device or output device. Further, in implementations, the accuracy of a vergence and/or accommodative response can be optionally signaled to the user by a tone or other feedback signal (e.g., auditory, visual, or tactile), in order to help the user be aware how the response compares to a standard or adequate or normed response while they are wearing the HM D.

Furthermore, in implementations, the results of specific test or a battery of tests for a user can be optionally compared to values in a diagnostic database (step 424). For example, the results can be compared to a look up table of known ranges or values that are indicative to specific disorders. If a match is found between the results and values in the look up table, a predicted disorder and/or disease diagnosis can be provided, such as via display on the GUI (step 426).

In alternate embodiments, the foregoing generalized method can include fewer or additional steps, or the steps can be adapted to for a specified purpose. For example, the foregoing method can be adapted for vision training (without vision assessment). In such an example, the training/treatment can be similar to steps 402-412. In other examples, the method can be adapted for assessment and/or training for specific vision disorders or impairments, such as phoria, vergence disorders, and/or accommodative disorders. Specific examples for assessment and treatment are discussed below with reference to FIGS. 5A-5M.

Phoria Testing and Treatment

In embodiments, the methods and systems disclosed herein can be configured for phoria testing and/or treatment. A phoria is a latent (hidden) eye deviation characterized by a misalignment of the eyes that only appears when binocular viewing is broken and the two eyes are no longer looking at the same object. For example, the eyes appear to be straight, but when covering an eye and breaking fusion, the eyes assume a position away from normal alignment. The misalignment of the eyes may appear when a person is tired, and therefore it is not present all of the time. A subjective cover test can be used in the presently described system to identify a phoria in a patient/user.

In embodiments, to perform a subjective cover test, display elements that are visible in different parts of the images for the left and right eyes, can be used to assess the physical posture of one eye relative to the other. The apparent visual direction of the object in each eye can be determined by its location on the retina in the respective eyes. Normally, the left and right eyes have corresponding retinal points for the purpose of perceived visual directions of visible objects. Therefore, the 2D position of the monocularly visible display elements can be adjusted through control of their (x,y) positions in the display (or equivalently, elevation, azimuth) so as to achieve a perceptual match in position (horizontally, vertically, or rotationally for torsion) of a marker visible to the left eye with a marker visible to the right eye. Assuming a particular pattern of retinal correspondence, for example normal retinal correspondence, the setting that appears to be perceptually aligned will quantify any fixation disparity. A sequence of these settings thus allows dynamic monitoring for the measurement of phoria, strabismus angle (i.e., angle of deviation) in individuals with normal retinal correspondence or abnormal retinal correspondence, and motor fusion ranges (i.e., break and recover points). The visual target can be a near stimulus or a distance stimulus, and the test can be performed with different amounts of spherical correction. e.g. minus lenses to simulate a near target optically. Further, the test allows automation of the change in phoric posture over time, and allows automated responding by the user so that, unlike watching the user's eyes or having them read a number from a ruler (such as from Thorington cards or Howell cards), the test can be done without close supervision by the clinician.

In this context, visual stimuli can be used that reveal the alignment of the eyes without creating a strong stimulus to fusion. Exemplary implementations are illustrated in FIGS. 5A to 5D. As shown in FIGS. 5A to 5D, in exemplary scenarios 510a-510d the display can include a textured background field, such as a stone or crumpled paper texture, or alternatively the walls in a room (as illustrated in FIG. 5F), can be used as a stimulus to fusion; monocular elements can be of dissimilar size and shape in the case of an instruction to adjust their positions to have similar apparent visual direction. The use of dissimilar shapes, such as a spot in one eye and a line in the other, reduces the tendency of the monocular test elements to be a stimulus for motor fusion in their own right.

Figure 5A:
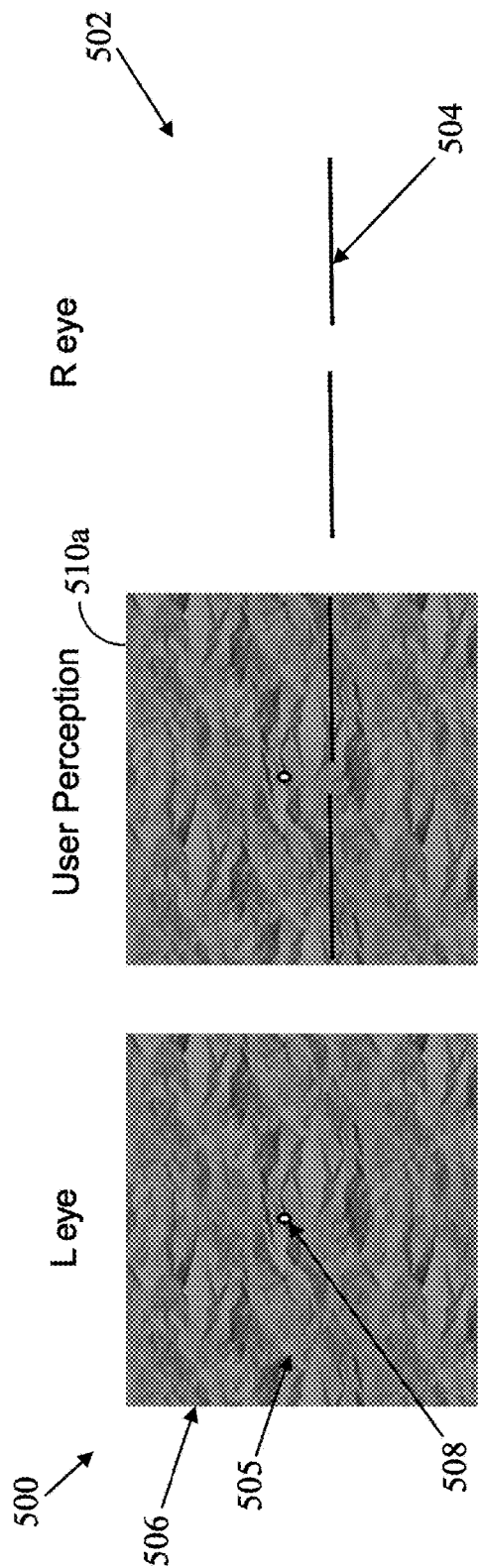
Figure 5B:
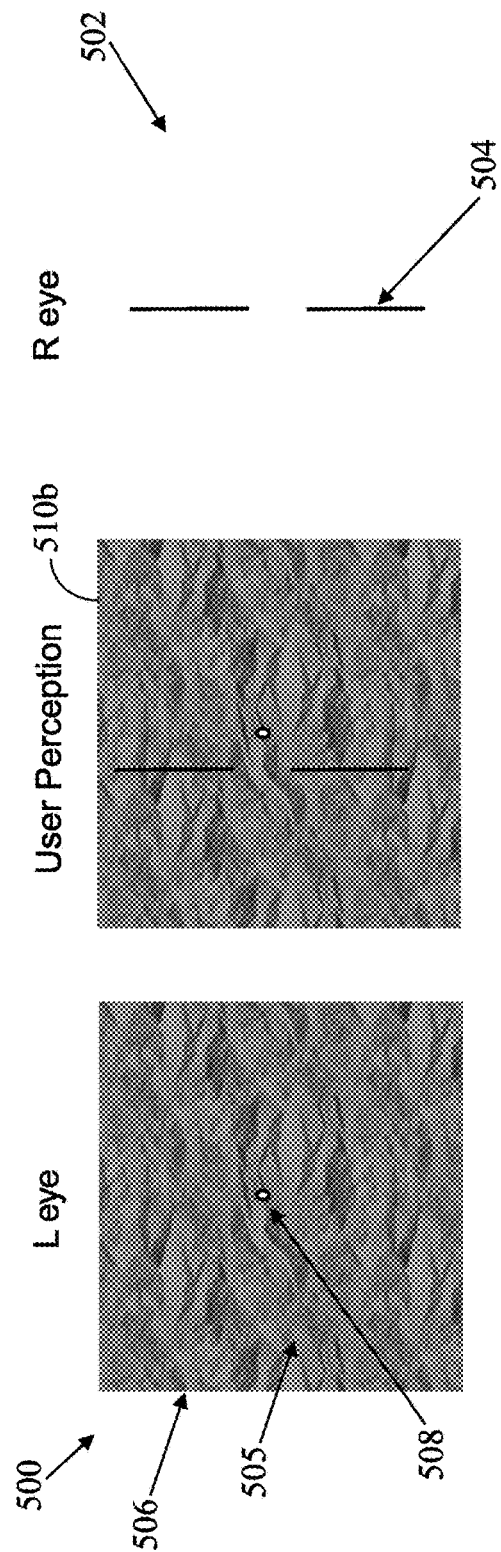
Figure 5G:
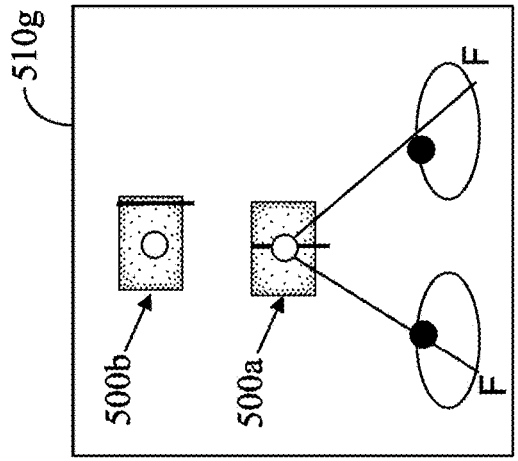
FIGS. 5E-5I are schematic representations of exemplary testing/training scenarios for phoria in accordance with embodiments of the present disclosure.
Figure 5I:
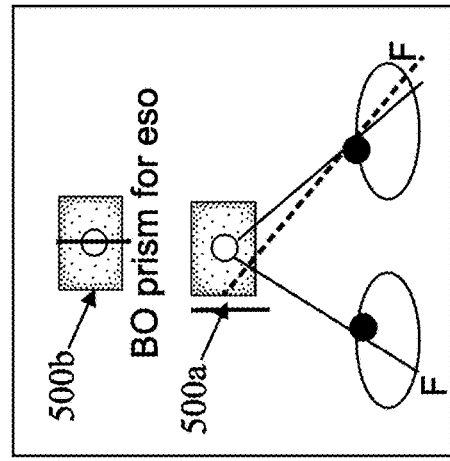
Figure 5F:
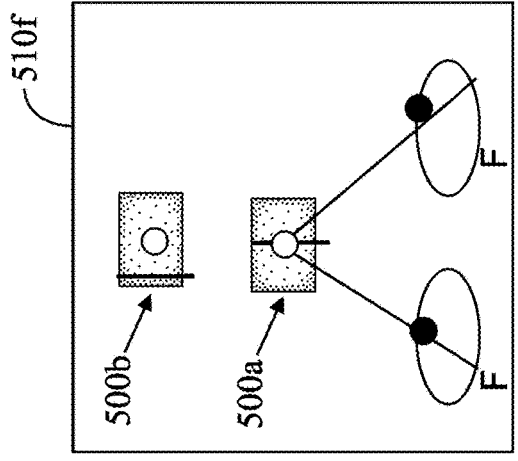
Figure 5H:
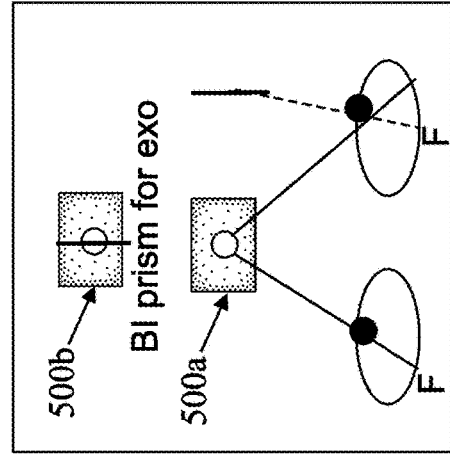
Figure 5E:
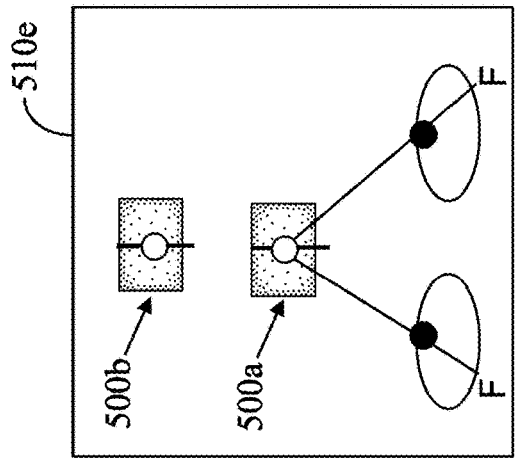

Specifically, in the scenarios 510a and 510b shown in FIGS. 5A and 5B (respectively), the display 500 can be untextured in a right eye-display 502 including a first visual stimulus 504 (a broken line) and include a virtual textured background 505 in a left eye-display 506 including a second visual stimulus 508 (a spot) in order to create a dissociated stimulus, i.e., a stimulus in which there are no binocularly visible elements to control the user's vergence eye posture. In the exemplary scenario 510a, the first visual stimulus 504 is in a horizontal orientation for vertical alignment estimation, and in the exemplary scenario 510b, the first visual stimulus 504 is displayed in a vertical orientation for horizontal alignment estimation. In both examples, in the combined (binocular) perception of the user (shown between the right eye-display 502 and the left eye-display 506), the second visual stimulus 508 is generally aligned by the user so as to coincide perceptually with the first visual stimulus 504, such as the spot being generally centered with the gap in the broken line. The difference in the physical positions of the stimuli in the left eye display and the right eye display, after the user has made this adjustment, is a measurement of the amount by which the eyes are misaligned, as a result of the corresponding points on the retinas of the two eyes have similar apparent visual directions.

Alternatively, in the scenarios 510c and 510d shown in FIGS. 5C and 5D (respectively), both of the right eye display 502 and the left eye-display 506 can include the virtual textured background 505. Further, the first and second visual stimuli 504 and 508 can have a different configuration, such as a solid horizontal line in the right eye-display and a solid horizontal line with a spot disposed beneath in the left eye-display, and the user may be asked to adjust the relative rotations of the left eye image and the right eye image until the two lines appear to be parallel to each other, in order to measure cyclovergence. Cyclovergence can also be measured using a display in which there is no textured background in one eye, and horizontal vergence can be measured using a display in which there are textured backgrounds in both eyes.

In implementations, a textured background displayed to both eyes can enable the user to more easily fuse the scene, due to the similarities in each eye. The first visual stimulus displayed to one eye and the second visual stimulus displayed to the other, while altering the prismatic adjustment in the scene, can enable measurement of an associated phoria and/or prism tolerance of the user. Conversely, showing a textured background to one eye and an empty scene to the other eye, as illustrated in FIGS. 5A and 5B, can be dissociating, thereby giving the user a task of aligning the visual stimuli in the dissociated environment and enabling measurement of the user's dissociated phoria or tropia. In other words, a similarly textured background in the display for both eyes (as shown in FIGS. 5C and 5D), creates a vergence demand, which may allow the user to make a vergence eye movement resulting from perceptual fusion of the background. Under these conditions, the stimulus is "associated" and the measurement of the eye's vergence posture (or deviation) is an "associated" measurement. Alternatively, if there is no background texture in one eye (as shown in FIGS. 5A and 5B), or if the backgrounds cannot be fused or do not give rise to a measurable binocular disparity, then the displays do not create any vergence demand, so the eyes tend to adopt a natural (or phoric) eye posture. Under these conditions, the stimulus is "dissociated" and the measurement is a "dissociated" measurement. When using an associated stimulus, the relative positions of the first and second visual stimuli (e.g., the spot and line), after the user has adjusted them to appear coincident or collinear or parallel, can be used measure the difference between the vergence demand of the stimulus and the vergence eye posture of the user. This difference or deviation can be measured for different vergence demands. The vergence demand can be held constant at a single value while measuring the deviation, or alternatively the vergence demand can be varied over time, with the user's task being, for example, to track the line by trying to keep the dot superimposed on it perceptually. When using a dissociated stimulus, the deviation can be measured for different values of accommodative demand, or for different values of starting vergence demand before the background is removed in one eye.

It will be appreciated that the visual stimuli illustrate in FIGS. 5A-5D are merely exemplary, and are generated to be similar in appearance to the visual images seen during the Maddox rod test insofar as a spot is seen by one eye, and a linear element is seen by the other eye. The Maddox rod test specifically utilizes a spot and an unbroken line. In the tests disclosed herein, the visual stimuli can be either an unbroken line or a broken line with a central or non-central gap. The gap eliminates the presence of binocularly visible elements at corresponding locations in the two eye displays, that could otherwise be fused when viewed by the user (note that a spot in one eye can be fused with a vertical line in the other eye by making a horizontal vergence eye movement, and a spot in one eye can be fused with a horizontal line in the other eye by making a vertical vergence eye movement). In other examples, the visual stimulus displayed as a line with a gap (as illustrated in the first visual stimulus 504 in FIGS. 5A, 5B, and 5D) can alternatively be replaced by a solid line. In such examples, the solid line displayed to one eye and the spot displayed the other eye can have different contrast polarity relative to the background, to prevent the line and the spot from acting as a stimulus that creates a horizontal or vertical vergence demand.

It will be appreciated that in each of the exemplary scenarios 510a-510d shown in FIGS. SA to SI), dissimilar images are displayed to the two eyes, so there is no binocular response to converge on a common scene element presented to both eyes. As a result, the eyes assume the phoric or tropic posture for the given distance as specified by accommodative and pictorial cues. In other implementations, methods of phoria measurement can include displaying a single element or point in space at a fixed distance for one eye of the user to fixate on. For example, the tested eye can blurred or intentionally distorted and shown a vertical line. The user can adjust their vision to move the location of the line in such a way that the horizontal line overlaps a point in space. This example describes a measurement of horizontal alignment, and use of a horizontal line that moves up/down would enable measurement of vertical alignment.

The test measurement itself relies on the principle of crossed and uncrossed disparity. When measuring horizontal eye positioning with one eye fixating on the spot, the linear element is projected onto a non-foveal point of the retina. Patients with an eso posture (uncrossed) will perceive the visual stimuli as being uncrossed, while exo posture (crossed) leads to a perception the visual stimuli being crossed. Similar for a hyper deviation (one eye directed higher than the other), a horizontal line is perceived as being below the spot, while a hypo deviation (one eye directed lower than the other) of the non-fixating eye leads to the horizontal line as perceived as being above the spot.

An exemplary schematic representations of various testing scenarios for crossed (exo) and uncrossed (eso) disparities is illustrated in FIGS. 5E-5I. In each of the scenarios 510e-510i shown therein, the spot (i.e., the second visual stimulus 508) is shown only to the left eye (i.e., displayed in the left eye-display 506) and the line (i.e., the first visual stimulus 504) is shown only to the right eye (i.e., displayed in the right eye-display 502). Further, within each of the scenarios 510e-510i, the actual combined display 500a is illustrated below the corresponding perceived binocular display 500b. In testing scenario 510e, orthotropia (an absence of strabismus) requires no introduction of adjusting prism, because the fixating (left) eye's image of background and spot and right eye's image of the line both fall on the fovea (F) of each eye. The binocular percept of a line intersecting the spot then occurs. In testing scenario 510f, exo deviations will initially cause the user to perceive the line as being in an off-center position (leftward) relative to the spot. The spot falls on the fovea of the fixating eye but a non-foveal point on the temporal retina, which corresponds to a point nasal to the spot's location in space. In testing scenario 510g, eso deviations will initially cause the user to perceive the line as being in an off-center position (rightward) relative to the spot. The spot falls on the fovea of the fixating eye but a non-foveal point on the nasal retina, which corresponds to a point temporal to the spot's location in space.

Testing scenarios 510h and 510i illustrate how the introduction of a real or simulated prism causes the perception of the spot and line to become aligned. As discussed above, no adjustment is needed to match the spot-line location for orthotropia (bottom-left) because both the spot and the line fall on corresponding foveal points. Scenario 510h shows an adjustment for the exo deviations shown in scenario 510f, where a base-in (BI) prism can be used to move the line to an apparent location that matches the rotational location of the spot. Scenario 510i shows an adjustment for the eso deviations shown in scenario 510g, where a base-out prism (BO) is utilized to move the line to an apparent location that matches the spot. The amount of real or simulated prism needed to cause perceptual alignment is a measure of the phoria's sign (exo or eso) and magnitude (in degrees of visual angle of misalignment).

These adjustment tasks performed by the user can be characterized as "nulling" tasks. The user adjusts the positions of the monocular elements (for example, the movement of the line and the dot in the case of vertical or horizontal deviation measurement, or the rotation of the two lines for cyclodeviation), thereby taking a vergence eye posture (under an assumption that stimulating corresponding points on the two retinas causes the stimulating objects to have the same apparent visual direction). It is noted that there are rare conditions in individuals for whom this assumption may not hold, such as in individuals with exotropia or eccentric fixation.

It will be appreciated that foregoing tests can be utilized to measure either associated phoria or dissociated phoria. An associated phoria is a vergence eye posture that is measured when both eyes are open and viewing a similar pattern. Thus, when measuring associated phoria, if the eyes remain misaligned by a significant amount, for example 3 degrees of visual angle or more, the patient may be diagnosed as having a strabismus. Presence of dissociated phoria in the absence of significant associated phoria can be used to diagnose the presence of a strong phoria or intermittent strabismus.

It will be further appreciated that the ability of the systems disclosed herein to measure phoria can be assessed by having the user adjust the positions of monocularly visible elements (such as visual stimuli 504 and 508) to make them appear in a specific orientation (such as coincident, collinear, or parallel) while a displacing prism is installed between the eye and the display within the HMD. For example, first, a baseline vertical measurement can be made without any interposed prism. Subsequently, a second measurement is made when a base-up or base-down a displacing prism is installed, and if the user's vertical deviation does not change which is expected because the display is dissociated, then the user's visual setting should change by the amount of the displacing prism. For example, if a base-up prism with a displacing power of 10 prism diopters is placed before the right eye, then the user would be expected to move the right eye's monocularly visible display element up by approximately 10 prism diopters in eth alignment task relative to the baseline setting. Such results may indicate that the test is performing correctly. For example, a value entered by the user less than the dissociating physical prism's value would suggest the user has a phoria tolerance of some degree, and not necessarily that the program/test is not performing correctly.

In additional or alternate embodiments, the system can be utilized to perform other types of objective cover tests, such as a unilateral cover (cover-uncover) test, a simultaneous prism cover test, and/or an alternating cover test. In implementations, an objective cover test can include simulation of a standard cover test in display of the HMD and use eye tracking to collect data related to how the eyes move. For example, a unilateral cover test can be performed at 6 m and 40 cm demands, and enable categorization of either heterotropia (tropia or squint) and heterophoria (phoria). In this example, both eyes are directed at a target, and one eye is occluded for 1-2 seconds and the movements of the non-occluded eye (unilateral cover test) and occluded eye (cover-uncover) are tracked. Movements are graded as: exo (eye moves in), eso (eye moves out), or vertical (deviation shared between the eyes leading to movement is equal yet opposite). In another example, a simultaneous prism cover test can be performed at 6 m and 40 cm demands, where a prism of a specified strength is oriented in the appropriate direction for the deviation (determined by the unilateral cover test) and is placed over the non-fixating eye, while the fixating eye is simultaneously occluded. The prism can be adjusted, for example by one diopter increments every 10 seconds, until there is no shift in fixation or the deviation is neutralized. This method affords measurement of small angle tropias without dissociating the patient (and thus bringing out an underlying phoria). In yet another example, an alternating cover test can be performed at 6 m and 40 cm demands, where occlusion is alternated between eyes and held for approximately one second. The movements of the eyes are tracked after the alternation of occlusion. Prisms of varying strengths and orientations are interposed in the line of sight until nulling (elimination) of the eye movements is achieved. The strength and orientation of the prism needed to null the eye movement is correlated to a measurement of the amount of deviation. The patient's fixation can be directed to the nine cardinal positions of gaze (i.e., straight ahead (primary), both eyes upwards (elevation), both eyes downwards (depression), both eyes to the right (dextroversion), both eyes up and to the right (destroelevation), both eyes down and to the right (dextrodepression), both eyes to the left (laevoversion), both eyes up and to the left (laevoelevation), and both eyes down and to the left (laevodepression)) and measured in each to assess the level of comitance (a characteristic of strabismus in which the misalignment of the eyes is maintained in all directions of gaze).

In still other examples, other methods of estimating phoric/tropic posture (that require accurate fixation and normal retinal correspondence, which can be difficult if an eye is deeply amblyopic) can be performed via the systems and methods disclosed herein. For example, the system can be configured to perform corneal reflex testing at near distances, such as Hirschberg testing (in which corneal reflex should be slightly nasal, 1 mm=22PD), Krimsky testing (using prisms to match corneal reflexes), and/or Angle lambda testing (using alternating occlusion, where the corneal reflexes should be the same and if the corneal reflexes are not the same, it is likely that the patient has ARC (anomalous retinal correspondence)). In another example, the system can be configured to perform a Maddox rod test to assess binocular alignment of the eyes. By using lenses to vary an amount of prism, two visual targets (one seen by each eye) can be brought into perceptual alignment, which can be indicated by user input (e.g., the patient reports alignment of a fixation target in one eye and line created by the Maddox rod in the other eye). The amount of prism needed for alignment can be measured in the nine cardinal positions of gaze (discussed above) at for near and/or far viewing distances. In yet another example, the system can be configured to perform a Von Graefe test, where lenses including a dissociating prism separate a focal point visual target (e.g., spot of light, letter(s), other). The amount of dissociating prism can be reduced in the horizontal axis until user input indicates vertical alignment of the visual targets. The dissociating prism can then be returned to the starting value and the amount of dissociating prism is reduced along the vertical axis until the user input indicates horizontal alignment of the visual targets.

In embodiments, the foregoing objective cover tests can be implemented within a head-mounted display (such as, the HMD 100 or other) including cameras configured to record/detect the positions of the left and the right eyes. For example, the display can change dynamically to show one or more visual stimuli to the user, and monitor, after a change of the binocular display to either occlude or reveal a visual stimulus to one of the two eyes while the stimulus remains visible to the other eye, when either of eyes responds to the visual target (e.g., a magnitude and a direction of a change in position of the eye).

Further, in embodiments, the foregoing cover tests can be used to measure various types of ocular misalignment, including esotropia, exotropia, hypertropia, hypotropia, esophoria, exophoria, hyperphoria, hypophoria, combined phoria and tropia, alternating exotropia, alternating esotropia, intermittent exotropia, intermittent esotropia, accommodative esotropia, heterophoria, heterotropia, combined heterophoria and heterotropia, and alternating heterotropia. Measurements and/or other collected data can be used to diagnose disorders of eye alignment including strabismus, convergence insufficiency, convergence excess, divergence insufficiency, and divergence excess, cranial nerve 3, 4, or 6 paresis, and cranial nerve 3, 4, or 6 palsy. The cover tests may be performed with the eyes at neutral gaze or at an eccentric gaze and using a distant or near target and/or using lenses to stimulate or relax the accommodative system of the eyes, to evaluate the commitancy, pattern, and frequency of an ocular misalignment.

Figure 5J:
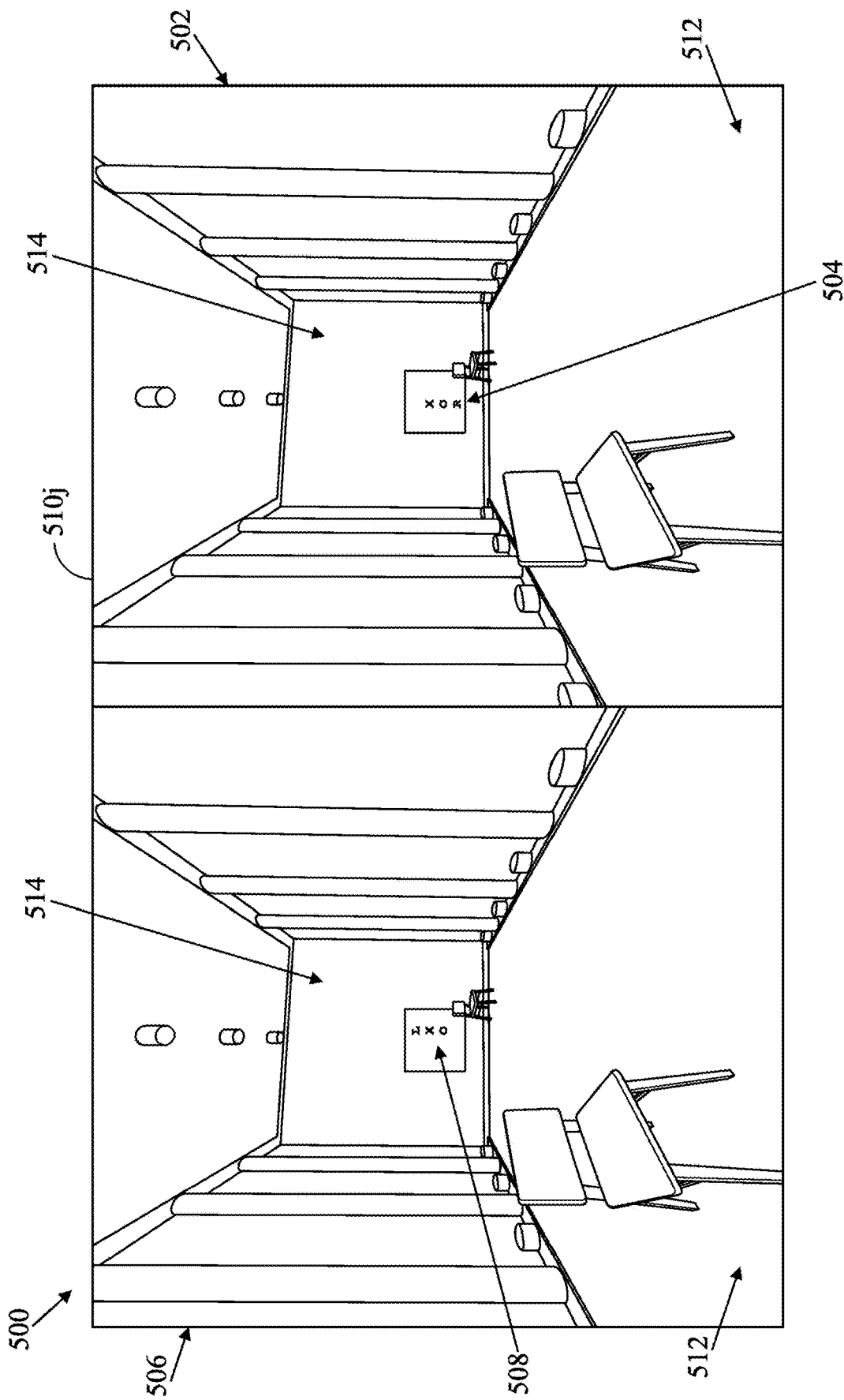
FIG. 5J is another view of an exemplary testing/training scenario generated on a display, which includes visual targets that are configured for assessing phoria in accordance with embodiments of the present disclosure.

Yet further, in embodiments, at the start of a phoria test (or other tests for vergence eye posture or accommodative response), a display can be created that simulates viewing of a scene in the distance. For example, the display can portray objects at a distance of 6 m, including many cues to distance, such as motion parallax, occlusion of one object by another within the field of view, perspective cues, location on the ground-plane cues, near blur cues, and familiar size cues. This initial display can be used to eliminate or minimize the user's near response that would otherwise cause the user of a head-mounted display to accommodate near and have vergence eye posture for near objects, thereby causing a bias in the measurement of these values when using the head-mounted display, relative to what a clinician would measure using real (far) stimuli during an optometric examination. An exemplary scenario 510*j* (a simulated scene) is illustrated in FIG. 5J, where the display 500 includes a simulated near portion 512 and a simulated far portion 514 of the virtual environment, which is displayed to the user as a perspective view of a room with a first chair at a near location and a second chair at a far location. The first visual stimulus 504 (a first vertical sequence of letters) is shown only to the right eye (i.e., displayed in the right eye-display 502) in the simulated far portion 514, and the second visual stimulus 508 (a second vertical sequence of letters, differing at least in part from the first sequence) is shown only to the left eye (i.e., displayed in the left eye-display 506) in the simulated far portion 514, and thereby the virtual environment enables testing for phoria at a simulated far distance. Similarly, in other implementations, the display may use cues to simulate near viewing, such as parallax, size, and blur to engage a user's near response. In the foregoing implementations, lenses can be used to stimulate or relax the accommodative system during testing.

Vergence Testing and Disorder Treatment

In embodiments, the methods and systems disclosed herein can be configured for vergence testing and/or vergence disorder treatment. As discussed above, a person who does not achieve simultaneous fixation with both eyes on the same part of a binocularly visible target is said to have a vergence disorder or dysfunction, and in order to assess vergence ability, a patient's vision can be put under stress (vergence demand). Vergence ability may be measured by testing vergence ability independently or by testing the vergence ability while the individual is accommodating. The starting point of an activity may be zero stress (or another level at which the individual can start the activity), and the amount of stress (or vergence demand) the individual's vision can tolerate is measured in degrees of visual angle or prism diopters by progressively increasing vergence stress via the vision assessment system. The amount of vergence demand the individual can withstand prior to image deterioration (i.e., an image becoming blurry and/or deteriorating so that an individual becomes diplopic) can be recorded, and then vergence demand can be reduced from this breakpoint until the individual is able to regain clear, single image vision. A near, far, or vertical breakpoint (i.e., a maximum demand that the vision of the individual is able to withstand) can be measured by adding (respectively) progressive near, far, or vertical demand to the visual stimulus on a single or repeated basis until the eyes are no longer able to maintain fusion, at which point they will relax to a more habitual posture. The system can measure vergence facility (how quickly the individual can respond with a convergent, divergent, supravergent, or infravergent eye movement in response to change in binocular disparity of a visual target), vergence accuracy (how well an individual can direct each eye at the same point in space), and/or vergence fatigue (how long an individual can maintain convergence eye posture when viewing a near visual target). Fixation stability (fluctuation in vergence eye posture) and fixation disparity (how far in front or behind the visual target the eyes are converged, which can be different for near and far targets) can also be determined.

The most common vergence disorder is convergence insufficiency (CI). A person with CI does not converge their eyes sufficiently, typically when looking at a near object, such as when reading or looking at a mobile phone or computer screen. Thus, CI can make it more difficult to do visual tasks, such as reading, and it can lead to headache, asthenopia (eye strain), blurry vision, double vision, and/or suppression by the brain of the images from one eye. CI is often comorbid with divergence excess (DE) and also with accommodative insufficiency (AI). Alternatively, a person with convergence excess (CE) over-converges their eyes when looking at a binocular target, typically more so when the target is far away.

Each of the vergence disorders (CI, DE, and CE) can be diagnosed and quantified by measuring the patient's vergence range, associated phoria under conditions of near and far viewing, and/or fixation disparity under conditions of near and far viewing utilizing the systems and methods described herein. These measurements can be made while interposed plus or minus lenses are used in combination with a head-mountable or other near/far distance display system. Further, each of the foregoing vergence disorders can be treated through the use of visual exercises utilizing the systems and methods described herein.

For example, a patient with CI may exhibit a greater exo eye posture at near than at distance when measured with a cover test utilizing the systems and methods disclosed herein. Additionally, a patient with CI may have a reduced range of convergent fusion ability and/or a larger than expected divergent fusion ability when assessed utilizing the systems and methods disclosed herein. A patient with DE may exhibit a greater exo posture at distance than at near when measured with a cover test utilizing the systems and methods disclosed herein. Additionally, a patient with DER may exhibit a reduced convergent fusion ability and/or a larger than expected divergent fusion ability when assessed utilizing the systems and methods disclosed herein. A patient with CE may exhibit a more eso posture at near than at distance when measured with a cover test utilizing the systems and methods disclosed herein. Additionally, a patient with CE may exhibit a reduced divergent fusion ability and/or a larger than expected convergent ability when assessed utilizing the systems and methods disclosed herein.

CI and DE are both conditions that occur in people who have the ability to converge their eyes, but who struggle to maintain a vergence eye posture that matches the current vergence demand. Such individuals may not have comfortable binocular vision. Thus, exemplary implementations of training are configured for extending the ranges over which users with CI and/or DE can comfortably converge. In one specific example of a treatment method for CI, the vergence demand of a visual target is increased while the user continues to track it using motor fusion, thereby causing the patient to spend more time with their eyes in a crossed state.

In order to converge their eyes properly, an individual's vision system may first measure the absolute retinal disparity of the stimulus from the two eye's retinal images, and then to use that disparity measurement to make an appropriate vergence eye movement that reduces the disparity. Thus. CI may result from either a sensory deficiency or a motor deficiency, or from a combination of deficiencies. For example, CI may result from a sensory deficiency in the visual system's ability to measure absolute retinal disparity, even though the motor responses to the incorrect disparity measurement are appropriate for that measurement. In another example, CI may result from the incorrect or incomplete use of absolute retinal disparity by the individual's motor system to control vergence eye posture, even though the system is able to measure the disparity correctly. In such examples, a strong exophoria may exist if the motor commands to control eye posture are biased in favor of an exophoric posture, or if the eye muscles have a resting position that is exophoric. As an exemplary generalized treatment strategy, a skill can be improved through the use of exercises that require that skill and that are somewhat challenging, but not so challenging as to be impossible. Therefore, if the CI is caused by a deficiency in the ability to measure disparity, it may be an effective strategy to provide exercises that target the sensory system that measures disparity, for example by requiring frequent, small changes in vergence eye posture in response to frequent small changes in disparity (vergence demand), and the use of binocular stimuli in which the disparity is conveyed by progressively smaller images. Alternatively, if the CI is caused by incorrect use of correctly measured disparities, an effective treatment strategy may be to provide exercises that target the motor system, for example exercises that require maintaining a highly converged eye posture. Holding such a posture may require overcoming a predisposition in the neural motor control or eye muscles that favors exophoric posture. It will be appreciated that an individual with CI may have deficiencies in both the sensory and motor systems, and both treatment methods can be applied utilizing the systems and methods disclosed herein.

In implementations, methods of visual rehabilitation for vergence disorders incorporate manipulation of the visual stimulus via the utilization of prisms. For example, within the headset, a virtual prism can be applied by the manipulation of the display for the left, right, or both eyes using base up (BU), base down (BD), base in (BI), base out (BO), or incyclo/excyclo directions using degrees or prism diopters (PD). The program can be set to perform the vergence training at various distances, such as far, near, or over a range between near and far distances. The vergence demand can start at the orthophoric position or where the user can perform the task of maintaining a single and clear image. The stimuli can be a stereoscopic or a flat visual target configured to stimulate fusion, which is adjustable in size, shape, location, disparity, contrast, and/or color. Adjustments of the stimuli can be made in the BU, BI, BO, or torsional directions. The amount of the adjustment can be a step order or jump vergence, which is a return to orthophoria (a condition of binocular fixation in which the lines of vision meet at the object toward which they are directed, and considered as a normal condition of balance of the ocular muscles of the two eyes) or another preset value. The stimuli can be presented for a limited duration or until the user input indicates that the perceptual criterion has been reached.

Further, in implementations, the inclusion lenses that can stimulate or relax accommodation can be utilized to make the treatment task easier or more difficult. For example, most people find it more difficult to maintain a convergence eye posture for near objects if plus lenses are introduced, as this situation requires simultaneously relaxing accommodation and converging the eyes. In another example, it is often more difficult to maintain a divergent eye posture if minus lenses are introduced, as they can cause a requirement of accommodation for near. These conditions can be used as training conditions to build up a patient's ability to make vergence eye movements, and maintain vergence eye posture, that is less dependent on their accommodative state than before the training. In one specific treatment example, a user can do base-out vergence with plus lenses (where a base of a prism placed on the temporal side) and base-in vergence with minus lenses (where a base of a prism placed on the nasal side), or alternatively, bifocal lenses have a minus region and a plus region can be utilized.

The vergence eye posture of the patient can be monitored across changes in accommodative demand that are caused by the lenses, for example, by using cameras in the HMD that are pointed at the eyes. The lenses that cause the change in accommodative demand can be of a single power, with the change of power occurring by swapping the lens for a different lens, or multiple powers in a single lens (such as the bifocal, trifocal or progressive lenses described above, with the change of power occurring by the user viewing the display through a different region of the lens.

In implementations, the virtual objects and/or environment used for these training activities can be generate on the display within the headset utilizing a web browser, which can be enjoyable to the user. The binocular display of the browser within the headset can be manipulated to increase or decrease its vergence demand, by means of lateral displacement of images for the right and left eyes in opposite directions. Alternatively, the training activity for which the vergence demand is manipulated can be implemented by displaying a movie, or a commercially available video game. The vergence demand can be changed quickly or slowly, and increased or decreased, with or without a change in the dioptric power of the lenses through which it is seen by the user.

Exemplary vergence training exercise scenarios 510k and 510l are illustrated in FIGS. 5K and 5L. As can be seen therein, in scenarios 510k and 510l, two monocularly visible targets are displayed. Specifically, a first visual stimulus 504 (a chicken) is shown only to the right eye (i.e., displayed in the right eye-display 504) and a second visual stimulus 508 (an egg) is shown only to the left eye (i.e., displayed in the left eye-display 506). Further, in the scenarios 510k and 510l, the actual combined display 500a is illustrated below the corresponding perceived binocular display 500b. While viewing the displayed visual stimuli, the user/patient can move one of the objects in one of the eyes, or both objects in opposite directions in the two eyes, until the patient perceives that the objects (the chicken and the egg) are aligned, as shown in each of the patient perception views 500b for the scenarios 510k and 510l. The positions of the two objects in world space (as in views 500a for scenarios 510k and 510l) can then be utilized to calculate convergence of the eyes. As can be seen in FIG. 5K, the patient is able to perform the exercise correctly and line up the visual stimuli and perform normal convergence, whereas in FIG. 5L the patient moves the first visual stimulus 504 (the chicken) to an improper location (not aligned with the egg) although the patient perceives alignment of the targets. This task can be implemented as a game that is administered intermittently during treatment activities, to assess the user's binocular deviation, and ensure that the horizontal vergence demand during training is neither too small (too easy to maintain) nor too large (too difficult to maintain). For example, if the associated deviation measured by the test is less than for example 0.5 degrees, then the vergence demand during the activity could be increased. If the associated deviation is greater than for example 1.0 degrees, then the vergence demand could be decreased.

This training exercise can optionally be performed in the presence of binocularly visible display elements that are the same in both eyes (e.g., an egg is displayed to each eye) and are used as a stimulus for convergence. The vergence demand of the binocularly visible display elements defines the vergence demand of the test. For example, if the binocularly visible display elements have a vergence demand of 10 degrees, then the test assesses actual vergence under conditions of a vergence demand of 10 degrees. It will be appreciated that the system can be utilized to control and/or change the vergence demand of the visual targets.

In embodiments, the systems and methods described herein enable vergence adjustments for comfort that facilitates the maintenance of binocular fusion of visual stimuli. For example, a person viewing an HMD display who looks from a near visual stimulus to a far visual stimulus (or from a far visual stimulus to a near visual stimulus) within a depicted scene will have to make a vergence eye movement to achieve binocular fixation and fusion. Without such a vergence eye movement, the person viewing the display will, after the change in simulated viewing distance, see two images (diplopia, one from each eye) or suppress one image. In some applications with an HMD, the vergence demand of the display is controlled by the computer and associated programming. For example, the scene may be replaced by a new scene (in other words, there may be a "scene cut") at a different simulated viewing distance, or blur cues may indicate to the person viewing the display that the visual target has changed to an object at a different distance. In the latter case, "racking the focus" may be used to specify which object within the scene should be attended to (by e.g., making one object appear in focus while others are blurred), and consequently, which new object should be looked at by the person viewing the display. The scene cut or change of blur may be achieved by the actions of a clinician/operator or can be carried out via a computer algorithm/software steps.

Typically, when a person who does not have presbyopia (farsightedness) and who does not have implanted lenses makes a vergence eye movement, they also change their accommodation and vice versa. Accommodative demand and vergence demand covary completely across objects in a natural scene, provided the eye's pupil size (whether natural or artificial) is larger than a pinhole. Near objects require more accommodation to be seen in focus, and greater vergence to be seen with binocular fusion than do far objects. An individual's visual system is built in a way that takes this relationship into account. A convergent eye movement is accompanied by an increase in accommodation, even in artificial displays that do not require any change of accommodation to remain in focus, and a divergent eye movement is similarly accompanied by a decrease in accommodation. An increase of accommodative status to viewing a closer object is accompanied by a convergent eye movement even when one eye is occluded, and a decrease of accommodative status to viewing a far object is similarly accompanied by a divergent eye movement. Utilizing the system and methods described herein, fixation disparity curves can be measured. One use of measured fixation disparity curves is during the diagnostic procedure known as graphical analysis, which is a method for assessing the influence that vergence and accommodation have on one another within the patient's visual system.

Due to the fixed accommodative demand in an HMD, the vergence eye movement made by a user viewing the display must be made without changing accommodation (if the display is to remain in focus). However, due to the convergent-accommodation-to-convergence gain or ratio (CAC ratio), it may be difficult or impossible for the person viewing the display to avoid changing their accommodation when making the vergence eye movement. Alternatively or additionally, due to the accommodative-convergence-to-accommodation gain or ratio (ACA ratio), it may be difficult or impossible for the person viewing the display to make a vergence eye movement of sufficient magnitude to match the change in vergence demand of the scene.

Also, an artificial display (such as the HMD 100 or other) may generate a visual stimulus containing a virtual object for which accommodative demand and vergence demand specify different simulated distances. For example, if the accommodative demand is 0.67 diopters, then accommodation specifies a distance of 150 cm, and any vergence demand other than 11150 radians, where I is the interocular distance in cm (usually approximately 6 cm), specifies a viewing distance different from 150 cm. For example, if the vergence demand is 1/50 radians, then vergence demand specifies an object distance of 50 cm rather than the 150 cm specified by accommodation. If such a mismatch persists for a length of time, the vision of an individual or user viewing the display may adapt to the mismatch. In that case, rather than having accommodation and vergence that are both appropriate to the same distance, for example 150 cm, one or both of accommodation and vergence may change to become closer to the accommodative or vergence demand of the display. For example, the individual viewing the display may come to have an accommodation of 0.67 D. which is appropriate to bring objects into focus at a distance of 150 cm, but a binocular vergence eye posture of 1/50 radians, which is appropriate to achieve binocular fusion at a distance of 50 cm.

For a person whose vision has adapted to different distances for accommodation and vergence, changes in viewing distance due to scene cuts or rack focusing may be uncomfortable, because change of vergence may cause a change of accommodation, and vice versa, due to the CAC and ACA ratios for change, respectively. If this happens, the visual system may issue neural commands to the ciliary body (which controls accommodation) or to the eye muscles (which control vergence) that cannot be fully executed because the command conflicts with physical limitations or with other neural commands. For example, if the accommodative demand of the display is 150 cm, and the user's accommodation is at 150 cm, and vergence demand of the display is at 50 cm, and the user's vergence is at 50 cm, and there is subsequently a change of scene that specifies a new vergence demand (for example going from 50 cm to infinity), then the vergence change of the display will be from 1/50 to 0. A vergence change of this amount normally corresponds to a change of accommodative demand from 2.0 diopters to 0 diopters (i.e., an accommodative change of −2.0 diopters). However, if the user's accommodation is appropriate for 150 cm before the change of display (in other words, equal to 0.67 D), then a command to the ciliary body to relax accommodation by −2.0 D will not be possible in an emmetropic individual because normal accommodative states are non-negative (appropriate for distances no farther than infinity) when measured in diopters.

Similarly, a change in the accommodative demand of the display may cause an accommodative response that is accompanied by a vergence response due to the ACA ratio. If the person is adapted to different distances for accommodation and convergence, a distance change may cause discomfort. For example, if the person is verged for 50 cm and accommodated for 150 cm, and the display is capable of changing the accommodative demand to be very near, then the vergence system may be instructed by the brain to converge to a new value that is too large to be comfortable. Alternatively, if accommodation and vergence are adapted to be appropriate for 50 and 150 cm, respectively, and the accommodative demand is decreased by 2.0 D, then the associated vergence change, measured in degrees or diopters of convergence, may cause the eyes to diverge (turn out) relative to infinity, which is very uncomfortable in many people who have normal vision.

To alleviate the discomfort caused by changes of vergence demand in displays with fixed accommodative demand, the systems and methods disclosed herein can be configured to generate a change in vergence demand of the display that is artificially reduced compared to its natural value. In exemplary implementations, in cutting from a scene that simulates a change of distance from 50 cm to infinity in a display with fixed accommodation at 150 cm, the change in vergence demand can be artificially reduced in magnitude from 1/50 to a smaller value, for example going from 1/50 to 1/100 rather than from 1/50 to 0. This can be done in VR, for example, by rotating the virtual cameras that are used to create images for each of the two eyes, which simulates the use of a horizontal prism. Therefore, a person will not have to make a large vergence eye movement to maintain fusion of the display, and consequently the change of accommodation, relative to fixed accommodative demand, will not be as large as it would otherwise. This phenomena can be called "changing the zero point."

This method, namely setting the change of vergence to be smaller than would be the case in the real world as specified by distance cues other than vergence (for example, distance cues such as familiar object size, location on the ground plane, motion parallax, blur cues, etc.), can also be carried out in exemplary implementations to re-train the visual system during vision therapy. For example, a person may need training for making vergence eye movements, and already be able to make small vergence eye movements but not large vergence eye movements (such as, e.g., a person with a strong phoria or with strabismus). In such an example, other distance cues may specify a large change in distance between two objects that the viewer of the display is asked to look at, but, as part of a training protocol to help the person learn how to make larger vergence eye movements, the vergence demand can automatically be made smaller than real world vergence demand.

In implementations, to reduce the change in vergence demand throughout the display, in addition to the above-described method of changing the zero-point dynamically in concert with a change of attentional focus to an object at a new distance, a baseline can be reduced between the two virtual cameras that are being used to render the display to the two eye. This technique can simulate a smaller interpupillary distance so that all relative disparities are scaled down by the ratio of the new baseline relative to the old baseline. For example, if the cameras are set to be 1 cm apart, binocular disparities measured across the images from the two cameras will have one-sixth of their normal magnitude, as compared to disparities measured if the cameras are spaced the same as the eyes of a person whose eyes are 6 cm apart. In this example, the zero-point must be set, which will determine the unique viewing distance at which vergence demand is objectively correct. At closer distances, vergence demand can be increased but to a lesser degree other distance cues, and at farther distances, vergence demand can be decreased but to a lesser degree than other distance cues.

In additional or alternate implementations, the system can be configured to generate a greater vergence demand than would be the case in the real world as specified by distance cues other than vergence (for example, cues such as familiar object size, location on the ground plane, motion parallax, blur cues, etc.). Such techniques could be used to stimulate vergence eye movements in a patient who is unable to use binocular disparity for that purpose. The use of correlated distance cues can be used to train the visual system how to use binocular disparity to control horizontal vergence eye posture. For example, most people who can accommodate will make a convergence eye movement in response to a change of accommodative demand.

In embodiments, the system can be configured to perform cyclovergence training operations. Normal cyclovergence (rotation of the eyes about their visual axes to bring the retinal images into rotational alignment) can cause the eyes to rotate relative to one another by approximately 8 degrees. An additional 8 degrees of sensory fusion can make it possible for normal vision to overcome approximately 16 degrees of variation in the rotational alignment of images shown or displayed to the two eyes. Methods for training cyclovergence ranges can be analogous to those for training vergence ranges, described above, except that within the head-mounted display, the image for one eye can be rotated relative to the image in the other eye, instead of being displaced to the left, right, up, or down. For example, a visual target displayed to the left eye can be rotated by 8 degrees relative to a visual target displayed to the right eye. The measured degree of cyclovergence may be applied to the in-HMD tests and activities, and may be adjusted over time to improve a user's cyclovergence.

Accommodation Testing and Disorder Treatment

In embodiments, the methods and systems disclosed herein can be configured for accommodation testing and/or accommodation disorder treatment. As discussed above, accommodation is the ability of the eye to increase its refractive power of the crystalline lens in order to focus near objects on the retina, and, in order to assess the ability to accommodate, the system can measure accommodative amplitude (the total range or amount that a person can accommodate, usually expressed in diopters, such as 1/m or meters$^{-1}$), facility (how quickly the patient responds to a change of accommodative demand of the visual stimulus and/or how long it takes to achieve criterion accommodative state), and/or accuracy (how closely the accommodative state matches the demand of the visual stimulus to bring it into focus). In implementations, one or more of these functions can be measured indirectly by monitoring the pupil constriction responses in at least one eye, for example, by using one or two cameras placed within the headset that are pointed at the left and/or right eyes. The foregoing functions can be defined independently of overall refractive state or ability, as amplitude is defined by the difference in near and far accommodative endpoints independent of whether the eye(s) being tested are myopic (nearsighted), emmetropic (having no visual defects), or hyperopic (farsighted). Thus, amplitude can be measured while a person is wearing prescribed ophthalmic lenses that allow them to see clearly at near or far distance.

In implementations, the ability of a patient to accommodate can be tested using an HMD by determining whether the user is able to identify the image of an object with sufficiently fine detail to require good focus. For example, the user can be asked to report (verbally or by other user input) the orientation of a Landolt-C stimulus, the identity of a letter optotype, or the identity of a familiar object, such as an animal or a household object. Further, in implementations, the ability of a patient to accommodate can be tested using an autorefractor. Further still, in implementations, the ability of a patient to accommodate can be tested using a measurement of pupil size obtained from a camera pointed at the eye, for example, an infrared camera or visible-light camera mounted in the HMD.

In implementations, for accommodation training, the system can be configured to present two or more accommodative demands in different visual directions, with the user being asked to do a task alternately at different optical distances in the different visual directions. Further, in implementations, training to accommodate near and far can be done using an augmented reality display device, wherein one distance is provided by direct viewing of an object in the real world, and the other is provided by the accommodative demand of a simulated object in the augmented reality display.

In implementations, a lens can be mounted into an HMD between the eye and the display for accommodation training. It can be mounted in front of one eye or both eyes, and can be mounted in a holder that is attached to the headset, or to a holder that is attached directly to the user, such as in eyeglass frames. For example, one or more of the lenses discussed above with reference to FIGS. 1A-1I can be utilized, such as lenses that have more than a higher power and a lower power disposed in two or more regions of the lens (e.g., a bifocal lens having a plus power in the top portion of the lens and a minus power at a bottom portion of the lens).

Figure 5M:
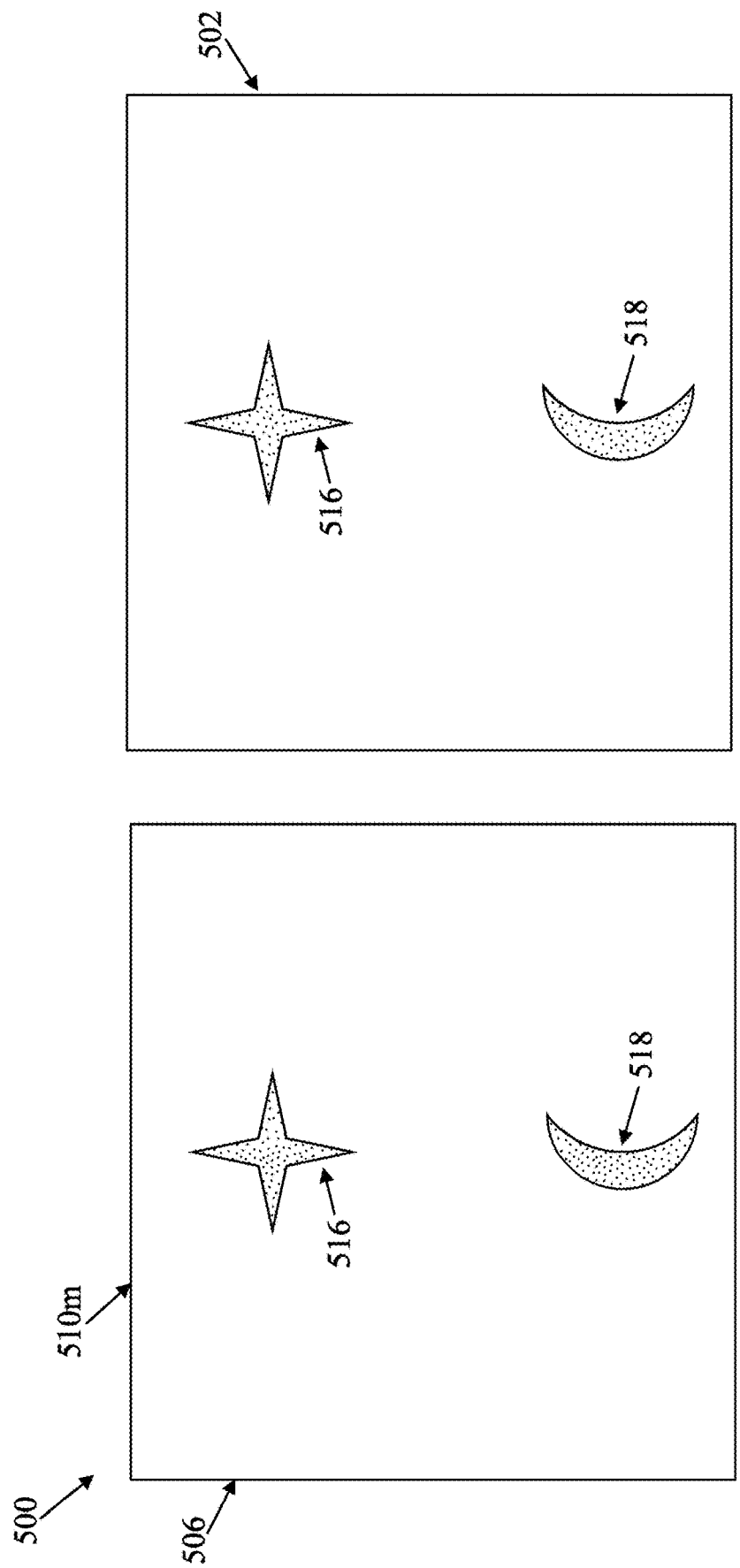
FIG. 5M is a view an exemplary testing/training scenario generated on a display, which includes visual targets that are configured for assessing and/or treatment of accommodation disorders in accordance with embodiments of the present disclosure.

An exemplary scenario 510m for accommodation training is illustrated in FIG. 5M. As can be seen therein, a first visual stimulus 516 (a star) and a second visual stimulus 518 (a moon) are shown on the display 500 (in each of the right eye-display 502 and the left eye-display 506). Bifocal lenses having a plus power in the top portion of the lens and a minus power at a bottom portion of the lens can be used in combination with the HMD (or other display system), such that the user can view the first visual stimulus 516 though the top (plus) portion of the lens, and can view the second visual stimulus 518 through the bottom (minus) portion of the lens. When the user looks at the first visual stimulus 516, the plus-power portion of the lens causes a decrease in the accommodative demand of the display as compared to direct viewing of the display without the interposed lens. To bring this image into focus, the user must relax his or her accommodation (as compared to looking at the first visual stimulus without the lens). When the user looks at the second visual stimulus 518, the user must accommodate (as compared to looking at the second visual stimulus without the lens). Accordingly, the bifocal lens and the displayed visual targets can be utilized to simulate accommodative demands similar to those of natural viewing, where a near object is located in the lower visual field and a far object is located in the upper visual field. The ability of the user to accommodate in response to viewing stimuli through the two parts of the lens can be assessed by an autorefractor in communication with the system.

It will be appreciated that similarly configured bifocal lenses of different plus and minus powers, or trifocal or progressive lenses having a plus power a top portion of the lens and minus power can be utilized with the HMD for accommodative training. Further, in implementations, the lenses can be constructed so that the powers take into account any refractive error of the user's eyes. For example, a user who normally wears lenses with minus power to correct for myopia could, instead of wearing their own lenses, use lenses that incorporate the minus power of their ophthalmics into the bifocal lenses configured for accommodative training.

As discussed above, in alternate implementations a normally configured bifocal lens (or trifocal lens or progressive lens) having a minus power at the top portion and a plus power at the bottom portion thereof can be utilized with the HMD, however, the configuration may be less natural to the user, as they would be required to visualize the first visual stimulus 516 at a simulated near distance and the second visual stimulus 518 at a simulated far distance.

In embodiments, the systems and methods disclosed herein enable visual training for accommodation and vergence simultaneously and independently. In human vision, accommodation and vergence are controlled by interlinked (or yoked) anatomical systems. In healthy (optimal) vision, a stimulus to vergence causes both a vergence response and an accommodative response, due to the CA/C ratio (convergent accommodation in response to convergence). Further, in a healthy (optimal) vision, a stimulus to accommodate causes both a vergence response and an accommodative response, due to the AC/A ratio (accommodative convergence in response to accommodation).

However, a person who does not accommodate completely or who does not converge completely when viewing a near stimulus may benefit from exercises that require accommodation and convergence. It is beneficial for some patients to exercise changes in accommodation while viewing stimuli in which the distance specified by vergence demand agrees with, or does not change, or moves opposite to, the distance specified by accommodative demand. Further, it is beneficial for some patients to exercise changes in vergence while viewing stimuli in which the distance specified by accommodative demand agrees with, or does not change, or moves opposite to, the distance specified by vergence demand. By manipulating the right eye and left eye-displays to control vergence demand, and using lenses such as those shown and described above with reference to FIGS. 1A-1I, all of these training scenarios can be generated in an HMD or other display system.

For example, returning to FIG. 5M, using bifocal lenses having a plus power at top portion thereof and a minus power at a bottom portion thereof interposed between each eye the display, a person with convergence insufficiency could be asked to do an identification task that requires bringing the stimulus into focus alternately at the locations of the first visual stimulus 516 and the second visual stimulus 518. At the start of training, the difference in power can be small, for example 0 diopters (D) of power in the top half of the lens and −2 D in the bottom half of the lens. If the headset had a fixed accommodative demand of 0.5 D (2 meters distance), then the lenses would cause the accommodative demand to be 0.5 D at the top and 2.5 D at the bottom. After receiving user input indicative of an ability to focus at these two distances, the difference in power could be increased (e.g., incrementally increased), for example to 4 D, and so on. When the lenses have powers of +0.5 D at the top and −49.5 D at the bottom, then the accommodative demand of the display in the headset will be 0 D at the top and −50 D at the bottom, which corresponds to objects viewed at optical distances of infinity and 20 cm, respectively.

It will be appreciated that one or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable computer hardware, which can be special or general purpose processor, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system configured for one or more of assessment or training of one or more vision disorders of a user, the system configured for data communication with a display apparatus, the system comprising:
   one or more processor apparatus; and one or more computer-readable storage media having a plurality of computer-executable instructions stored thereon, the plurality of computer-executable instructions configured to, when executed by the one or more processor apparatus, cause the system to perform a plurality of steps comprising:
   identifying a specified exercise for display on the display apparatus, the specified exercise being one of a plurality of exercises configured for one or more of assessment or training of at least one of vergence ability or accommodation ability of the user;
   identifying data related to one or more lenses for use in combination with the display apparatus;
   based at least on the data related to the one or more lenses, calculating one or more correction factors for image display on the display apparatus, wherein the calculating the one or more correction factors for image display on the display apparatus comprises calculating, for an eccentric visual stimulus of the series of visual stimuli, a scaling factor, the scaling factor comprising one of a magnification factor based on a minification power of a minus lens or a minification factor based on a magnification power of a plus lens;
   causing display, on the display apparatus and based at least on the specified exercise and the one or more correction factors, a series of visual stimuli to at least one eye of the user, each visual stimulus of the series of visual stimuli configured to have a specified vergence demand and a specified accommodation demand;
   tracking one or more of a vergence response or an accommodation response of the user;
   comparing the one or more of the vergence response or the accommodation response to one or more standardized values for vergence response or accommodation response; and
   determining, based at least on the comparing, a result indicative of whether the one or more of the vergence response or the accommodation response is associated with visual disorder.

2. The system of claim 1, wherein the system is configured to enable, based on the specified exercise targeting accommodative disorder, each visual stimulus in the series to have, relative to one or more other visual stimuli of the series, fixed vergence demand and varying accommodative demand;
   wherein the system is further configured to enable, based on the specified exercise targeting vergence disorder, each visual stimulus in the series to have, relative to one or more other visual stimuli of the series, fixed accommodative demand and varying vergence demand; and
   wherein the system is further configured to enable, based on targeting the specified exercise targeting combined vergence and accommodation disorder, each visual stimulus in the series to have, relative to one or more other visual stimuli of the series, a varying combination of accommodative demand and vergence demand.

3. The system of claim 1, wherein the display apparatus comprises ahead-mountable display device comprising one or more eye tracking sensors, and wherein the plurality of steps further comprises:
   causing calibration of the one or more eye tracking sensors to the at least one eye of the user; and
   utilizing data received from the one or more eye tracking sensors for the tracking of the one or more of the vergence response or the accommodation response of the user.

4. The system of claim 1, wherein the display apparatus comprises a multi-distance display apparatus comprising a first display device and a second display device, the first display device positioned distal of the second display device relative to the user.

5. The system of claim 4, wherein the second display device comprises a computerized mobile device comprising a forward facing camera and a rearward facing camera, wherein the forward facing camera is configured to enable a determination of a first distance between the computerized mobile device and the first display device, and the rearward facing camera is configured to enable a determination a second distance between the computerized mobile device and the user, and
wherein the plurality of steps further comprises:
receiving, from the computerized mobile device, data indicative the first distance and data indicative of the second distance, wherein the causing display of the series of visual stimuli to the at least one eye of the user is further based on the data indicative of the first distance and the data indicative of the second distance;
receiving, from a user input device, data indicative of user input with respect to perception of visual stimuli; and
utilizing the data indicative of user input with respect to perception of visual stimuli for the tracking of the one or more of the vergence response or the accommodation response of the user.

6. The system of claim 1, wherein the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a region of a lens, or a curvature of a lens.

7. The system of claim 1, wherein the plurality of steps further comprises:
determining, based at least on the tracking the one or more of the vergence response or the accommodation response of the user, an accommodation value associated with the accommodation response, the accommodation value comprising one or more of an accommodative amplitude, an accommodative facility, an accommodative accuracy, an accommodative-convergence-to-accommodation gain or ratio (ACA ratio), or a convergent-accommodation-to-convergence gain or ratio (CAC ratio).

8. The system of claim 1, wherein the plurality of steps further comprises:
determining, based at least on the tracking the one or more of the vergence response or the accommodation response of the user, a vergence value associated with the vergence response, the vergence value comprising one or more of a vergence facility, a vergence accuracy, a vergence fatigue, a fixation stability, a fixation disparity, or a binocular fixation breakpoint.

9. The system of claim 1, wherein the plurality of steps further comprises:
identifying data related to an interpupillary distance mismatch between the user and at least two of the one or more lenses, wherein the calculating the one or more correction factors for image display is further based on the interpupillary distance mismatch, and comprises calculating, for a visual stimulus of the series of visual stimuli, a displacement factor.

10. The system of claim 1, wherein the comparing the one or more of the vergence response or the accommodation response to the one or more standardized values for vergence response or accommodation response comprises:
utilizing a look up table of standardized values based on one or more of average values from a plurality of individuals with healthy vision or simulated optimal vision values; and
evaluating the one or more of the vergence response or the accommodation response of the user relative to at least one standardized value in the look up table of standardized values.

11. The system of claim 10, wherein the at least one standardized value comprises an acceptable range, and the evaluating comprises determining whether the one or more of the vergence response or the accommodation response is outside of the acceptable range, and wherein the one or more of the vergence response or the accommodation response being outside of the acceptable range is indicative of visual disorder.

12. The system of claim 10, wherein the at least one standardized value comprises a threshold value, and the evaluating comprises determining whether the one or more of the vergence response or the accommodation response is below the threshold value, and wherein the one or more of the vergence response or the accommodation response being below the threshold value is indicative of visual disorder.

13. A method of operating a system configured for one or more of assessment or training of one or more vision disorders of a user, the method comprising:
identifying a specified exercise for display on a display apparatus, the specified exercise being one of a plurality of exercises configured for one or more of assessment or training of at least one of vergence ability or accommodation ability of the user;
identifying data related to one or more lenses for use in combination with the display apparatus, wherein the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a portion of a lens, or a curvature of a lens;
based at least on the data related to the one or more lenses, calculating one or more correction factors for image display on the display apparatus, wherein the calculating the one or more correction factors for image display on the display apparatus comprises calculating for an eccentric visual stimulus of the one or more visual stimuli, a scaling factor, the scaling factor comprising one of a magnification factor based on a minification power of a minus lens or a minification factor based on a magnification power of a plus lens;
causing display, on the display apparatus and based at least on the specified exercise and the one or more correction factors, of one or more visual stimuli to at least one eye of the user, each of the one or more visual stimuli configured to have a specified vergence demand and a specified accommodation demand;
tracking one or more of a vergence response or an accommodation response of the user;
comparing the one or more of the vergence response or the accommodation response to one or more standardized values for vergence response or accommodation response; and
determining, based at least on the comparing, a result indicative of whether the one or more of the vergence response or the accommodation response is associated with visual disorder.

14. The method of claim 13, further comprising identifying data related to an interpupillary distance mismatch between the user and at least two of the one or more lenses, wherein the calculating the one or more correction factors for image display is further based on the interpupillary distance mismatch, and comprises calculating, for a visual stimulus of the one or more visual stimuli, a displacement factor.

15. The method of claim 13, wherein the display apparatus comprises a head-mountable display device comprising one or more eye tracking sensors, and wherein the method further comprises:
causing calibration of the one or more eye tracking sensors to the at least one eye of the user, and
utilizing data received from the one or more eye tracking sensors for the tracking of the one or more of the vergence response or the accommodation response of the user.

16. The method of claim 13, wherein the display apparatus comprises a multi-distance display apparatus comprising a first display device and a second display device, the first display device positioned distal of the second display device relative to the user; and
wherein the method further comprises:
identifying data indicative a first distance between the first display device and the second display device:
identifying data indicative of the second distance between the second display device and the user, wherein the causing display of the series of visual stimuli to the at least one eye of the user is further based on the data indicative of the first distance and the data indicative of the second distance;
receiving, from a user input device, data indicative of user input with respect to perception of visual stimuli; and
utilizing the data indicative of user input with respect to perception of the one or more visual stimuli for the tracking of the one or more of the vergence response or the accommodation response of the user.

17. The method of claim 13, further comprising:
determining, based at least on the tracking the one or more of the vergence response or the accommodation response of the user, an accommodation value associated with the accommodation response, the accommodation value comprising one or more of an accommodative amplitude, an accommodative facility, an accommodative accuracy, an accommodative-convergence-to-accommodation gain or ratio (ACA ratio), or a convergent-accommodation-to-convergence gain or ratio (CAC ratio); and
determining, based at least on the tracking the one or more of the vergence response or the accommodation response of the user, a vergence value associated with the vergence response, the vergence value comprising one or more of a vergence facility, a vergence accuracy, a vergence fatigue, a fixation stability, a fixation disparity, or a binocular fixation breakpoint.

18. A system configured for one or more of assessment or training of a vision disorder associated with at least one of vergence ability or accommodation ability of a user, the system configured for data communication with a head-mountable display device, the system comprising:
one or more processor apparatus; and
one or more computer-readable storage media having a plurality of computer-executable instructions stored thereon, the plurality of computer-executable instructions configured to, when executed by the processor apparatus, cause the system to perform a plurality of steps comprising:
identifying a specified exercise for display on a head-mountable display device, the specified exercise being one of a plurality of exercises;
identifying data related to one or more lenses for use in combination with the head-mountable display device;
based at least on the data related to the one or more lenses, calculating one or more correction factors for image display on the head-mountable display device, wherein the data related to the one or more lenses comprises data indicative of one or more lens characteristics, the one or more lens characteristics comprising one or more of a type of lens, a power of a lens, a power of a region of a lens, a regional configuration of a lens, a prismatic characteristic of a lens, a prismatic characteristic of a region of a lens, or a curvature of a lens, and wherein the calculating the one or more correction factors for image display on the display apparatus comprises calculating, for an eccentric visual stimulus of the one or more visual stimuli, a scaling factor, the scaling factor comprising one of a magnification factor based on a minification power of a minus lens or a minification factor based on a magnification power of a plus lens;
calibrating one or more eye tracking sensors to at least one eye of the user;
causing display, on the head-mountable display device and based at least on the specified exercise and the one or more correction factors of a series of visual stimuli to at least one eye of the user, each visual stimulus in the series of visual stimuli configured to have a specified vergence demand and a specified accommodation demand;
tracking, via at least the one or more eye tracking sensors, one or more of a vergence response or an accommodation response of the user;
evaluating the one or more of the vergence response or the accommodation response relative to one or more standardized values for vergence response or accommodation response; and
determining, based at least on the evaluation, a result indicative of whether the one or more of the vergence response or the accommodation response is associated with visual disorder;
wherein the system is configured to enable, based on the specified exercise being a first type exercise targeting accommodative disorder, each visual stimulus in the series to have, relative to one or more other visual stimuli of the series, fixed vergence demand and varying accommodative demand;
wherein the system is further configured to enable, based on the specified exercise being a second type of exercise targeting vergence disorder, each visual stimulus in the series to have, relative to one or more other visual stimuli of the series, fixed accommodative demand and varying vergence demand; and
wherein the system is further configured to enable, based on targeting the specified exercise being a third type of exercise targeting combined vergence and accommodation disorder, each visual stimulus in the series to have, relative to one or more other visual stimuli of the series, a varying combination of accommodative demand and vergence demand.

* * * * *